United States Patent
Stayton et al.

(10) Patent No.: US 10,066,043 B2
(45) Date of Patent: Sep. 4, 2018

(54) ω-FUNCTIONALIZED POLYMERS, JUNCTION-FUNCTIONALIZED BLOCK COPOLYMERS, POLYMER BIOCONJUGATES, AND RADICAL CHAIN EXTENSION POLYMERIZATION

(71) Applicants: University of Washington, Seattle, WA (US); PhaseRx, Inc., Seattle, WA (US)

(72) Inventors: Patrick S. Stayton, Seattle, WA (US); Allan S. Hoffman, Seattle, WA (US); Anthony J. Convertine, Seattle, WA (US); Scott M. Henry, Seattle, WA (US); Robert W. Overell, Shoreline, WA (US); Paul H. Johnson, Snohomish, WA (US)

(73) Assignees: University of Washington, Seattle, WA (US); PhaseRx, Inc., Seattle, WA (US)

( * ) Notice: Subject to any disclaimer, the term of this patent is extended or adjusted under 35 U.S.C. 154(b) by 0 days.

(21) Appl. No.: 15/428,063

(22) Filed: Feb. 8, 2017

(65) Prior Publication Data

US 2017/0145141 A1 May 25, 2017

Related U.S. Application Data

(63) Continuation of application No. 13/133,355, filed as application No. PCT/US2009/067193 on Dec. 8, 2009, now Pat. No. 9,593,169.

(60) Provisional application No. 61/120,756, filed on Dec. 8, 2008.

(51) Int. Cl.
- A61K 31/74 (2006.01)
- C08F 293/00 (2006.01)
- A61K 49/00 (2006.01)
- A61K 47/48 (2006.01)

(52) U.S. Cl.
CPC .... *C08F 293/005* (2013.01); *A61K 47/48176* (2013.01); *A61K 49/0054* (2013.01); *C08F 2438/03* (2013.01)

(58) Field of Classification Search
None
See application file for complete search history.

(56) References Cited

U.S. PATENT DOCUMENTS

| | | | |
|---|---|---|---|
| 4,699,784 A | 10/1987 | Shih | |
| 5,057,313 A | 10/1991 | Shih | |
| 6,359,054 B1 | 3/2002 | Lemieux | |
| 6,383,811 B2 | 5/2002 | Wolff | |
| 6,410,057 B1 | 6/2002 | Kweon-Choi | |
| 6,780,428 B2 | 8/2004 | Ranger | |
| 6,835,393 B2 | 12/2004 | Hoffman | |
| 6,919,091 B2 | 7/2005 | Trubetskoy | |
| 6,939,564 B2 | 9/2005 | Ranger | |
| 7,009,004 B2 | 3/2006 | Tsuji | |
| 7,033,607 B2 | 4/2006 | Trubetskoy | |
| 7,081,503 B2 | 7/2006 | Tsuji | |
| 7,094,810 B2 | 8/2006 | Sant | |
| 7,098,032 B2 | 8/2006 | Trubetskoy | |
| 7,217,776 B1 | 5/2007 | Mallapragada | |
| 7,374,778 B2 | 5/2008 | Hoffman | |
| 7,510,731 B2 | 3/2009 | Ranger | |
| 7,524,680 B2 | 4/2009 | Wolff | |
| 7,718,193 B2 | 5/2010 | Stayton | |
| 7,737,108 B1 | 6/2010 | Hoffman | |
| 8,367,113 B2 | 2/2013 | Gu | |
| 2001/0007666 A1 | 7/2001 | Hoffman | |
| 2003/0134420 A1 | 7/2003 | Lollo | |
| 2003/0191081 A1 | 10/2003 | Lemieux | |
| 2003/0211167 A1 | 11/2003 | Gustavsson | |
| 2004/0072784 A1 | 4/2004 | Sant | |
| 2004/0151775 A1 | 8/2004 | Rozema | |
| 2004/0162235 A1 | 8/2004 | Trubetskoy | |
| 2005/0220880 A1 | 10/2005 | Lewis | |
| 2005/0260276 A1 | 11/2005 | Yang | |
| 2006/0134221 A1 | 6/2006 | Geall | |
| 2006/0165810 A1 | 7/2006 | Discher | |
| 2006/0171980 A1 | 8/2006 | Helmus | |
| 2006/0235161 A1 | 10/2006 | Heller | |
| 2007/0003609 A1 | 1/2007 | Collin-Djangone | |
| 2007/0010632 A1 | 1/2007 | Kaplan | |
| 2007/0037891 A1 | 2/2007 | Esfand | |
| 2007/0059271 A1 | 3/2007 | Kataoka | |
| 2007/0110709 A1 | 5/2007 | Ranger | |

(Continued)

FOREIGN PATENT DOCUMENTS

| | | |
|---|---|---|
| EP | 0 321 233 A1 | 6/1986 |
| EP | 2 180 004 A1 | 4/2010 |

(Continued)

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784 (Year: 1995).*

Benoit, D.S.W., et al., "Resensitizing Multidrug Resistant Cells to Doxorubicin Through plk1 Knockdown Using a Novel pH-Responsive Micelle siRNA Delivery System," Abstracts of Society for Biomaterials Meeting, Apr. 22, 2009, 1 page.

Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105-120, Dec. 2003.

Cheung, C.Y , et al., "A pH-Sensitive Polymer That Enhances Cationic Lipid-Mediated Gene Transfer," Bioconjugate Chemistry 12(6):906-910, Oct. 2001.

Cho, Y.W., et al., "Polycation Gene Delivery Systems: Escape From Endosomes to Cytosol," Journal of Pharmacy and Pharmacology 55(6):721-734, Jun. 2003.

(Continued)

*Primary Examiner* — Daniel M Podgorski
(74) *Attorney, Agent, or Firm* — Christensen O'Connor Johnson Kindness PLLC

(57) ABSTRACT

Polymeric compounds having spatially controlled bioconjugation sites are described. Functionalization is achieved by selective ω-terminal chain extension of polymer chains by radical polymerization, such as reversible addition-fragmentation chain transfer (RAFT) polymerization.

17 Claims, 8 Drawing Sheets

(56) References Cited

U.S. PATENT DOCUMENTS

| | | |
|---|---|---|
| 2007/0155907 A1 | 7/2007 | Zhao |
| 2007/0224241 A1 | 9/2007 | Stayton |
| 2008/0069902 A1 | 3/2008 | Zhao |
| 2008/0081075 A1 | 4/2008 | Hsiue |
| 2008/0153982 A1 | 6/2008 | Lai |
| 2008/0171067 A1 | 7/2008 | Govindan |
| 2008/0234391 A1 | 9/2008 | McCormick |
| 2008/0243049 A1 | 10/2008 | Hardy |
| 2009/0036625 A1 | 2/2009 | Chang |
| 2009/0060840 A1* | 3/2009 | Boyes ............... A61K 49/1854 424/9.1 |
| 2010/0150952 A1 | 6/2010 | Stayton |

FOREIGN PATENT DOCUMENTS

| | | |
|---|---|---|
| FR | 2 767 829 A1 | 3/1999 |
| JP | 2008-195687 A | 8/2008 |
| JP | 2008195687 A | 8/2008 |
| WO | 98/01478 A1 | 1/1998 |
| WO | 99/29303 A1 | 6/1999 |
| WO | 03/087188 A1 | 10/2003 |
| WO | 2005/061555 A1 | 7/2005 |
| WO | 2005/108614 A2 | 11/2005 |
| WO | 2006/016166 A1 | 2/2006 |
| WO | 2007/008300 A2 | 1/2007 |
| WO | 2007/109584 A1 | 9/2007 |
| WO | 2008/004978 A1 | 1/2008 |
| WO | 2008/022309 A2 | 2/2008 |
| WO | 2008/071009 A1 | 6/2008 |
| WO | 2008/085556 A2 | 7/2008 |
| WO | 2008/148174 A1 | 12/2008 |
| WO | 2008/153940 A1 | 12/2008 |
| WO | 2009/009025 A1 | 1/2009 |
| WO | 2009/021728 A2 | 2/2009 |
| WO | 2009/140421 A2 | 11/2009 |
| WO | 2009/140423 A2 | 11/2009 |
| WO | 2009/140427 A2 | 11/2009 |
| WO | 2009/140429 A2 | 11/2009 |
| WO | 2009/140432 A2 | 11/2009 |
| WO | 2010/021770 A1 | 2/2010 |
| WO | 2010/053596 A1 | 5/2010 |
| WO | 2010/053597 A2 | 5/2010 |
| WO | 2010/054266 A2 | 5/2010 |
| WO | 2010/077678 A2 | 7/2010 |
| WO | 01/87227 A2 | 11/2011 |

OTHER PUBLICATIONS

Convertine, A.J., et al., "Development of a Novel Endosomolytic Diblock Copolymer for siRNA Delivery," Journal of Controlled Release 133(3):221-229, Feb. 2009.

Dankova, M., et al., "Models for Conformationally Dynamic Metallocenes, Copolymerization Behavior of the Unbridged Metallocene (1-Methyl-2-Phenylindenyl)(2-Phenylindenyl)Zirconium Dichloride," Macromolecules 35(8):2882-2891,2002.

Dufresne, M.-H., et al., "Characterization of Polyion Complex Micelles Designed to Address the Challenges of Oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," Abstracts of Society for Biomaterials Meeting, Apr. 22, 2009, 1 page.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

El-Sayed, M.E.H., et al., "Rational Design of Composition and Activity Correlations for pH-Sensitive and Glutathione-Reactive Polymer Therapeutics," Journal of Controlled Release 101(1-3):47-58, Jan. 2005.

Extended European Search Report dated Feb. 5, 2014, issued in corresponding European Application No. 09 825 146.5, filed May 13, 2009, 9 pages.

Extended European Search Report dated Nov. 5, 2014, issued in corresponding European Application No. EP 09836724.6, filed Dec. 8, 2009, 5 pages.

Feng, X.-S., and C.-Y. Pan, "Synthesis of Amphiphilic Miktoarm ABC Star Copolymers by RAFT Mechanism Using Maleic Anhydride as Linking Agent," Macromolecules 35(13):4888-4893, 2002.

First Office Action, dated May 20, 2014, issued in corresponding Japanese Application No. 2011-540835, filed Dec. 8, 2009, 7 pages.

Fishbein, I., et al., "Local Delivery of Gene Vectors From Bare-Metal Stents by Use of a Biodegradable Synthetic Complex Inhibits In-Stent Restenosis in Rat Carotid Arteries," Circulation 117(16):2096-2103, Apr. 2008.

Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.

Gaucher, G., et al., "Block Copolymer Micelles: Preparation, Characterization and Application in Drug Delivery," Journal of Controlled Release 109(1-3):169-188, Dec. 2005.

Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.

Heredia, K.L., et al., "Reversible siRNA-Polymer Conjugates by RAFT Polymerization," Chemical Communications 28(28):3245-3247, Jul. 2008.

Hood, J.D., et al., "Tumor Regression by Targeted Gene Delivery to the Neovasculature," Science, New Series 296(5577):2404-2407, Jun. 2002.

Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.

International Search Report and Written Opinion dated Jul. 23, 2010, issued in corresponding International Application No. PCT/US2009/067193, filed Dec. 8, 2009, 12 pages.

International Search Report and Written Opinion dated Mar. 7, 2011, issued in related International Application No. PCT/US2010/056565, filed Nov. 12, 2010, 12 pages.

Invitation to Pay Additional Fees and Partial International Search Report dated Apr. 26, 2011, issued in pending International Application No. PCT/US2010/056993, filed Nov. 17, 2010, 6 pages.

Jensen, K.D., et al., "Antisense Oligonucleotides Delivered to the Lysosome Escape and Actively Inhibit the Hepatitis B Virus," Bioconjucate Chemistry 13(5):975-984, Sep.-Oct. 2002.

Jeong, J.H., et al., "siRNA Conjugate Delivery Systems," Bioconjugate Chemistry 20(1):5-14, Jan. 2009.

Jeong, Y.-I., et al., "Cellular Recognition of Paclitaxel-Loaded Polymeric Nanoparticles Composed of Poly(y-benzyl L-glutamate) and Poly(ethylene glycol) Diblock Copolymer Endcapped With Galactose Moiety," International Journal of Pharmaceutics 296(2005):151-161, Apr. 2005.

Joralemon, M.J., et al., "Synthesis, Characterization, and Bioavailability of Mannosylated Shell Cross-Linked Nanoparticles," Biomacromolecules 5(3):903-913, May-Jun. 2004.

Kabanov, A.V., et al., "Pluronic Micelles as a Tool for Low-Molecular Compound Vector Delivery Into a Cell: Effect of *Staphylococcus aureus* Enterotoxin B on Cell Loading With Micelle Incorporated Fluorescent Dye," Biochemistry International 26(6):1035-1042, May 1992.

Kataoka, K., et al., "Smart Polymeric Micelles as Nanocarriers for Oligonucleotides and siRNA Delivery," Nucleic Acids Symposium Series 49(1):17-18, Sep. 2005.

Kulkarni, S., et al, "Controlling the Aggregation of Conjugates of Streptavidin With Smart Block Copolymers Prepared Via the RAFT Copolymerization Technique," Biomacromolecules 7(10):2736-2741, Oct. 2006.

Kyriakides, T.R., et al., "pH-Sensitive Polymers That Enhance Intracellular Drug Delivery In Vivo," Journal of Controlled Release 78(1-3):295-303, Jan. 2002.

Le Garrec, D., et al., "Micelles in Anticancer Drug Delivery," American Journal of Drug Delivery 2(1):15-42, Mar. 2004.

Lee, E.S., et al., "Super pH-Sensitive Multifunctional Polymeric Micelle," Nano Letters 5(2):325-329, Feb. 2005.

Meyer, M., et al., "Synthesis and Biological Evaluation of a Bioresponsive and Endosomolytic siRNA-Polymer Conjugate," Molecular Pharmaceutics 6(3):752-762, May-Jun. 2009.

(56) References Cited

OTHER PUBLICATIONS

Murthy, N., et al., "Bioinspired pH-Responsive Polymers for the Intracellular Delivery of Biomolecular Drugs," Bioconjugate Chemistry 14(2):412-419, Mar.-Apr. 2003.
Murthy, N., et al., "The Design and Synthesis of Polymers for Eukaryotic Membrane Disruption," Journal of Controlled Release 61(1-2):137-143, Aug. 1999.
Nagasaki, Y. et al., "Sugar-Installed Block Copolymer Micelles: Their Preparation and Specific Interaction With Lectin Molecules," Biomacromolecules 2(4):1067-1070, Winter 2001.
Oishi M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.
Peppas, N.A., "Is There a Future in Glucose-Sensitive, Responsive Insulin Delivery Systems?" Drug Delivery Science and Technology 14(4):247-256, Sep. 2004.
Raso, V., "Intracellular Targeting Using Bispecific Antibodies," Methods in Molecular Medicine 25:37-49, Jan. 2000.
Read, M.L., et al., "Physicochemical and Biological Characterisation of an Antisense Oligonucleotide Targeted Against the bcl-2 mRNA Complexed With Cationic-Hydrophilic Copolymers," European Journal of Pharmaceutical Sciences 10(3):169-177, May 2000.
Sawant, R.M., et al., "'SMART' Drug Delivery Systems: Double-Targeted pH-Responsive Pharmaceutical Nanocarriers," Bioconjugate Chemistry 17:943-949, Jun. 2006.
Segura, T., and J.A. Hubbell, "Synthesis and In Vitro Characterization of an ABC Triblock Copolymer for siRNA Delivery," Bioconjugate Chemistry 18(3):736-745, May 2007.
Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.
Stayton, P.S., et al., "Intelligent Biohybrid Materials for Therapeutic and Imaging Agent Delivery," Proceedings of the IEEE 93(4):726-736, Apr. 2005.
Torchilin, V.P., "Micellar Nanocarriers: Pharmaceutical Perspectives," Pharmaceutical Research 24(1):1-16, Jan. 2007.
Turk, M.J., et al., "Characterization of a Novel pH-Sensitive Peptide That Enhances Drug Release From Folate-Targeted Liposomes at Endosomal pHs," Biochimica et Biophysics Acta 1559(1):56-68, Feb. 2002.
Varghese, O.P., et al., "In Situ Cross-Linkable High Molecular Weight Hyaluronan-Bisphosphonate Conjugate for Localized Delivery and Cell-Specific Targeting: A Hydrogel Linked Prodrug Approach," Journal of the American Chemical Society 131(25):8781-8783, Jul. 2009.
Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.
Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.
Yamamoto, S.-I., et al., "Temperature- and pH-Responsive Dense Copolymer Brushes Prepared by ATRP," Macromolecules 41(19):7013-7020, Oct. 2008.
Yasugi, K., et al., "Sugar-Installed Polymer Micelles: Synthesis and Micellization of Poly(ethylene glycol)-Poly(D,L-lactide) Block Copolymers Having Sugar Groups at the PEG Chain End," Macromolecules 32:8024-8032, Nov. 1999.
Yessine, M.-A., et al., "Proton-Actuated Membrane-Destabilizing Polyion Complex Micelles," Bioconjugate Chemistry 18(3):1010-1014, May-June.
Yoo, H.S., and T.G. Park, "Folate Receptor Targeted Biodegradable Polymeric Doxorubicin Micelles," Journal of Controlled Release 96(2):273-283, Apr. 2004.
York, A.W. et al., "Advances in the Synthesis of Amphiphilic Block Copolymers via RAFT Polymerization: Stimuli-Responsive Drug and Gene Delivery," Advanced Drug Delivery Reviews 60(9):1018-1036, Jun. 2008.
Bathfield, M., et al., "Versatile Precursors of Functional RAFT Agents. Application to the Synthesis of Bio-Related End-Functionalized Polymers," Journal of the American Chemical Society 128(8):2546-2547, Mar. 2006.
Cannon, J.G., "Analog Design," in D.J. Abraham (ed.), "Burger's Medicinal Chemistry and Drug Discovery, Sixth Edition, vol. I: Drug Discovery," Wiley, Hoboken, N.J., 2003, Chap. 16, pp. 688-714; 688.
Caulfield, M.J., and D.H. Solomon, "Studies on Polyimides: 2. Formation of High Molecular Weight Poly(N-(hydroxyphenyl) maleimides)," Polymer 40(5):1251-1260, Mar. 1999.
Cheung, C.Y., et al., "A pH-Sensitive Polymer That Enhances Cationic Lipid-Mediated Gene Transfer," Bioconjugate Chemistry 12(6):906-910, Oct. 2001.
Gondi, S.R., et al., "Versatile Pathway to Functional Telechelics via RAFT Polymerization and Click Chemistry," Macromolecules 40(3):474-481, Jan. 2007.
Hill, D.J.T., et al., "The Radical Homopolymerization of N-phenylmaleimide, N-n-hexylmaleimide and N-cyclohexylmaleimide in Tetrahydrofuran," Polymer 42(11):4791-4802, May 2001.
Hong, C.-Y., and C.-Y. Pan, "Direct Synthesis of Biotinylated Stimuli-Responsive Polymer and Diblock Copolymer by RAFT Polymerization Using Biotinylated Trithiocarbonate as RAFT Agent," Macromolecules 39(10):3517-3524, Apr. 2006.
Li, M., et al., "End Group Transformations of RAFT-Generated Polymers With Bismaleimides: Functional Telechelics and Modular Block Copolymers," Journal of Polymer Science: Part A: Polymer Chemistry 46(15):5093-5100, Aug. 2008.
York, A.W., et al., "Facile Synthetic Procedure for ω, Primary Amine Functionalization Directly in Water for Subsequent Fluorescent Labeling and Potential Bioconjugation of RAFT-Synthesized (Co)Polymers," Biomacromolecules 8(8):2337-2341, Aug. 2007.

* cited by examiner

Chemical Shift (ppm)

Chemical Shift (ppm)

Chemical Shift (ppm)

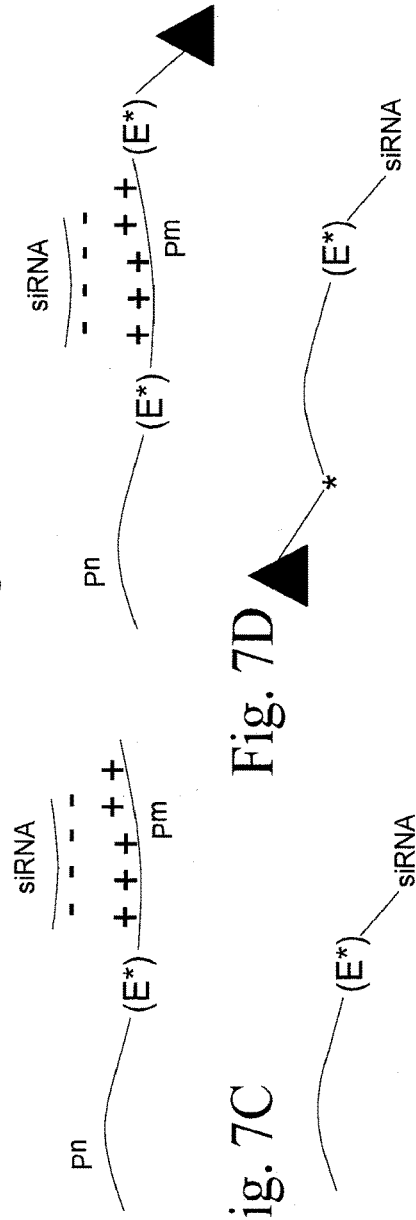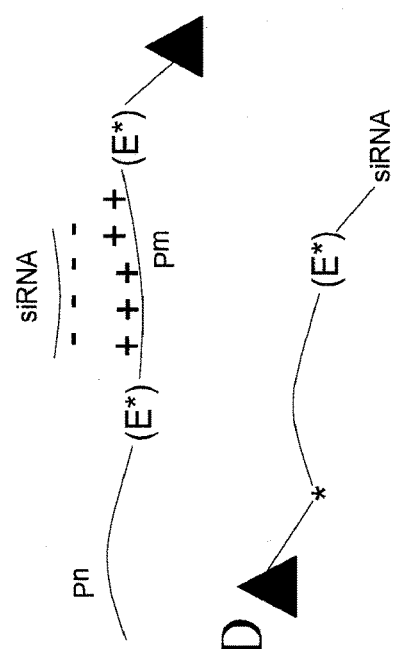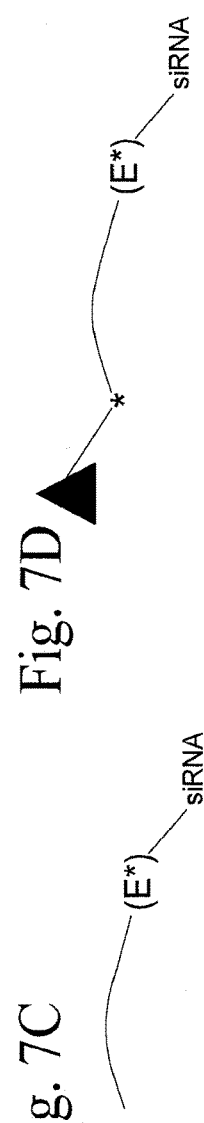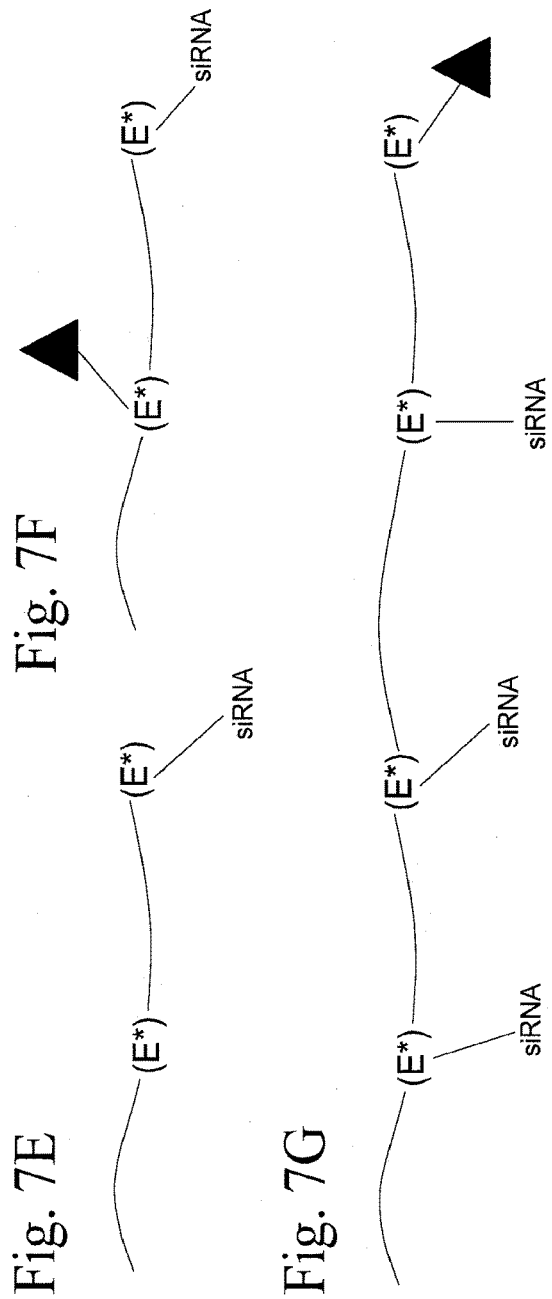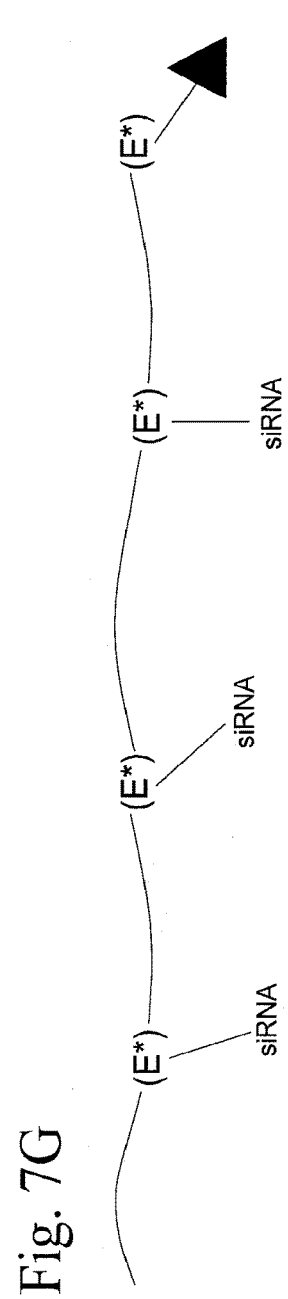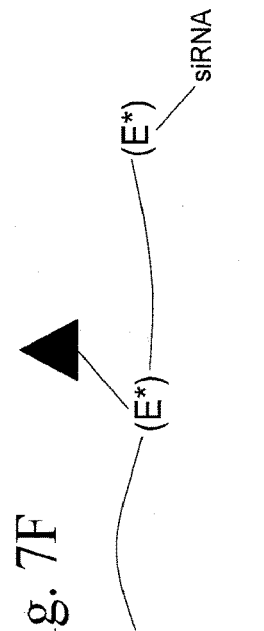

Fig. 8
[Scheme 1]
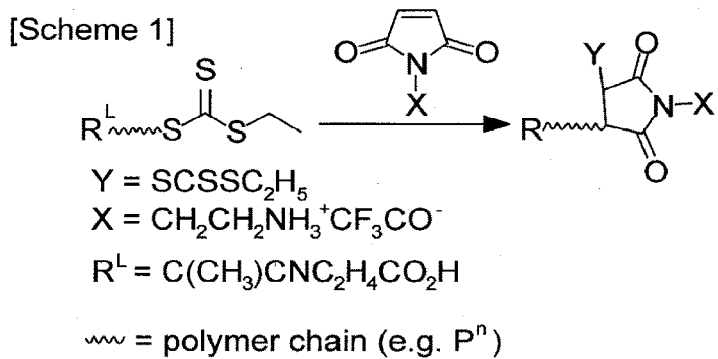
Y = SCSSC$_2$H$_5$
X = CH$_2$CH$_2$NH$_3^+$CF$_3$CO$^-$
R$^L$ = C(CH$_3$)CNC$_2$H$_4$CO$_2$H
⌇⌇⌇ = polymer chain (e.g. P$^n$)
[Scheme 2]
[2.1] *initiation*
[2.2] *reversible chain transfer/propagation*
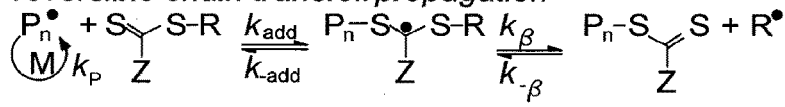
[2.3] *reinitiation*
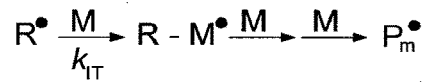
[2.4] *reversible (degenerate) chain transfer/propagation*
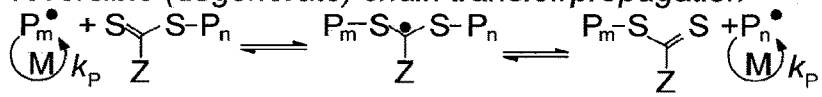
[2.5] *termination*
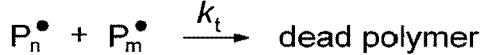
[Scheme 3]
[3.1] 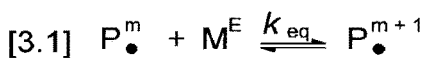
[3.2] 

ω-FUNCTIONALIZED POLYMERS, JUNCTION-FUNCTIONALIZED BLOCK COPOLYMERS, POLYMER BIOCONJUGATES, AND RADICAL CHAIN EXTENSION POLYMERIZATION

CROSS-REFERENCES TO RELATED APPLICATIONS

This application is a continuation of U.S. patent application Ser. No. 13/133,355, filed Aug. 22, 2011, which is the national stage of International Patent Application No. PCT/US2009/067193, filed Dec. 8, 2009, which claims priority from U.S. Patent Application Ser. No. 61/120,756, filed Dec. 8, 2008, the entire contents of each of which are incorporated herein by reference in their entirety.

REFERENCE TO RELATED APPLICATIONS

This application claims priority from U.S. patent application Ser. No. 61/120,756, filed Dec. 8, 2008, the entire contents of which is incorporated herein by reference in its entirety.

STATEMENT AS TO FEDERALLY SPONSORED RESEARCH

This invention was made with U.S. Government support under Contract Number R01EB002991 awarded by the National Institutes of Health. The U.S. Government has certain rights in the invention.

FIELD OF THE INVENTION

The present invention is directed to polymeric compounds and to compositions comprising polymeric compounds, including ω-functionalized polymers and junction-functionalized block copolymers and polymer conjugates. The present invention is also directed to methods involving radical chain extension polymerization suitable for preparing such compounds and compositions, and to uses of such polymeric compounds and compositions.

BACKGROUND OF THE INVENTION

Controlled (living) radical polymerization approaches such as nitroxide-mediated polymerization (NMP)(1), atom transfer radical polymerization (ATRP)(2), and reversible addition-fragmentation chain transfer polymerization (RAFT)(3, 4) are known in the art for preparing polymers having relatively narrow molecular weight distributions and advanced architectures. Polymers can be derived from diverse monomers via RAFT polymerization in both organic and aqueous conditions (5-11). Polymers derived from such radical polymerization approaches can be telechelic polymers—with distinct α and ω functionalities. Polymer conjugates have been prepared from telechelic polymers via coupling to various moieties of interest (12-17).

Approaches for preparing end-functionalized polymers are known. For example, polymers having functionalized end groups have been prepared using ATRP by modifying the initiator (18, 19), or using RAFT by modifying the chain transfer agent (CTA). For example, RAFT CTA's are known with functional leaving groups, $R^L$ (16, 17, 20-23), or alternatively with functional activating groups, Z (24, 25). Post-polymerization functionalization of polymers is also known. For example, polymers prepared by radical polymerization using RAFT CTAs based on xanthates, dithioesters, dithiocarbamates and trithiocarbonates, can be reduced with primary amines (26-28) or $NaBH_4$ (12, 13) to result in a thiol end group. Although conjugation to thiols have been described (11, 13, 14, 26, 29-35) such reactions typically involve undesirable reaction conditions. U.S. Pat. No. 6,919,409 to Charmot et al. discloses ω-functionalization of RAFT polymers by chain extension with functionalized monomers; however, the disclosed approach includes cleavage of the thiocarbonylthio control transfer agent, thereby precluding further CTA-mediated radical polymerization, and thus limiting polymer architecture flexibility. Generally known approaches for preparing end-functional RAFT polymers are also limited with respect to certain functional groups such as amine functional groups. Moad et al., report for example that polymers with primary or secondary amine functionality cannot be prepared directly by RAFT polymerization, because these groups undergo facile reaction with thiocarbonylthio compounds. (See Moad et al., The Chemistry of Radical Polymerization, 2d Ed., p. 538-540 Elsevier (2006); See also WO 1998/001478). Indirect approaches using RAFT agents with latent (protected) amine functionality are known. (Id.)

Further approaches for preparing functionalized polymers such as ω-functionalized RAFT polymers are needed which overcome the various shortcomings of existing approaches.

SUMMARY OF THE INVENTION

Polymeric compounds having spatially controlled bioconjugation sites are effected through selective functionalization involving ω-terminal chain extension of polymer chains by radical polymerization, such as reversible addition-fragmentation chain transfer (RAFT) polymerization.

Polymeric compounds of the invention comprise ω-functionalized polymer chains, in which the ω-functionalization is effected by incorporation of chain extension monomers having one or more functional groups. Hence, polymeric compounds of the invention comprise at least one polymer chain and an associated ω-terminal chain extension moiety, where such chain extension moiety comprises one or more chain extension residues (e.g., monomeric residue(s) derived from radical chain-extension polymerization of the chain extension monomer). The chain extension monomer(s), and the corresponding chain extension residue(s) can include one or more reactive functional groups (optionally protected or masked by one or more labile protecting or masking groups). Improved approaches for preparing such polymeric compounds involve chain extension of a polymer chain, P'', via reversible addition-fragmentation chain transfer (RAFT) polymerization to form a chain extension moiety (E*) at the ω-end of the polymer chain, in which:

(i) the extent incorporation of chain-extension monomers is limited—such that the resulting chain extension moiety comprises a limited number (e.g., not more than 20, preferably not more than 10, e.g., ranging from 1 to 10) of chain extension residues, E;

(ii) one or more of the chain-extension residues includes a functional group, and preferably a reactive amine-functional group; and/or (iii) the ω-terminal end of the chain-extension moiety includes a chain transfer moiety, —Y, where the chain transfer moiety can be operable for further RAFT polymerization (i.e., has a living character), or alternatively, where the chain transfer moiety can be cleaved or derivatized post-polymerization.

In preferred embodiments of the various aspects of the invention, the combination of the aforementioned attributes can include the attribute of (i) limited chain extension, where the chain extension moiety (E*) comprises only the limited number of chain extension residues, E, and preferably is derived from reversible addition-fragmentation chain transfer (RAFT) chain extension reaction using a non-homopolymerizable monomer, as further described below, such attribute being combined with at least one of, and preferably both of the attributes of: (ii) chain extension using monomers which include functional groups such as amine functional groups; and (iii) chain extension which results in inclusion and viability of a chain transfer residue which is operable as living chain transfer moiety—effectively providing a macromolecular chain transfer agent (macro-CTA).

Advantageously, such approaches allow for the preparation of polymer chains which can be selectively functionalized at the ω-terminal end thereof. The living character of the chain transfer moiety at the ω-end allows for further radical polymerization to prepare block copolymers which are junction-functionalized, and optionally also ω-end functionalized. The approach can be effected with various chain extension monomers, including monomers (e.g., N-substituted maleimides) that can accommodate a variety of reactive functional groups (e.g., amine functional groups). The availability and versatility of such reactive functional groups provides opportunities for effective bioconjugation, and thereby affords polymer conjugates such as polymer bioconjugates, with a (bio)conjugate moiety linked to the polymer chain through one or more chain extension residues. The universality and substantial flexibility of RAFT radical polymerization further enhances the applications of such approaches. Hence, among the aspects of the invention disclosed and claimed herein are polymeric compounds such as functionalized polymers and polymer (bio)conjugates with substantial architectural diversity.

Generally, therefore, among the aspects of the invention are polymeric compounds. The polymeric compounds one or more polymer chains and one or more chain extension moieties. Preferably, the polymeric compounds include ω-functionalized polymers, and junction-functionalized block copolymers. Block copolymers can include both junction-functionalized and/or ω-functionalized block copolymers. The polymeric compounds can include amine-functional polymeric compounds. The polymeric compounds can include macromolecular chain transfer agents (macro-CTA's), including ω-functionalized macro-CTA's for radical polymerization. The polymeric compounds include polymer conjugates. The polymeric compounds can include ω-conjugated polymer conjugates and junction-conjugated block copolymer conjugates. Block copolymer conjugates can include both junction-conjugated and/or ω-conjugated block copolymer conjugates. The polymeric compounds can include biopolymer conjugates, such as polynucleotide-polymer conjugates.

The present invention is directed in a first aspect to compounds comprising polymeric compounds.

In a first general embodiment of the first aspect of the invention, polymeric compounds of the invention can include polymer compounds which comprise a polymer having a formula IIA $$P''\text{-}(E)_k\text{-}[Y,Y^* \text{ or } P'''] \quad \text{(IIA)},$$

where P'' is a first polymer chain (preferably derived from radical polymerization), E is an independently selected chain extension residue, k is an integer ranging from 1 to 20, preferably ranging from 1 to 10, Y is a chain transfer agent residue, preferably a reversible addition-fragmentation chain transfer (RAFT) residue, for example and preferably a thiocarbonylthio moiety having a formula —SC(=S)Z, where Z is an activating group, Y* is a chain transfer residue derivative, for example and preferably a moiety derived from cleavage of or derivatization of (e.g., functionalization of) the thiocarbonylthio moiety, Y, and P''' is a second polymer chain (preferably derived from radical polymerization).

In a second general embodiment of the first aspect of the invention, polymeric compounds of the invention can include polymer bioconjugate compounds which comprise a polymer having a Formula IIA (as described above), where one or more E is a chain extension residue comprising one or more bioconjugate moieties, Q, covalently linked thereto, e.g., through a linking moiety, L. Generally, such polymeric compounds can include polymer (bio)conjugate compounds which comprise a polymer having a formula IA:

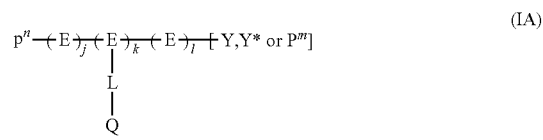
(IA)

wherein P'' is a first polymer chain (preferably derived from radical polymerization), E is an independently selected chain extension residue, j, k and l are each independently selected integers, where j ranges from 0 to 9, k is ≥1, l ranges from 0 to 9, and the sum j+k+l is ≤20, and preferably, the sum (j+k+l) is ≤10, L is a linking moiety, Q is a biomolecular agent (e.g., such as a polynucleotide) covalently bonded to E through L, and each of Y, Y* and P''' are as described above in connection with the first general embodiment of the first aspect of the invention. The biomolecular agent is a biologically relevant moiety, preferably selected from a therapeutic agent, a targeting agent, a diagnostic agent and an analytical agent.

In a third general embodiment of the first aspect of the invention, the polymeric compounds of the invention include the polymeric compounds of Formula IA and Formula IIA as described above, where the chain extension residue, E comprises one or more functional groups, and preferably E comprises a reactive amine functional group (e.g., a primary amine or a secondary amine) or a corresponding ammonium salt thereof.

In a fourth general embodiment of the first aspect of the invention, polymeric compounds of the invention include the polymeric compounds of Formula IA and Formula IIA as described above, where the polymeric compound comprises a chain transfer agent residue, Y. Preferably, such a polymeric compound can be a macromolecular chain transfer agent—a macro-CTA—e.g., where Y is capable of further reversible addition-fragmentation chain transfer (RAFT) polymerization (e.g., have a living character), and preferably in substantially isolated form. Preferably, the polymeric compound can be a macromolecular chain transfer agent in substantially isolated form having a formula IIIA, $$P''\text{-}(E)_k\text{-}Y \quad \text{(IIIA)},$$

where each of P'', E, k and Y is as described above in connection with Formula IIA or Formula IA (e.g., including where E is a chain extension residue comprising one or more bioconjugate moieties, Q, covalently linked thereto, e.g., through a linking moiety, L).

In a fifth general embodiment of the first aspect of the invention, polymeric compounds of the invention include the polymeric compounds of Formula IA and Formula IIA as described above, where the polymeric compound comprises a block copolymer comprising two or more polymer blocks (e.g., discrete polymer chains), typically separated by one or more chain extension moieties, (E*). Generally, the polymeric compounds of the invention can comprise an A-(E*)-B block copolymer or an A-(E*)-B block copolymer conjugate, comprising a first block A of the copolymer defined by the first polymer chain, P″, and a second block B of the copolymer defined by the second polymer chain, P‴, and a chain extension moiety (E*) comprising one or more chain extension residue(s), E. Preferably, the second block B can be different from (e.g., have a different chemical composition or different arrangement of atoms and/or different physical properties from) the first block A. Preferably, such a polymeric compound can be an A-(E*)-B block copolymer having a formula IVA $$P''\text{-}(E)_k\text{-}P'''  \quad\quad (IVA),$$

where each of P″, E, k and P‴ is as described above in connection with Formula IIA or Formula IA (e.g., including where E is a chain extension residue comprising one or more bioconjugate moieties, Q, covalently linked thereto, e.g., through a linking moiety, L).

In a sixth general embodiment of the first aspect of the invention, polymeric compounds of the invention include the polymeric compounds of Formula IA and Formula IIA as described above, where the polymeric compound comprises a polymer compound wherein the chain extension moiety (E*) consists of one chain extension residue, E. Preferably, such chain extension moiety (E*) comprising a singular chain extension residue, E, is derived from reversible addition-fragmentation chain transfer (RAFT) chain extension reaction using a non-homopolymerizable monomer, as further described below. Generally, the polymeric compounds of the invention can comprise a polymer having a formula VA $$P''\text{-}E\text{-}[Y \text{ or } Y^*] \quad\quad (VA),$$

where each of P″, E, Y and Y* is as described above in connection with Formula IIA or Formula IA (e.g., including where E is a chain extension residue comprising one or more bioconjugate moieties, Q, covalently linked thereto, e.g., through a linking moiety, L).

In a seventh general embodiment of the first aspect of the invention, polymeric compounds of the invention include polymeric compounds prepared by a methods which includes the methods of the fourth aspect of the invention (described below), including any general embodiments thereof (and including all subembodiments thereof).

The present invention is directed in a second aspect to compositions comprising polymeric compounds.

In a first general embodiment of the second aspect of the invention, the compositions comprise polymeric compounds of the first aspect of the invention, including any of the general embodiments of the first aspect, and any subembodiments thereof.

In a second general embodiment of the second aspect of the invention, the compositions can comprise a polymeric compound comprising a polymer having a formula IIA $$P''\text{-}(E)_k\text{-}[Y,Y^* \text{ or } P'''] \quad\quad (IIA),$$

in an amount of at least about 30%, preferably at least about 40%, preferably at least about 50% by weight (relative to total weight of the composition), where each of P″, E, k, Y, Y* and P‴ is as described above in connection with Formula IIA or Formula IA (e.g., including where E is a chain extension residue comprising one or more bioconjugate moieties, Q, covalently linked thereto, e.g., through a linking moiety, L), or as described above in connection with each of the various the general embodiments of the first aspect, and any subembodiments thereof.

In a third general embodiment of the second aspect of the invention, the compositions can include polynucleotide-containing compositions, where such compositions include a polymeric compound and a polynucleotide associated therewith, where the polymeric compound is a polymer compound or a polymer (bio)conjugate of the first aspect of the invention (including any of the general embodiments of the first aspect, and any subembodiments thereof).

In a fourth general embodiment of the second aspect of the invention, the compositions can include polynucleotide-containing compositions, where such compositions comprise a polymeric compound and a polynucleotide associated therewith, the polymeric compound comprising a polymer having a formula IIA $$P''\text{-}(E)_k\text{-}[Y,Y^* \text{ or } P'''] \quad\quad (IIA),$$

where each of P″, E, k, Y, Y* and P‴ is as described above in connection with Formula IIA or Formula IA (e.g., including where E is a chain extension residue comprising one or more bioconjugate moieties, Q, covalently linked thereto, e.g., through a linking moiety, L), or as described above in connection with each of the various the general embodiments of the first aspect, and any subembodiments thereof.

Generally with regard to either of the third or fourth general embodiments of the second aspect of the invention (including any subembodiments thereof), the polynucleotide can be covalently linked to the polymeric compound (e.g., covalently bonded to a chain extension residue, E, of one or more of the chain extension moieties, (E*), in each case through an independently selected linking moiety, L), or alternatively can be associated with the polymeric compounds through non-covalent interactions with the polymeric compound (e.g., through ionic interactions therewith). Generally in this regard, the polymeric compounds of such compositions can preferably comprise at least one membrane disruptive polymer chain (e.g., a pH sensitive polymer having membrane disrupting activity at endosomal pH). Generally in this regard, the polymeric compounds of such compositions can preferably comprise at least polymer chain which is hydrophobic. Generally in this regard, the polymeric compounds of such compositions can preferably comprise at least one polymer chain which includes a plurality of monomeric residues having a first chargeable species, the first chargeable species being anionic at serum physiological pH, and being substantially neutral or non-charged at an endosomal pH. Generally in this regard, the polymeric compounds of such compositions can preferably comprise a block copolymer, the block copolymer comprising a first membrane disruptive polymer chain defining a first block A of the copolymer, and a second polymer chain defining a second block B of the copolymer. Generally in this regard, the polymeric compounds of such compositions can preferably comprise a block copolymer, the block copolymer comprising a first hydrophobic polymer chain defining a first block A of the copolymer and which includes a plurality of monomeric residues having a first chargeable species, the first chargeable species being anionic at serum physiological pH, and being substantially neutral or non-charged at an endosomal pH, and a second polymer chain defining a second block B of the copolymer. Generally, in the regard of block copolymer embodiments, the block copolymer can comprise a second polymer chain defining a second block B of the copolymer which includes a plurality of monomeric residues having a cationic species at serum physiological pH, wherein the polynucleotide is associated with the block copolymer through non-covalent interactions between the polynucleotide and the cationic species of the second block B of the copolymer. Generally in this regard, the polymeric compounds of such compositions can comprise one or more targeting moieties covalently bonded to the polymeric compounds (e.g., covalently bonded to a chain extension residue E of one or more of the chain extension moieties, (E*), in each case through an independently selected linking moiety, L). Generally, in this regard, such targeting moiety can be a ligand having affinity for one or more receptors effective for mediating endocytosis. Each of the aforementioned general features of the third or fourth general embodiment of the second aspect of the invention can be used in various combinations and permutations, and are expressly contemplated in each possible combination and permutations.

The present invention is directed in a third aspect to pharmaceutical compositions comprising polymeric compounds.

In a first general embodiment of the third aspect of the invention, the pharmaceutical compositions comprise polymeric compounds of the first aspect of the invention, including any of the general embodiments of the first aspect (and any subembodiments thereof), and one or more pharmaceutically acceptable excipients.

In a second general embodiment of the third aspect of the invention, the pharmaceutical compositions comprise compositions of the second aspect of the invention, including any of the general embodiments of the second aspect (and any subembodiments thereof), and further comprise one or more pharmaceutically acceptable excipients.

In a third general embodiment of the third aspect of the invention, the pharmaceutical compositions comprise a polymeric compound comprising a polymer having a formula IIA

P''-(E)$_k$-[Y,Y* or P''']          (IIA), and a pharmaceutically acceptable excipient, where each of P'', E, k, Y, Y* and P''' is as described above in connection with Formula IIA or Formula IA (e.g., including where E is a chain extension residue comprising one or more bioconjugate moieties, Q, covalently linked thereto, e.g., through a linking moiety, L), or as described above in connection with each of the various the general embodiments of the first aspect, and any subembodiments thereof.

The present invention is directed in a fourth aspect to methods for preparing a polymeric compound.

In a first general embodiment of the fourth aspect, the invention involves preparing polymeric compounds of the first aspect of the invention, including any of the general embodiments of the first aspect (and any subembodiments thereof), by a method which includes radical polymerization, and preferably involves reversible addition-fragmentation chain transfer (RAFT) polymerization. Generally in this regard, the chain extension moiety (E*) is prepared using radical chain extension polymerization, and preferably involves reversible addition-fragmentation chain transfer (RAFT) polymerization. Preferably, for example, the polymeric compounds can be prepared by a radical polymerization method which comprises (i) reacting a first set A of one or more monomers in the presence of an activated radical and a chain transfer agent comprising a thio-cabonyl-thio moiety under polymerization conditions to form a macromolecular chain transfer agent having a formula P''—Y where Y is SC(=S)Z, and Z is activating group, and (ii) subsequently reacting a chain extension monomer, E, in the presence of an activated radical and the macromolecular chain transfer agent under chain extension conditions to form a chain-extension adduct having a formula P''-(E)$_k$-Y, where k is an integer ranging from 1 to 10.

In a second general embodiment of the fourth aspect, the invention includes preparing a polymeric compound by radical polymerization, including (i) reacting one or more monomers in the presence of an activated radical and a chain transfer agent comprising a thio-cabonyl-thio moiety under polymerization conditions to form a macromolecular chain transfer agent having a formula P''—Y where Y is SC(=S)Z, and Z is activating group, the macromolecular chain transfer agent having a polydispersity index, Mw/Mn, of less than 1.5, and (ii) subsequently, reacting a chain extension monomer, E, in the presence of an activated radical and the macromolecular chain transfer agent under chain extension conditions to form a chain-extension adduct having a formula P''-(E)$_k$-Y, where k is an integer ranging from 1 to 10, the chain-extension adduct having a polydispersity index, Mw/Mn, of less than 1.5, and where the polydispersity index of the chain-extension adduct, P''-(E)$_k$-Y, differs from the polydispersity index of the macromolecular chain transfer agent, P''—Y, by not more than 10%.

In a third general embodiment of the fourth aspect, the invention includes preparing an A-(E*)-B polymer by radical polymerization, the method comprising (i) reacting a first set A of one or more monomers in the presence of an activated radical and a chain transfer agent comprising a thio-cabonyl-thio moiety under polymerization conditions to form a macromolecular chain transfer agent having a formula P''—Y where Y is SC(=S)Z, and Z is activating group, (ii) reacting a chain extension monomer, E, in the presence of an activated radical and the macromolecular chain transfer agent under chain extension conditions to form a chain-extension adduct having a formula P''-(E)$_k$-Y, where k is an integer ranging from 1 to 10, and (iii) reacting a second set B of one or more monomers in the presence of an activated radical and the chain-extension adduct under polymerization conditions to form an A-E-B polymer having a formula P''-(E)$_k$-Pm—Y, the second set B of one or more monomers being the same as or different from the first set A of one or more monomers.

The present invention is directed in a fifth aspect to methods of using such polymeric compounds and compositions.

In a first general embodiment of the fifth aspect, the polymeric compounds or compositions of the first, second or third aspects of the invention are used as diagnostic agents.

In a second general embodiment of the fifth aspect, the polymeric compounds or compositions of the first, second or third aspects of the invention are used as therapeutic agents.

In a third general embodiment of the fifth aspect, the polymeric compounds or compositions of the first, second or third aspects of the invention are used as analytical agents.

In a fourth general embodiment of the fifth aspect, the polymeric compounds or compositions of the first, second or third aspects of the invention (e.g., polynucleotide-polymer conjugates and the polynucleotide-containing compositions) can be used for intracellular delivery of polynucleotides such as interfering RNAi (e.g., small interfering RNA (siRNA). Generally, in this regard, the cells can be in-vitro cell. Generally in this regard, the cells can be in-vivo cells.

Various features of the invention, including features defining each of the various aspects of the invention, including all general embodiments thereof, and any subembodiments thereof, can be used in various combinations and permutations with other features of the invention. Features and advantages are described herein, and will be apparent from the following Detailed Description.

BRIEF DESCRIPTION OF THE DRAWINGS

FIG. 1 (A-D) illustrates various schematic representations of polymeric compounds of the invention.

FIG. 7 (A-G) illustrates various schematic representations of polymeric compounds of the invention including polymer compounds adapted for non-covalent association with polynucleotides (e.g., siRNA) via interactions comprising ionic interactions (FIGS. 7A, 7B), and including polymer compounds adapted for covalent bioconjugation with polynucleotides (e.g., siRNA) through one or more extension moieties (E*) at the ω-end thereof (FIGS. 7C, 7D, 7E, 7F). In each case the polymeric compound can further comprise one or more targeting moieties (represented by a triangle) (e.g., a ligand effective for mediating receptor-mediated endocytosis) (FIGS. 7B, 7D, 7F, 7G). In some embodiments the polymeric compound comprises a plurality of polymer chains, a plurality of chain extension moieties, and/or a plurality of bioconjugate moieties linked to the chain extension moieties, and optionally one or more a targeting moiety (FIGS. 7E, 7F, 7G).

FIG. 8 illustrates various reaction schema, including (i) an example of a synthetic pathway for maleimido chain extension polymerization using a trithiocarbonate chain transfer agent (Scheme 1), (ii) a set of sequences which include addition-fragmentation equilibria which are characteristic of reversible addition-fragmentation chain transfer (RAFT) polymerization, as described in Moad et al., The Chemistry of Radical Polymerization, 2d Ed., p. 503-505, Elsevier (2006) (Scheme 2), and sequences schematically representing the addition of propagating polymer radicals (e.g., $P^n$., $P^m$.) to chain extension monomers (e.g., $M^E$) in a RAFT chain-extension polymerization (Scheme 3).

Figure 1A:
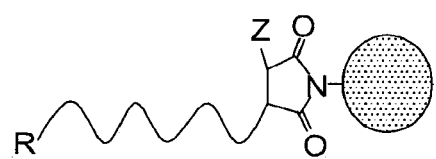
FIGS. 1A and 1B illustrate a schematic representation of telechelic polymeric compounds (e.g., derived from RAFT polymerization), including polymer bioconjugates comprising a polymer chain, a chain extension moiety (shown comprising a maleimide chain extension residue), and a biomolecular agent (shown as solid oval shape) covalently linked thereto, where the chain extension moiety is at the ω-terminal end of the polymeric compound (FIG. 1A), or at a junction between a first block A and a second block B of the polymeric compound (FIG. 1B). In the depicted embodiments, the —$R^L$ moiety as shown in FIGS. 1A and 1B can be a chain transfer agent leaving group, $R^L$ (e.g., a carboxylate group), and the —Y moiety as shown in FIGS. 1A and 1B can be a chain transfer residue, Y (e.g., a trithiocarbonate), or alternatively (not shown) a derivative thereof, Y* (e.g., a thiol).

Various aspects of the figures are described in further detail below, in connection with the Detailed Description of the Invention.

DETAILED DESCRIPTION OF THE INVENTION

Polymeric compounds having spatially controlled bioconjugation sites are described in detail herein. Such compounds are realized using selective ω-terminal chain extension of polymer chains by radical polymerization, such as reversible addition-fragmentation chain transfer (RAFT) polymerization.

Polymeric compounds of the invention comprise ω-functionalized polymer chains, in which the ω-functionalization is effected by incorporation of chain extension monomers having one or more functional groups. Hence, polymeric compounds of the invention comprise at least one polymer chain and an associated ω-terminal chain extension moiety, where such chain extension moiety comprises one or more chain extension residues (e.g., monomeric residue(s) derived from radical chain-extension polymerization of the chain extension monomer). The chain extension monomer(s), and the corresponding chain extension residue(s) can include one or more reactive functional groups (optionally protected by one or more labile protecting groups). Improved approaches for preparing such polymeric compounds involve chain extension of a polymer chain, $P^n$, via reversible addition-fragmentation chain transfer (RAFT) polymerization to form a chain extension moiety (E*) at the ω-end of the polymer chain, in which:

(i) the extent incorporation of chain-extension monomers is limited—such that the resulting chain extension moiety comprises a limited number (e.g., not more than 20, preferably not more than 10, e.g., ranging from 1 to 10) of chain extension residues, E;

(ii) one or more of the chain-extension residues includes a functional group, and preferably a reactive amine-functional group; and/or (iii) the ω-terminal end of the chain-extension moiety includes a chain transfer moiety, —Y, where the chain transfer moiety can be operable for further RAFT polymerization (i.e., has a living character), or alternatively, where the chain transfer moiety can be cleaved or derivatized post-polymerization.

In preferred embodiments of the various aspects of the invention, the combination of the aforementioned attributes can include the attribute of (i) limited chain extension, where the chain extension moiety (E*) comprises only the limited number of chain extension residues, E, and preferably is derived from reversible addition-fragmentation chain transfer (RAFT) chain extension reaction using a non-homopolymerizable monomer, as further described below, such attribute being combined with at least one of, and preferably both of the attributes of: (ii) chain extension using monomers which include functional groups such as amine functional groups; and (iii) chain extension which results in inclusion and viability of a chain transfer residue which is operable as living chain transfer moiety—effectively providing a macromolecular chain transfer agent (macro-CTA).

Polymeric Compounds

In the various aspects of the invention disclosed or claimed herein (including each aspect of the invention and each general embodiment thereof) the compounds of the invention (or compositions including such compounds) can comprise a polymeric compound. The polymeric compound can be a polymer compound or a polymer conjugate.

Figure 1B:
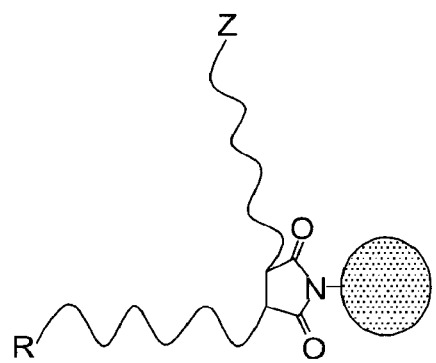

With reference to FIG. 1A for example, the polymeric compound can comprise a polymer bioconjugate comprising a polymer chain, a chain extension moiety (shown comprising a singular maleimide chain extension residue) at the ω-terminal end of the polymer chain, and a biomolecular agent (shown as solid oval shape) covalently linked to the chain extension moiety. As shown, a chain transfer moiety, —Y, can be coupled to the chain extension residue and be capable of further radical polymerization. As shown, the α-end of the polymer chain can comprise for example a leaving group, —$R^L$, derived from the RAFT chain transfer agent. Such leaving group, —$R^L$, can optionally also be functionalized (e.g., can comprise one or more functional groups such as a carboxylate group), as is known in the art. In FIG. 1B for example, the polymeric compound can comprise a block copolymer bioconjugate comprising a first polymer chain defining a first block A, a chain extension moiety (shown comprising a singular maleimide chain extension residue) at the ω-end of the first polymer chain, a biomolecular agent (shown as solid oval shape) covalently linked to the chain extension moiety, and a second polymer chain covalently bonded to the chain extension moiety and defining a second block B of the block copolymer. As shown, a chain transfer moiety, —Y, can be coupled to ω-end of the second polymer chain, and can be capable of further radical polymerization. As shown, the α-end of the first polymer chain can comprise for example a leaving group, —$R^L$, derived from the RAFT chain transfer agent. Such leaving group, —$R^L$, can optionally also be functionalized, as known in the art.

Figure 1C:
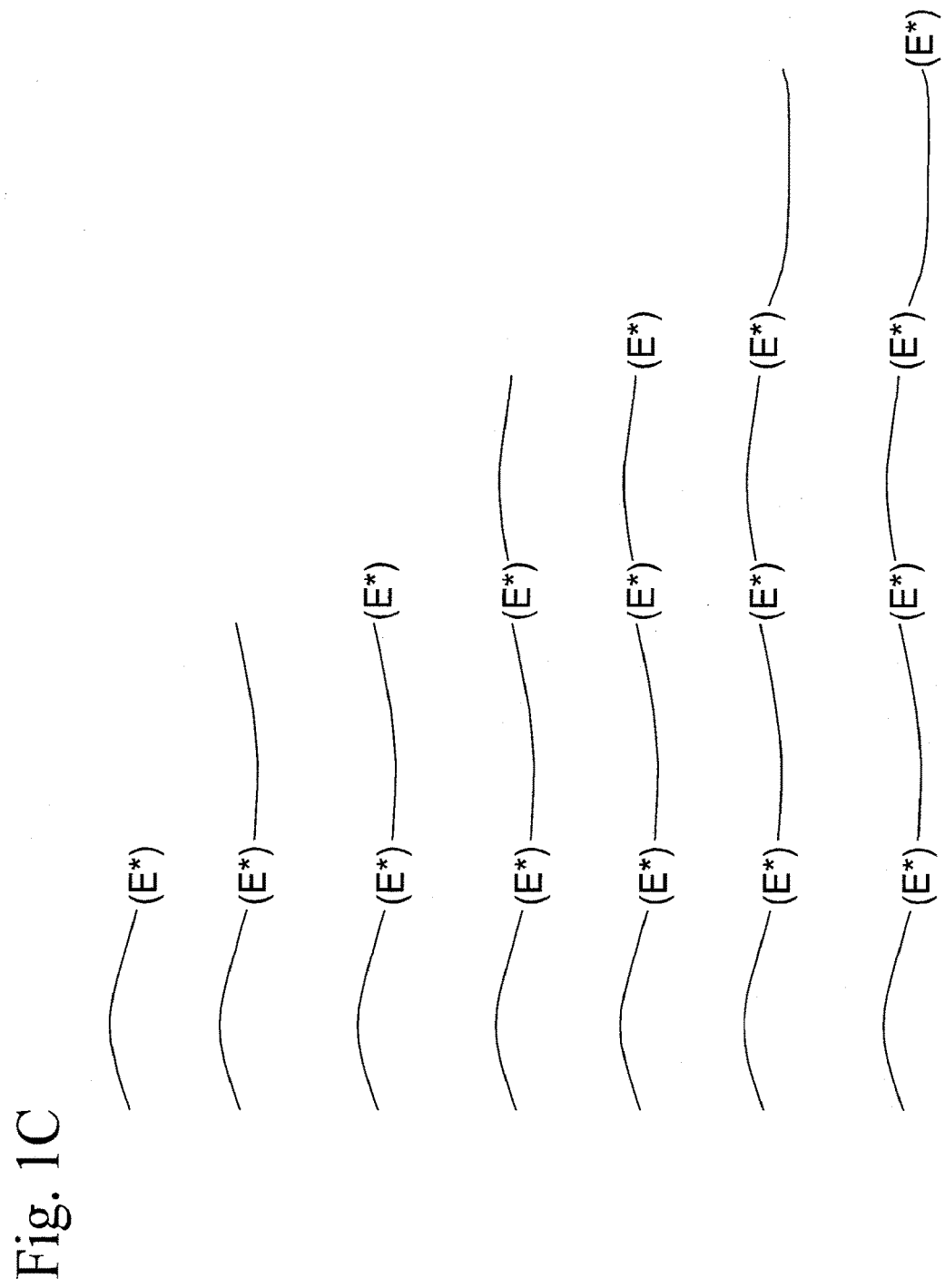
FIG. 1C illustrates a representative schematic of various polymeric compounds (e.g., derived from RAFT polymerization), each including one or more polymer chains and one or more chain extension moieties (E*) at the ω-terminal end of the polymeric compound and/or at one or more junctions between polymer chains. In the depicted embodiments, each polymer chain can be a block of a block copolymer compound.
Figure 1D:
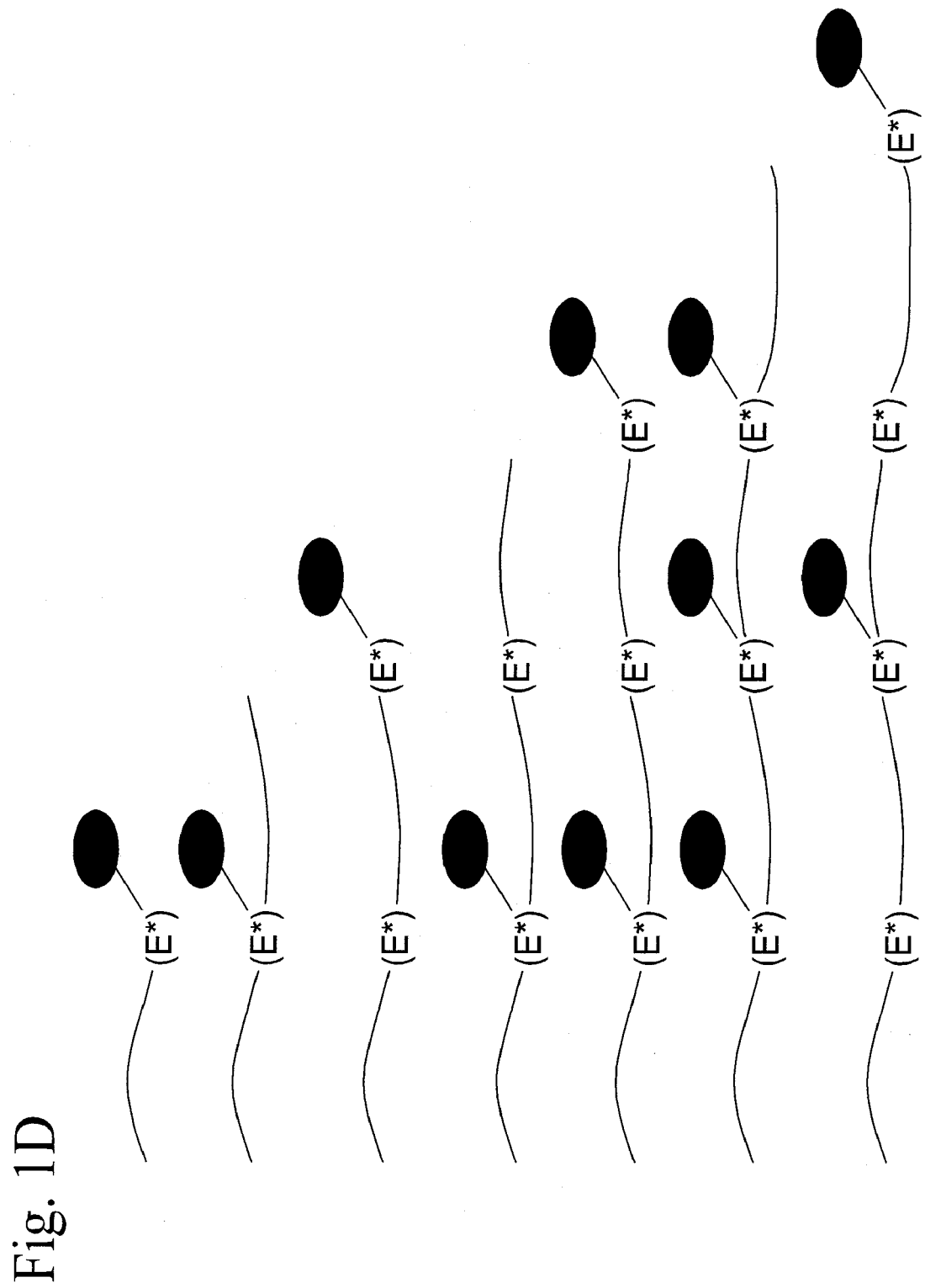
FIG. 1D illustrates a representative schematic of various polymeric compounds (e.g., derived from RAFT polymerization) including polymer bioconjugates, each including one or more polymer chains, one or more chain extension moieties (E*) at the ω-terminal end of the polymeric compound and/or at one or more junctions between polymer chains, and one or more bioconjugate moieties, Q (shown as an oval shape), each covalently linked to a chain extension moiety. In the depicted embodiments, each polymer chain can be a block of a block copolymer bioconjugate compound.

The invention can include polymeric compounds with various polymer properties and polymer architectures, including with respect to the polymer chains (e.g., chemical nature, physical properties, macrostructural architecture, etc.) and with respect to arrangement of chain extension moieties (E*) (e.g., chemical nature, number, location, spatial density, etc.). With reference to FIG. 1C, for example, various polymeric compounds can include one or more polymer chains and one or more chain extension moieties (E*) at the ω-terminal end of the polymeric compound and/or at one or more junctions between polymer chains. In the depicted embodiments, each polymer chain can be considered as a block of a block copolymer compound. In FIG. 1D various polymeric compounds are polymer bioconjugates, each including one or more polymer chains, one or more chain extension moieties (E*) at the ω-terminal end of the polymeric compound and/or at one or more junctions between polymer chains, and one or more bioconjugate moieties, Q (shown as an oval shape), each covalently linked to a chain extension moiety. In the depicted embodiments, each polymer chain can be considered as a block of a block copolymer bioconjugate compound. Although represented in FIGS. 1C and 1D as linear polymeric compounds, the polymeric compounds of the invention can also include branched polymeric, crosslinked polymeric, star polymeric, or other macromolecular structures. Advantageously, and as discussed in further detail below, the polymeric compounds of the present invention can include the many various architectural structures known in the art in connection with polymers derived from controlled (living) radical polymerization approaches, such as RAFT polymerization.

Generally, therefore, polymeric compounds of the invention can include polymer compounds which comprise a polymer having a formula IIA

$$P^n\text{-}(E)_k\text{-}[Y, Y^* \text{ or } P^m] \qquad (\text{IIA}),$$

wherein $P^n$ is a first polymer chain (preferably derived from radical polymerization), E is an independently selected chain extension residue, k is an integer ranging from 1 to 20, preferably ranging from 1 to 10, Y is a chain transfer agent residue, preferably a reversible addition-fragmentation chain transfer (RAFT) residue, for example and preferably a thiocarbonylthio moiety having a formula —SC(=S)Z, where Z is an activating group, Y* is a chain transfer residue derivative, for example and preferably a moiety derived from cleavage of or derivatization of (e.g., functionalization of) the thiocarbonylthio moiety, Y, and $P^m$ is a second polymer chain (preferably derived from radical polymerization).

Generally, polymeric compounds of the invention can include polymer bioconjugate compounds which comprise a polymer having a Formula IIA (as described above), where one or more E is a chain extension residue comprising one or more bioconjugate moieties, Q, covalently linked thereto, e.g., through a linking moiety, L. Generally, such polymeric compounds can include polymer (bio)conjugate compounds which comprise a polymer having a formula IA:

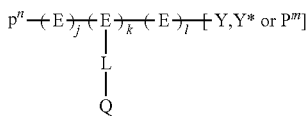  (IA)

wherein $P''$ is a first polymer chain (preferably derived from radical polymerization), E is an independently selected chain extension residue, j, k and l are each independently selected integers, where j ranges from 0 to 9, k is $\geq 1$, l ranges from 0 to 9, and the sum (j+k+l) is $\leq 20$, and preferably, the sum (j+k+l) is $\leq 10$, L is a linking moiety, Q is a biomolecular agent covalently bonded to E through L, Y is a chain transfer agent residue, preferably a reversible addition-fragmentation chain transfer (RAFT) residue, for example and preferably a thiocarbonylthio moiety having a formula —SC(=S)Z, where Z is an activating group, Y* is a chain transfer residue derivative, for example and preferably a moiety derived from cleavage of or derivatization of (e.g., functionalization of) the thiocarbonylthio moiety, Y, and $P'''$ is a second polymer chain (preferably derived from radical polymerization).

In preferred embodiments, E is a chain extension residue of Formula E1,

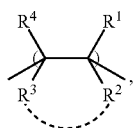  (E1)

and the polymer (bio)conjugate can preferably comprise a polymer of Formula IB,

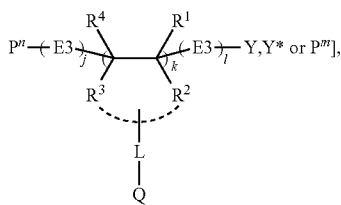  (IB)

where Q is covalently bonded through L to $R^2$, $R^3$ or an optional ring structure including $R^2$ and $R^3$, where each of $R^1$, $R^2$, $R^3$ and $R^4$ are each independently selected and are as described in connection with Formula E1 (below), and where each of $P''$, j, k, l, Q, L, Y, Y* and $P'''$ are as described in connection with the polymer (bio)conjugate compound of Formula IA.

In preferred embodiments E can be a chain extension residue of Formula E2,

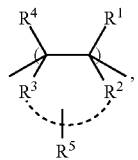  (E2)

and the polymer (bio)conjugate can preferably comprise a polymer of Formula IC,

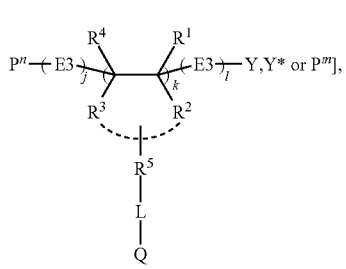  (IC)

where Q is covalently bonded through L to $R^5$, and $R^5$ is a substituent pendant from at least one of $R^2$, $R^3$ or the optional ring structure including $R^2$ and $R^3$, where each of $R^1$, $R^2$, $R^3$, $R^4$, and each $R^5$ are independently selected and are as described in connection with Formula E2 (below), and where each of $P''$, j, k, l, Q, L, Y, Y* and $P'''$ are as described in connection with the polymer (bio)conjugate compound of Formula IA.

In preferred embodiments E can be a chain extension residue of Formula E3,

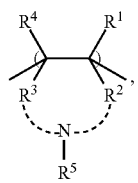  (E3)

and the polymer (bio)conjugate can preferably comprise a polymer of Formula ID,

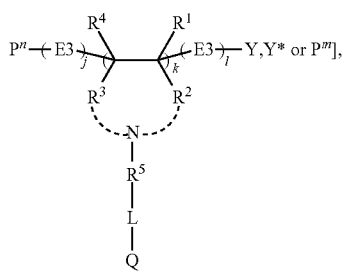  (ID)

where Q is covalently bonded through L to $R^5$, and $R^5$ is a substituent pendant from a nitrogen atom (e.g., from an amine functional group) included within least one of $R^2$, $R^3$ or the optional ring structure including $R^2$ and $R^3$, where each of $R^1$, $R^2$, $R^3$, $R^4$, and each $R^5$ are independently selected and are as described in connection with Formula E3 (below), and where each of P″, j, k, l, Q, L, Y, Y* and P′″ are as described in connection with the polymer (bio)conjugate compound of Formula IA.

With reference to the polymeric compounds of any of Formula IA, IB, IC or ID, in each case j, k and l are each independently selected integers, and in preferred embodiments: (i) j ranges from 0 to 4, k is >1, l ranges from 0 to 4, and the sum (j+k+l) is <5; alternatively (ii) j ranges from 0 to 2, k is >1, l ranges from 0 to 2, and the sum (j+k+l) is <3; or alternatively, (iii) j is 0, k is 1, and l is 0.

In polymeric compounds of the invention, including the polymeric compounds of Formula IA and Formula IIA as described above, the chain extension residue, each E can preferably comprise one or more independently selected functional groups; in preferred embodiments, the chain extension residue, E, can preferably comprise a reactive amine functional group (e.g., a primary amine or a secondary amine) or a corresponding ammonium salt thereof.

In polymeric compounds of the invention, including the polymeric compounds of Formula IA and Formula IIA as described above, the polymeric compound can comprise a chain transfer agent residue, Y. Preferably, such a polymeric compound can be a macromolecular chain transfer agent (e.g., where Y is capable of further reversible addition-fragmentation chain transfer (RAFT) polymerization; e.g., has a living character). Preferably, the polymeric compound can be a macromolecular chain transfer agent in substantially isolated form, the macromolecular chain transfer agent having a formula IIIA, $$P''\text{-}(E)_k\text{-}Y \qquad (IIIA),$$

where each of P″, E, k and Y is as described above in connection with Formula IIA or Formula IA (e.g., including where E is a chain extension residue comprising one or more bioconjugate moieties, Q, covalently linked thereto, e.g., through a linking moiety, L).

In polymeric compounds of the invention, including the polymeric compounds of Formula IA and Formula IIA as described above, the polymeric compound can comprise a block copolymer comprising two or more polymer blocks (e.g., discrete polymer chains), typically separated by one or more chain extension moieties, (E*). Generally, the polymeric compounds of the invention can comprise an A-(E*)-B block copolymer or an A-(E*)-B block copolymer conjugate, comprising a first block A of the copolymer defined by the first polymer chain, P″, and a second block B of the copolymer defined by the second polymer chain, P′″, and a chain extension moiety (E*) comprising one or more chain extension residue(s), E. Preferably, the second block B can be different from (e.g., have a different chemical composition or different arrangement of atoms and/or different physical properties from) the first block A. Preferably, such a polymeric compound can be an A-(E*)-B block copolymer having a formula IVA $$P''\text{-}(E)_k\text{-}P'''  \qquad (IVA),$$

where each of P″, E, k and P′″ is as described above in connection with Formula IIA or Formula IA (e.g., including where E is a chain extension residue comprising one or more bioconjugate moieties, Q, covalently linked thereto, e.g., through a linking moiety, L).

In polymeric compounds of the invention, including the polymeric compounds of Formula IA and Formula IIA as described above, the polymeric compound can comprise a polymer compound wherein the chain extension moiety (E*) consists of one chain extension residue, E. Preferably, such chain extension moiety (E*) comprising a singular chain extension residue, E, is derived from reversible addition-fragmentation chain transfer (RAFT) chain extension reaction using a non-homopolymerizable monomer, as further described below. Generally, the polymeric compounds of the invention can comprise a polymer having a formula VA $$P''\text{-}E\text{-}[Y \text{ or } Y^*] \qquad (VA),$$

where each of P″, E, Y and Y* is as described above in connection with Formula IIA or Formula IA (e.g., including where E is a chain extension residue comprising one or more bioconjugate moieties, Q, covalently linked thereto, e.g., through a linking moiety, L).

In polymeric compound compounds of the invention, including polymeric compounds of Formula IA and Formula IIA as described above, the polymeric compound can comprise a polymer compound or a polymer (bio)conjugate, in each case comprising an A-(E*)-B block copolymer having a formula IVE $$P''\text{-}(E)_k\text{-}P'''\text{-}(E)_l \qquad (IVE),$$

where P″ is a first polymer chain derived from radical polymerization, the first polymer chain defining a first block A of the copolymer, each E is an independently selected chain extension residue, k is an integer ranging from 1 to 10, l is an integer ranging from 0 to 10, Pm is a second polymer chain derived from radical polymerization, the second polymer chain defining a second block B of the copolymer, and (E*) represents a chain extension moiety comprising the extension residue(s). Optionally, at least one biomolecular agent, Q, is covalently bonded to a chain extension residue E of one or more of the chain extension moieties, (E*), in each case through an independently selected linking moiety, L.

The polymeric compounds as described and as variously exemplified herein are preferred, and can be generally used with any aspects, embodiments and approaches described herein.

In the various aspects of the invention disclosed or claimed herein (including each aspect of the invention and each general embodiment thereof) the compounds of the invention (or compositions including such compounds) can comprise one or more polymer chains and one or more chain extension moieties. Such polymer chains and chain extension moieties can be derived from radical polymerization. Preferably, in each case, such polymer chains and/or chain extension moieties can be independently derived from controlled (or living) radical polymerization in a method comprising polymerizing in the presence of a chain transfer agent (CTA), as described more fully herein below.

Chain Extension Moiety

Generally, each chain extension moiety, represented by (E*), comprises a limited number of chain extension residues, E. Each chain extension residue can be a monomeric residue derived from radical chain-extension polymerization of a chain extension monomer. Preferably, the chain extension residue(s), E, can be derived from reversible addition-fragmentation chain transfer (RAFT) chain extension reaction using a non-homopolymerizable monomer, as described below.

Generally, and with further reference to FIGS. 1A through 1D, for example, a polymer or a polymer conjugate can comprise one or more chain extension moieties, (E*), where each chain extension moiety comprises a limited number, preferably not more than 20, more preferably not more than 10, and most preferably not more than 5 chain extension residues, E, and where each chain extension residue is a monomeric residue derived from radical chain-extension polymerization of a monomer. In some embodiments, each chain extension moiety, (E*), comprises not more than 3, not more than 2, or not more than 1 (singular) chain extension residue(s), E, and where each chain extension residue is a monomeric residue derived from radical chain-extension polymerization of a monomer. Hence, generally for any chain extension residue characterized by formula -(E)$_k$- (e.g., the polymeric compounds comprising polymers of any of Formula IA, Formula IIA, Formula IIIA, Formula IVA, Formula IVB, Formula IVC, Formula IVD, Formula IVE, Formula IVF, and Formula VA), k is preferably an integer ranging from 1 to 5, or an integer ranging from 1 to 3, or k is 1. For any chain extension residue characterized by formula -(E)$_l$- (e.g., for Formula IVE, Formula IVF), the subscript l is generally preferably an integer ranging from 1 to 5, ranging from 1 to 3, or l is 1.

Generally, each chain extension residue can be independently selected. Typically, the one or more chain extension residues of a certain particular chain extension moiety are the same (i.e., are derived from the same chain extension monomer). In some instances, however, chain extension of a polymer chain could be effected using two or more chain extension monomers in a selected stoichiometric ratio to form a chain extension moiety comprising a random distribution of the two or more chain extension residues. Further, each of any two chain extension moieties may have chain extension residue(s) which are the same or different (i.e., may be derived from the same or different chain extension monomers) as compared between chain extension moieties.

Generally, any chain extension moiety of the invention can be a terminal chain extension moiety, for example covalently bonded to the ω-end of a first polymer chain (an ω-terminal chain extension moiety). Alternatively, the chain extension moiety can be a junctional chain extension moiety, for example covalently bonded between two polymer chains—e.g., bonded to the ω-end of a first polymer chain and to the α-end of a second polymer chain.

Generally, any chain extension moiety of the invention (e.g., a terminal chain extension moiety or a junctional chain extension moiety) can optionally be a conjugating chain extension moiety, covalently liked to one or more (biologically relevant) bioconjugate moieties (e.g., through a linking moiety).

In one approach, for example, the chain extension residues, E, of the invention can preferably comprise one or more substituent groups, preferably at least one of which can comprise a (one or more) functional group. In polymer conjugates of the invention, a biomolecular agent (moieties) can be covalently bonded to the functional group(s) of such substituent group(s) through a linking moiety. The linking moiety can be a chemical bond, or can include a moiety comprising one or more covalently bonded atoms, as discussed below.

Hence, a polymer compound or a polymer conjugate can comprise zero, one or more terminal chain extension moieties, zero, one or more junctional chain extension moieties, and additionally or alternatively zero, one or more conjugating chain extension moieties, provided preferably however, that such polymer compound or such polymer conjugate comprises at least one chain extension moiety which is either a terminal chain extension moiety or a junctional chain extension moiety, and in each case, can optionally also be a conjugating chain extension moiety.

Preferably, the chain extension residues, E, are derived by radical polymerization, and preferably reversible addition-fragmentation chain transfer (RAFT) polymerization, from chain extension monomers with little or no homopolymerizability under chain extension reaction conditions, generally referred to herein as a non-homopolymerizable monomers or as monomers which do not substantially homopropagate. With reference to Scheme 2.2, Scheme 2.4 and Scheme 3.2 of FIG. 8, such non-homopolymerizable monomers can be characterized with respect to the propagation rate constant, $k_p$, under chain extension polymerization reaction conditions. Reference herein to "non-homopolymerizable" or to "little to no homopolymerizability" or to "does not substantially homopropagate" can mean that the propagation rate constant, $k_p$ (L/mol/sec.) of the monomer is less than 2000 under chain extension conditions, preferably less than 1500, and preferably less than 1000; and in some embodiments, the propagation rate constant, $k_p$ (L/mol/sec.) of the monomer can be less than 500, less than 300, or less than 200. Preferably, therefore, each chain extension moiety (E*) can comprise one or more chain extension residue(s), E, which are monomeric residue(s) derived from radical polymerization (preferably via RAFT polymerization) of a polymerizable monomer having a propagation rate constant, $k_p$, less than about 2000 under chain extension polymerization reaction conditions, preferably less than 1500, and preferably less than 1000 under chain extension conditions; and in some embodiments, the propagation rate constant, $k_p$ of the monomer can be less than 500, less than 300, or less than 200, in each case under chain extension conditions. Generally, reliable values for propagation rate constant, $k_p$, for many common monomers are known in the art. (See, e.g., Beuermann et al., *Prog. Polym. Sci.*, 27, 191 (2002)). Values for propagation rate constant, $k_p$, can also be determined by approaches known in the art, as generally described in Moad et al., The Chemistry of Radical Polymerization, 2d Ed., pp. 216-218, Elsevier (2006), including preferably pulsed laser photolysis approaches (See Beuermann et al., Id., See Moad et al., Id.).

With reference to Scheme 3 of FIG. 8, such non-homopolymerizable monomers can additionally or alternatively be characterized based on the ceiling temperature, $T_c$, associated with homopropagation of the chain extension monomer (Scheme 3.2, FIG. 8). Without being bound by theory not expressly recited in the claims, the homopropagation of polymer radicals, e.g., P$^n$·, with ethylenically unsaturated chain extension monomers, $M^E$, has a thermodynamic basis as a reversible reaction (Scheme 3.1, FIG. 8). The extent of depropagation increases with increasing temperature (e.g., due to entropic effects) and therefore. The ceiling temperature, $T_c$, is the temperature at which the rate of propagation and depropagation become equal. Generally, below $T_c$, there can be expected a net propagation of polymerization; above $T_c$, there can be expected a net depolymerization. Ceiling temperature, $T_c$, and the propagation/depropagation equilibrium constant ($K_{eq}$, Scheme 3.1, FIG. 8) can be measured by studying the equilibrium between chain extension monomer and polymer, or alternatively can be calculated at various temperatures given values of enthalpy ($\Delta H_p$) and entropy ($\Delta S_p$) of propagation, for example using the relationships of Equations 1.1 and 1.2:

$$K_{eq} = \exp(\Delta H_p/RT - \Delta S_p/R) = 1/[M^E]_{eq} \quad \text{(Eqn. 1.1)}$$

$$T_c = \Delta H_p/(\Delta S_p + R \ln [M^E]) \quad \text{(Eqn. 1.2)},$$

as generally described in Moad et al., The Chemistry of Radical Polymerization, 2d Ed., pp. 213-216, Elsevier (2006). Preferably, in the context of the various aspects of the invention (including all general embodiments thereof), chain extension monomers preferably have a ceiling temperature, $T_c$, of less than about 200° C., or less than about 175° C., or less than about 150° C., and in some embodiments less than about 125° C., or less than about 100° C. For context, and without limitation, Moad et al., Id., report ceiling temperatures, $T_c$, of various monomers suitable as chain extension monomers within the context of the present invention, for example such as methylmethacrylate (MMA) having a $T_c$~200° C., methacrylonitrile (MAN) having a $T_c$~200° C., and α-methylstyrene (AMS) having a $T_c$~30° C.

Generally, chain extension monomers having relative low propagation rate constant, $k_p$, can be selected by considering various factors, including for example the relative activation energies associated with such monomers in chain extension polymerization reactions, and the relative stability of the resulting propagating radicals in chain extension polymerization reactions. Generally, and without limitation due to variable exceptions, a lower propagation rate constant, $k_p$, is favored with relative increased activation energies and relatively increased stability of propagating radicals.

Generally, chain extension monomer can include ethylenically unsaturated monomers which are substantially non-homopolymerizable under the chain extension reaction conditions.

Suitable chain extension monomers can be selected, for example, from among monomers having an α-H substituent (e.g., styrene (S), butadiene (B)).

Suitable chain extension monomers of the invention can be generally and, and preferably from among ethylenically unsaturated monomers having an α-alkyl, α-carboxylic acid, α-carboxylate (acid ester) or other α-substituents. For example, suitable chain extension monomers can include acrylic monomers, acrylate monomers, acrylamide monomers, and acrylonitrile monomers which are α-substituted with a hydrocarbyl moiety, for example with an α-alkyl, α-carboxylic acid, or α-carboxylate (acid ester) moiety. Preferably, in each case, such α-substituent moiety is a $C_1$-$C_{12}$ hydrocarbyl moiety, $C_1$-$C_8$ hydrocarbyl moiety, a $C_1$-$C_6$ hydrocarbyl moiety, or a $C_1$-$C_4$ hydrocarbyl moiety. Preferably in each case such α-substituent moiety is preferably a $C_1$-$C_{12}$, $C_1$-$C_8$, $C_1$-$C_6$, or $C_1$-$C_4$ moiety which is selected from an α-alkyl, α-carboxylic acid, or α-carboxylate (acid ester) moiety. Generally, and without limitation due to variable exceptions, the propagation rate constant, $k_p$, tends to decrease with increasing length or steric bulk of such α-substituent moieties.

For example, more specific chain extension monomers can be selected from among α-alkyl acrylic acids such as (α-)methacrylic acid, (α-)ethylacrylic acid, (α-) propylacrylic acid, and (α-)butylacrylic acid. For example, more specific chain extension monomers can be selected from among alkyl α-alkylacrylates such as alkyl (α-)methacrylates, alkyl (α-)ethylacrylates, alkyl (α-)propylacrylates, and alkyl (α-)butylacrylates, where preferably in each case the ester alkyl moiety is preferably an unsubstituted or substituted $C_1$-$C_4$ alkyl moiety. Generally, and without limitation due to variable exceptions, the propagation rate constant, $k_p$, tends to increase with increasing length of the ester alkyl chain. For example, more specific chain extension monomers can be selected from among α-alkylacrylamides (including α-alkylacrylamides, N-alkyl α-alkylacrylamides or N,N-dialkyl α-alkylacrylamides) such as (optionally amide-substituted N—H-alkyl or N,N-dialkyl) (α-)methacrylamides, (optionally amide-substituted N—H-alkyl or N,N-dialkyl) (α-)ethylacrylamides, (optionally amide-substituted N—H-alkyl or N,N-dialkyl) (α-)propylacrylamides, and (optionally amide-substituted N—H-alkyl or N,N-dialkyl) (α-)butylacrylamides, where preferably in each case the N-substituent(s) are each independently selected unsubstituted or substituted $C_1$-$C_4$ alkyl moiety. For example, more specific chain extension monomers can be selected from among α-alkyl acrylonitriles such as (α-)methacrylonitrile, (α-)ethylacrylonitrile, (α-) propyl acrylonitrile, and (α-) butyl acrylonitrile.

Examples of preferred chain extension monomers which are ethylenically unsaturated, α-substituted monomers include α-methyl substituted monomers, such as without limitation methacrylic acid (MAA), methyl methacrylate (MMA), ethyl methacrylate (EMA), n-butyl methacrylate (nBMA), i-butyl methacrylate (aBMA), 2-ethylhexyl methacrylate (EHMA), glycidyl methacrylate (GMA) and methacrylonitrile (MAN). Examples of preferred chain extension monomers which are ethylenically unsaturated, α-substituted monomers include α-ethyl substituted monomers, such as without limitation methyl ethylacrylate (MEA).

With reference to the various polymeric compounds of the invention as disclosed herein, and in particular for example with reference to the polymeric compounds comprising polymers of any of Formula IA, Formula IIA, Formula IIIA, Formula IVA and Formula VA, preferred chain extension residues, E (derived by radical polymerization from corresponding chain extension monomers), can include those certain chain extension residues of any of Formula E1, Formula E2, and Formula E3:

(E1)

(E2)

(E3)

Generally, for each of Formula E1, Formula E2 and Formula E3 independently: $R^1$, $R^2$, $R^3$ and $R^4$ are each independently selected from the group consisting of hydrogen, hydrocarbyl, substituted hydrocarbyl, hetero-hydrocarbyl and substituted hetero-hydrocarbyl, where optionally $R^2$ and $R^3$ are in a covalent ring structure. Preferably, for each formula, the aforementioned hydrocarbyl, substituted hydrocarbyl, hetero-hydrocarbyl and/or substituted hetero-hydrocarbyl, can in each case be a $C_1$-$C_{20}$ moiety, $C_1$-$C_{16}$ moiety $C_1$-$C_{12}$ moiety, $C_1$-$C_8$ moiety, a $C_1$-$C_6$ moiety, or a $C_1$-$C_4$ moiety. Preferably, for each formula, the aforementioned hydrocarbyl, substituted hydrocarbyl, hetero-hydrocarbyl and/or substituted hetero-hydrocarbyl, can in each case be a carbocyclic, substituted carbocyclic, heterocyclic, substituted heterocyclic, an aryl, substituted aryl, heteroaryl, or substituted heteroaryl, or fused multi-ring structures comprising one or more of the foregoing. For Formula E2, $R^5$ is a substituent pendant from at least one of $R^2$, $R^3$ or the optional ring structure including $R^2$ and $R^3$, and preferably the $R^5$ substituent comprises one or more functional groups. For Formula E3, $R^5$ is a substituent pendant from a nitrogen atom (e.g., from an amine functional group) included within least one of $R^2$, $R^3$ or the optional ring structure including $R^2$ and $R^3$, and preferably, the $R^5$ substituent comprises one or more functional groups. Preferably, for each formula, the aforementioned optional ring structure including $R^2$ and $R^3$ can include carbocyclic, substituted carbocyclic, heterocyclic, substituted heterocyclic, aryl, substituted aryl, heteroaryl, substituted heteroaryl, or fused multi-ring structures comprising one or more of the foregoing.

Preferably, for each of the chain extension residue(s) of Formula E1, Formula E2, and Formula E3 considered independently, and in each case considered without stereospecificity, and also for each of the polymer (bio)conjugate compounds of Formula IB, Formula IC and Formula ID considered independently:

- each $R^1$ is independently selected from the group consisting of hydrogen, and $C_1$-$C_{20}$ moiety selected from hydrocarbyl, substituted hydrocarbyl, hetero-hydrocarbyl, substituted hetero-hydrocarbyl, which can include a carbocyclic, substituted carbocyclic, heterocyclic, substituted heterocyclic, an aryl, substituted aryl, heteroaryl, or substituted heteroaryl, or fused multi-ring structures comprising one or more of the foregoing,
- each $R^2$ is independently selected from the group consisting of hydrogen, and $C_1$-$C_{20}$ moiety selected from hydrocarbyl, substituted hydrocarbyl, hetero-hydrocarbyl, substituted hetero-hydrocarbyl, which can also include a carbocyclic, substituted carbocyclic, heterocyclic, substituted heterocyclic, an aryl, substituted aryl, heteroaryl, or substituted heteroaryl, or fused multi-ring structures comprising one or more of the foregoing,
- each $R^3$ is independently selected from the group consisting of hydrogen, and $C_1$-$C_{20}$ moiety selected from hydrocarbyl, substituted hydrocarbyl, hetero-hydrocarbyl, substituted hetero-hydrocarbyl, which can also include a carbocyclic, substituted carbocyclic, heterocyclic, substituted heterocyclic, an aryl, substituted aryl, heteroaryl, or substituted heteroaryl, or fused multi-ring structures comprising one or more of the foregoing,
- provided that when $R^2$ and $R^3$ are in a covalent ring structure, then considered together, such ring structure can be a $C_1$-$C_{24}$ moiety selected from carbocyclic, substituted carbocyclic, heterocyclic, substituted heterocyclic, aryl, substituted aryl, heteroaryl, or substituted heteroaryl, or fused multi-ring structures comprising one or more of the foregoing, and
- each $R^4$ is independently selected from the group consisting of hydrogen, and $C_1$-$C_{20}$ moiety selected from hydrocarbyl, substituted hydrocarbyl, hetero-hydrocarbyl, substituted hetero-hydrocarbyl, which can also include a carbocyclic, substituted carbocyclic, heterocyclic, substituted heterocyclic, an aryl, substituted aryl, heteroaryl, or substituted heteroaryl, or fused multi-ring structures comprising one or more of the foregoing.

Preferably, for each such $R^1$, $R^2$, $R^3$ and $R^4$ considered independently:

- each $R^1$ is independently selected from the group consisting of hydrogen, $C_1$-$C_8$ alkyl, $C_1$-$C_8$ alkenyl, $C_1$-$C_8$ alkynyl, $C_1$-$C_8$ allenyl, $C_1$-$C_8$ alkoxy, $C_1$-$C_8$ alkyl thio, $C_1$-$C_8$ ether, $C_1$-$C_8$ carboxylic acid, $C_1$-$C_8$ carboxyl ester, $C_1$-$C_8$ amide, $C_1$-$C_8$ nitrile, $C_1$-$C_8$ ketone, $C_1$-$C_8$ aldehyde, $C_1$-$C_8$ acyl halide, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aralkenyl, $C_1$-$C_{16}$ aralkynyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaralkenyl, $C_1$-$C_{16}$ heteroaralkynyl, $C_1$-$C_{16}$ heteroaryloxy, and $C_1$-$C_{16}$ alkheteroaryl (in each case substituted or unsubstituted),
- each $R^2$ is independently selected from the group consisting of hydrogen, $C_1$-$C_8$ alkyl, $C_1$-$C_8$ alkenyl, $C_1$-$C_8$ alkynl, $C_1$-$C_8$ allenyl, $C_1$-$C_8$ alkoxy, $C_1$-$C_8$ alkyl thio, $C_1$-$C_8$ ether, $C_1$-$C_8$ carboxylic acid, $C_1$-$C_8$ carboxyl ester, $C_1$-$C_8$ amide, $C_1$-$C_8$ nitrile, $C_1$-$C_8$ ketone, $C_1$-$C_8$ aldehyde, $C_1$-$C_8$ acyl halide, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aralkenyl, $C_1$-$C_{16}$ aralkynyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaralkenyl, $C_1$-$C_{16}$ heteroaralkynyl, $C_1$-$C_{16}$ heteroaryloxy, and $C_1$-$C_{16}$ alkheteroaryl (in each case substituted or unsubstituted),
- each $R^3$ is independently selected from the group consisting of hydrogen, $C_1$-$C_8$ alkyl, $C_1$-$C_8$ alkenyl, $C_1$-$C_8$ alkynl, $C_1$-$C_8$ allenyl, $C_1$-$C_8$ alkoxy, $C_1$-$C_8$ alkyl thio, $C_1$-$C_8$ ether, $C_1$-$C_8$ carboxylic acid, $C_1$-$C_8$ carboxyl ester, $C_1$-$C_8$ amide, $C_1$-$C_8$ nitrile, $C_1$-$C_8$ ketone, $C_1$-$C_8$ aldehyde, $C_1$-$C_8$ acyl halide, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aralkenyl, $C_1$-$C_{16}$ aralkynyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaralkenyl, $C_1$-$C_{16}$ heteroaralkynyl, $C_1$-$C_{16}$ heteroaryloxy, and $C_1$-$C_{16}$ alkheteroaryl (in each case substituted or unsubstituted),
- provided that when $R^2$ and $R^3$ are in a covalent ring structure, then considered together, such ring structure can be a $C_1$-$C_{16}$ moiety selected from carbocyclic, substituted carbocyclic, heterocyclic, substituted heterocyclic, aryl, substituted aryl, heteroaryl, or substituted heteroaryl, or fused multi-ring structures comprising one or more of the foregoing, and
- each $R^4$ is independently selected from the group consisting of hydrogen, $C_1$-$C_8$ alkyl, $C_1$-$C_8$ alkenyl, $C_1$-$C_8$ alkynl, $C_1$-$C_8$ allenyl, $C_1$-$C_8$ alkoxy, $C_1$-$C_8$ alkyl thio, $C_1$-$C_8$ ether, $C_1$-$C_8$ carboxylic acid, $C_1$-$C_8$ carboxyl ester, $C_1$-$C_8$ amide, $C_1$-$C_8$ nitrile, $C_1$-$C_8$ ketone, $C_1$-$C_8$ aldehyde, $C_1$-$C_8$ acyl halide, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aralkenyl, $C_1$-$C_{16}$ aralkynyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaralkenyl, $C_1$-$C_{16}$ heteroaralkynyl, $C_1$-$C_{16}$ heteroaryloxy, and $C_1$-$C_{16}$ alkheteroaryl (in each case substituted or unsubstituted).

Preferably, for each such $R^1$, $R^2$, $R^3$ and $R^4$ considered independently:

- each $R^1$ is independently selected from the group consisting of hydrogen, $C_1$-$C_8$ alkyl, $C_1$-$C_8$ alkoxy, $C_1$-$C_8$ carboxylic acid, $C_1$-$C_8$ carboxyl ester, $C_1$-$C_8$ amide, $C_1$-$C_8$ nitrile, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaryloxy, and $C_1$-$C_{16}$ alkheteroaryl (in each case substituted or unsubstituted), each $R^2$ is independently selected from the group consisting of hydrogen, $C_1$-$C_8$ alkyl, $C_1$-$C_8$ alkoxy, $C_1$-$C_8$ carboxylic acid, $C_1$-$C_8$ carboxyl ester, $C_1$-$C_8$ amide, $C_1$-$C_8$ nitrile, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaryloxy, and $C_1$-$C_{16}$ alkheteroaryl (in each case substituted or unsubstituted), each $R^3$ is independently selected from the group consisting of hydrogen, $C_1$-$C_8$ alkyl, $C_1$-$C_8$ alkoxy, $C_1$-$C_8$ carboxylic acid, $C_1$-$C_8$ carboxyl ester, $C_1$-$C_8$ amide, $C_1$-$C_8$ nitrile, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaryloxy, and $C_1$-$C_{16}$ alkheteroaryl (in each case substituted or unsubstituted), provided that when $R^2$ and $R^3$ are in a covalent ring structure, then considered together, such ring structure can be a $C_1$-$C_{16}$ moiety selected from carbocyclic, substituted carbocyclic, heterocyclic, substituted heterocyclic, aryl, substituted aryl, heteroaryl, or substituted heteroaryl, or fused multi-ring structures comprising one or more of the foregoing, and each $R^4$ is independently selected from the group consisting of hydrogen, $C_1$-$C_8$ alkyl, $C_1$-$C_8$ alkoxy, $C_1$-$C_8$ carboxylic acid, $C_1$-$C_8$ carboxyl ester, $C_1$-$C_8$ amide, $C_1$-$C_8$ nitrile, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaryloxy, and $C_1$-$C_{16}$ alkheteroaryl $C_1$-$C_8$ heteroaryl, $C_1$-$C_{16}$ heteroaralkyl, $C_1$-$C_{16}$ heteroaryloxy, and $C_1$-$C_{16}$ alkheteroaryl (in each case substituted or unsubstituted).

Preferably, for each such $R^1$, $R^2$, $R^3$ and $R^4$ considered independently:

each $R^1$ is independently selected from the group consisting of hydrogen, $C_1$-$C_8$ alkyl, $C_1$-$C_8$ alkoxy, $C_1$-$C_8$ carboxylic acid, $C_1$-$C_8$ carboxyl ester, $C_1$-$C_8$ amide, $C_1$-$C_8$ nitrile, $C_1$-$C_8$ acid anhydride (in each case substituted or unsubstituted), each $R^2$ is independently selected from the group consisting of hydrogen, $C_1$-$C_8$ alkyl, $C_1$-$C_8$ alkoxy, $C_1$-$C_8$ carboxylic acid, $C_1$-$C_8$ carboxyl ester, $C_1$-$C_8$ amide, $C_1$-$C_8$ nitrile, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaryloxy, and $C_1$-$C_{16}$ alkheteroaryl (in each case substituted or unsubstituted), each $R^3$ is independently selected from the group consisting of hydrogen, $C_1$-$C_8$ alkyl, $C_1$-$C_8$ alkoxy, $C_1$-$C_8$ carboxylic acid, $C_1$-$C_8$ carboxyl ester, $C_1$-$C_8$ amide, $C_1$-$C_8$ nitrile, $C_1$-$C_8$ acid anhydride, $C_1$-$C_{16}$ carbocyclic, $C_1$-$C_{16}$ heterocyclic, $C_1$-$C_{16}$ aryl, $C_1$-$C_{16}$ aralkyl, $C_1$-$C_{16}$ aryloxy, $C_1$-$C_{16}$ alkaryl, $C_1$-$C_{16}$ heteroaryl, $C_1$-$C_{16}$ heteroaralkyl, $C_1$-$C_{16}$ heteroaryloxy, and $C_1$-$C_{16}$ alkheteroaryl (in each case substituted or unsubstituted), provided that when $R^2$ and $R^3$ are in a covalent ring structure, then considered together, such ring structure can be $C_1$-$C_{16}$ carbocyclic, $C_1$-$C_{16}$ heterocyclic, $C_1$-$C_{16}$ aryl, $C_1$-$C_{16}$ alkaryl, $C_1$-$C_{16}$ heteroaryl, $C_1$-$C_{16}$ alkheteroaryl (in each case substituted or unsubstituted) and fused multi-ring structures comprising one or more of the foregoing, and each $R^4$ is independently selected from the group consisting of hydrogen, $C_1$-$C_8$ alkyl, $C_1$-$C_8$ alkoxy, $C_1$-$C_8$ carboxylic acid, $C_1$-$C_8$ carboxyl ester, $C_1$-$C_8$ amide, $C_1$-$C_8$ nitrile, $C_1$-$C_8$ acid anhydride (in each case substituted or unsubstituted).

Preferably, for each such $R^1$, $R^2$, $R^3$ and $R^4$ considered independently:

each $R^1$ is independently selected from the group consisting of hydrogen, $C_1$-$C_6$ alkyl, $C_1$-$C_6$ carboxylic acid, $C_1$-$C_6$ carboxyl ester, and $C_1$-$C_6$ amide (in each case substituted or unsubstituted), each $R^2$ is independently selected from the group consisting of hydrogen, $C_1$-$C_6$ alkyl, $C_1$-$C_6$ carboxylic acid, $C_1$-$C_6$ carboxyl ester, and $C_1$-$C_6$ amide, $C_1$-$C_{12}$ carbocyclic, $C_1$-$C_{12}$ heterocyclic, $C_1$-$C_{12}$ aryl, $C_1$-$C_{12}$ aralkyl, $C_1$-$C_{12}$ aryloxy, $C_1$-$C_{12}$ alkaryl, $C_1$-$C_{12}$ heteroaryl, $C_1$-$C_{12}$ heteroaralkyl, $C_1$-$C_{12}$ heteroaryloxy, and $C_1$-$C_{12}$ alkheteroaryl (in each case substituted or unsubstituted), each $R^3$ is independently selected from the group consisting of hydrogen, $C_1$-$C_6$ alkyl, $C_1$-$C_6$ carboxylic acid, $C_1$-$C_6$ carboxyl ester, and $C_1$-$C_6$ amide, $C_1$-$C_{12}$ carbocyclic, $C_1$-$C_{12}$ heterocyclic, $C_1$-$C_{12}$ aryl, $C_1$-$C_{12}$ aralkyl, $C_1$-$C_{12}$ aryloxy, $C_1$-$C_{12}$ alkaryl, $C_1$-$C_{12}$ heteroaryl, $C_1$-$C_{12}$ heteroaralkyl, $C_1$-$C_{12}$ heteroaryloxy, and $C_1$-$C_{12}$ alkheteroaryl (in each case substituted or unsubstituted), provided that when $R^2$ and $R^3$ are in a covalent ring structure, then considered together, such ring structure can be $C_1$-$C_{12}$ carbocyclic, $C_1$-$C_{12}$ heterocyclic, $C_1$-$C_{12}$ aryl, $C_1$-$C_{12}$ alkaryl, $C_1$-$C_{12}$ heteroaryl, $C_1$-$C_{12}$ alkheteroaryl (in each case substituted or unsubstituted) and fused multi-ring structures comprising one or more of the foregoing, and each $R^4$ is independently selected from the group consisting of hydrogen, $C_1$-$C_6$ alkyl, $C_1$-$C_6$ carboxylic acid, $C_1$-$C_6$ carboxyl ester, and $C_1$-$C_6$ amide (in each case substituted or unsubstituted).

Preferably, for each such $R^1$, $R^2$, $R^3$ and $R^4$ considered independently:

each $R^1$ is independently selected from the group consisting of hydrogen, $C_1$-$C_4$ alkyl, $C_1$-$C_4$ carboxylic acid, $C_1$-$C_4$ carboxyl ester, and $C_1$-$C_4$ amide (in each case substituted or unsubstituted), each $R^2$ is independently selected from the group consisting of hydrogen, $C_1$-$C_6$ alkyl, $C_1$-$C_6$ carboxylic acid, $C_1$-$C_6$ carboxylate (ester), and $C_1$-$C_6$ amide (in each case substituted or unsubstituted), each $R^3$ is independently selected from the group consisting of hydrogen, $C_1$-$C_6$ alkyl, $C_1$-$C_6$ carboxylic acid, $C_1$-$C_6$ carboxylate (ester), and $C_1$-$C_6$ amide (in each case substituted or unsubstituted)

provided that when $R^2$ and $R^3$ are in a covalent ring structure, then considered together, such ring structure can be $C_1$-$C_8$ carbocyclic, $C_1$-$C_8$ heterocyclic, $C_1$-$C_8$ aryl, $C_1$-$C_8$ alkaryl, $C_1$-$C_8$ heteroaryl, $C_1$-$C_8$ alkheteroaryl (in each case substituted or unsubstituted) and fused multi-ring structures comprising one or more of the foregoing, each $R^4$ is independently selected from the group consisting of hydrogen, $C_1$-$C_4$ alkyl, $C_1$-$C_4$ carboxylic acid, C₁-C₄ carboxyl ester, and C₁-C₄ amide (in each case substituted or unsubstituted).

Generally, for each of Formula E1, Formula E2 and Formula E3, at least one of the independently selected $R^1$, $R^2$, $R^3$ and $R^4$ is other than hydrogen. (Each such $R^1$, $R^2$, $R^3$ and $R^4$ is otherwise selected as described in the various embodiments and subembodiments herein).

Generally, for each of Formula E1, Formula E2 and Formula E3, at least two of the independently selected $R^1$, $R^2$, $R^3$ and $R^4$ are other than hydrogen. (Each such $R^1$, $R^2$, $R^3$ and $R^4$ is otherwise selected as described in the various embodiments and subembodiments herein).

Generally, for each of Formula E1, Formula E2 and Formula E3, at least three of the independently selected $R^1$, $R^2$, $R^3$ and $R^4$ are other than hydrogen. (Each such $R^1$, $R^2$, $R^3$ and $R^4$ is otherwise selected as described in the various embodiments and subembodiments herein).

Generally, for each of Formula E1, Formula E2 and Formula E3, at least one of the independently selected $R^1$, $R^2$, $R^3$ and $R^4$ is hydrogen, and at least two of the independently selected $R^1$, $R^2$, $R^3$ and $R^4$ are other than hydrogen. (Each such $R^1$, $R^2$, $R^3$ and $R^4$ is otherwise selected as described in the various embodiments and subembodiments herein).

Generally, for each of Formula E1, Formula E2 and Formula E3, at least two of the independently selected $R^1$, $R^2$, $R^3$ and $R^4$ are hydrogen, and at least two of the independently selected $R^1$, $R^2$, $R^3$ and $R^4$ are other than hydrogen. (Each such $R^1$, $R^2$, $R^3$ and $R^4$ is otherwise selected as described in the various embodiments and subembodiments herein).

Generally in preferred embodiments, for each of Formula E1, Formula E2 and Formula E3, the substituents $R^2$ and $R^3$ are in a covalent ring structure, and each of $R^1$, $R^2$, $R^3$ and $R^4$ are independently selected as described in the various embodiments and subembodiments herein.

In such preferred embodiments where $R^2$ and $R^3$ are in a covalent ring structure, then considered together, such ring structure can be a carbocyclic moiety (substituted or unsubstituted), generally including non-hetero cyclic moieties such as (non-hetero) alicyclic moieties and (non-hetero) aromatic moieties (in each case substituted or unsubstituted). Preferred carbocyclic moieties can include saturated or unsaturated alicyclic moieties, for example, such as cycloalkanes, cycloalkenes, or cycloalkynes (in each case substituted or unsubstituted).

For example, carbocyclic moieties can include saturated carbocyclic moieties such as monocyclic or multicyclic (e.g., bicyclic) cycloalkyl moieties, for example cyclopropyl, cyclobutyl, cyclopentyl, cyclohexyl, and decalin (in each case substituted or unsubstituted).

For example, carbocyclic moieties can include unsaturated carbocyclic moieties such as monocyclic or multicyclic (e.g., bicyclic) cycloalkenyl moieties, for example cyclopropenyl, cyclobutenyl, cyclopentenyl, cyclohexenyl, 1,3-cyclohexadienyl, 1,4-cyclohexadienyl, cycloheptenyl, 1,5-cyclooctadienyl, and cyclooctynyl (in each case substituted or unsubstituted).

For example, carbocyclic moieties can include aromatic (non-hetero) carbocyclic moieties, for example benzyl, phenyl, naphthalenyl, phenanthrenyl, anthracenyl, triphenylenyl, pyrenyl, naphthacenyl, and chrysenyl, among others (in each case substituted or unsubstituted). Preferred substituted aryl moieties can include for example and without limitation toluenyl, xylenyl, ethylbenzenyl, mesitylenyl, durenyl, anilinyl, benzoic acidyl, biphenyl, clorobenzyl, nitrobenzyl, paracetamol, phenol, phenacetinyl, picric acidyl, salicyclic acidyl, and trinitrotoluenyl.

In such preferred embodiments where $R^2$ and $R^3$ are in a covalent ring structure, then considered together, such ring structure can be a heterocyclic moiety (substituted or unsubstituted), generally including heterocyclic moieties such as heteroalicyclic moieties and heteroaromatic moieties (in each case substituted or unsubstituted). Preferred heterocyclic moieties can include saturated or unsaturated heterocyclic moieties (in each case substituted or unsubstituted).

For example, heterocyclic moieties can include saturated nitrogen-containing heterocyclic moieties such as arizidinyl (ethylene imine), azetidinyl (1,3 propylene imine), pyrrolidinyl (tetrahydropyrrole), imidazolidinyl (tetrahydroimidazole), thiazolidinyl, oxazolidinyl, isoxazolidinyl, piperidinyl, piperazinyl, and oxazinyl (in each case substituted or unsubstituted). As described below, in some embodiments, the substituents can include acyl moieties. In some embodiments, the substituents can include two acyl moieties such that the ring structure comprises an imidyl (imide) moiety, —C(O)NR$^I$C(O)—, where $R^I$ is hydrogen, hydrocarbyl or substituted hydrocarbyl.

For example, the heterocyclic moieties alternatively can include unsaturated nitrogen-containing heterocyclic moieties such as pyrrolyl, imidazolyl, thiazolyl, isothiazolyl, oxazolyl, isoxazolyl, triazolyl (e.g., 1,2,3-triazolyl, or e.g., 1,2,4-triazolyl), dithiazolyl, tetrazolyl, pyridinyl, pyrazinyl (1,4-diazinyl), pyrimidinyl (1,3-diazinyl), pyridazinyl (1,2-diazinyl), thiazinyl, triazinyl (e.g., 1,2,3-triazinyl, e.g., 1,2,4-triazinyl, e.g., 1,3,5-triazinyl), and tetrazinyl (e.g., 1,2,3,4-tetrazinyl, e.g., 1,2,4,5-tetrazinyl) (in each case substituted or unsubstituted).

For example, heterocyclic moieties can include (saturated or unsaturated) imidyl-containing heterocyclic moieties. Such heterocyclic moiety can comprise an imidyl (imide) moiety, for example as represented by a formula —C(O)NR$^I$C(O)— where $R^I$ is hydrogen, hydrocarbyl or substituted hydrocarbyl. Preferred imidyl-containing moieties can include as non-limiting examples maleimide or phthalimide residues (i.e., moieties derived from chain extension polymerization of maleimide and phthalimide chain extension monomers, respectively) (in each case substituted or unsubstituted).

For example, heterocyclic moieties can include saturated oxygen-containing heterocyclic moieties such as ethylene oxide, oxetanyl (1,3 propylene oxide), dioxetanyl (e.g., 1,2 dioxetanyl, e.g., 1,3 dioxetanyl, tetrahydrofuranyl, dioxolanyl, oxazolidinyl, isoxazolidinyl, tetrahydropyranyl, oxazinyl, and dioxanyl (e.g., 1,2-dioxanyl, e.g., 1,3-dioxanyl, e.g., 1-4-dioxanyl) (in each case substituted or unsubstituted).

For example, the heterocyclic moieties alternatively can include unsaturated oxygen-containing heterocyclic moieties such as oxirenyl, furanyl, oxazolyl, isoxazolyl, pyranyl, dioxinyl (e.g., 1,2-dioxinyl, e.g., 1,4-dioxinyl) (in each case substituted or unsubstituted).

For example, heterocyclic moieties can include saturated sulfur-containing heterocyclic moieties such as thiiranyl (ethylene sulfide), thietanyl, dithietanyl (e.g., 1,2-dithietanyl, e.g., 1,3-dithietanyl), tetrahydrothiophenyl, dithiolanyl (e.g., 1,2-dithiolanyl, e.g., 1,3-dithiolanyl), thiazolidinyl, thianyl, and dithianyl (e.g., 1,2-dithianyl, e.g., 1,3-dithianyl, e.g., 1,4-dithianyl) (in each case substituted or unsubstituted).

For example, the heterocyclic moieties alternatively can include unsaturated sulfur-containing heterocyclic moieties such as dithieteyl, thiophenyl (thiofuranyl), dihydrothiophenyl (dihydrothiofuranyl), thiazolyl, isothiozolyl, dithiazolyl, thiinyl (thiapyranyl), and thiazinyl, (in each case substituted or unsubstituted).

Generally in especially preferred embodiments, for Formula E3, the substituents $R^2$ and $R^3$ are in a covalent ring structure, each of $R^1$ and $R^4$ are independently selected as described in the various embodiments and subembodiments herein, and $R^2$ and $R^3$ are in a heterocyclic ring structure. The heterocyclic ring structure can include, for example, saturated nitrogen-containing heterocyclic moieties such as arizidinyl (ethylene imine), azetidinyl (1,3 propylene imine), pyrrolidinyl (tetrahydropyrrole), imidazolidinyl (tetrahydroimidazole), thiazolidinyl, oxazolidinyl, isoxazolidinyl, piperidinyl, piperazinyl, and oxazinyl (in each case substituted or unsubstituted). Alternatively, the heterocyclic can include unsaturated nitrogen-containing heterocyclic moieties such as pyrrolyl, imidazolyl, thiazolyl, isothiazolyl, oxazolyl, isoxazolyl, triazolyl (e.g., 1,2,3-triazolyl, or e.g., 1,2,4-triazolyl), dithiazolyl, tetrazolyl, pyridinyl, pyrazinyl (1,4-diazinyl), pyrimidinyl (1,3-diazinyl), pyridazinyl (1,2-diazinyl), thiazinyl, triazinyl (e.g., 1,2,3-triazinyl, e.g., 1,2,4-triazinyl, e.g., 1,3,5-triazinyl), and tetrazinyl (e.g., 1,2,3,4-tetrazinyl, e.g., 1,2,4,5-tetrazinyl) (in each case substituted or unsubstituted). Alternatively, the heterocyclic can include (saturated or unsaturated) imidyl-containing heterocyclic moieties, for example as represented by a formula —C(O)NR$^i$C(O)— where R$^i$ is hydrogen, hydrocarbyl or substituted hydrocarbyl. Preferred imidyl-containing moieties can include as non-limiting examples maleimide or phthalimide residues (i.e., moieties derived from chain extension polymerization of maleimide and phthalimide chain extension monomers, respectively) (in each case substituted or unsubstituted).

Preferably, for each of the chain extension residue(s) of Formula E2 and Formula E3, considered independently, and also for each of the polymer (bio)conjugate compounds of Formula IC and Formula ID considered independently, and further for each of the chain extension monomers M1 through M19 described below, each $R^5$ is independently selected and preferably comprises hydrogen or a $C_1$-$C_{20}$ moiety selected from hydrocarbyl, substituted hydrocarbyl, hetero-hydrocarbyl, substituted hetero-hydrocarbyl, which can also include a carbocyclic, substituted carbocyclic, heterocyclic, substituted heterocyclic, an aryl, substituted aryl, heteroaryl, or substituted heteroaryl, or fused multi-ring structures comprising one or more of the foregoing, and in each case such $C_1$-$C_{20}$ moiety optionally having a reactive functional group (masked or unmasked), where such functional group can be selected from amino (e.g., primary, secondary), ammonio, imino, amido, imidyl, nitrile, azo, azido, cyano, cyanato, isocyanato, isothiocyanto, hydrazide, nitro, nitroso, nitrosooxy, pyridyl, hydroxyl, alkoxy, carboxyl, ester, acyl, halo, haloformyl, phosphino, phosphoric, phospho, sulfide, di-sulfide, thio, thiol, sulfonyl, sulfo, sulfinyl, alkenyl, alkynl, allenyl, and silyl.

Preferably, each such $R^5$ is independently selected and preferably comprises hydrogen or a $C_1$-$C_{12}$ moiety selected from hydrocarbyl, substituted hydrocarbyl, hetero-hydrocarbyl, substituted hetero-hydrocarbyl, which can also include a carbocyclic, substituted carbocyclic, heterocyclic, substituted heterocyclic, an aryl, substituted aryl, heteroaryl, or substituted heteroaryl, or fused multi-ring structures comprising one or more of the foregoing, and in each case such $C_1$-$C_{12}$ moiety optionally having a reactive functional group (masked or unmasked), where such functional group can be selected from amino (e.g., primary, secondary), ammonio, imidyl, nitrile, pyridyl, hydrazide, hydroxyl, carboxyl, ester, acyl, halo, sulfide, di-sulfide, thio, thiol, and alkenyl.

Preferably, each such $R^5$ is independently selected and preferably comprises hydrogen or a $C_1$-$C_8$ moiety selected from alkyl, substituted alkyl, carbocyclic, substituted carbocyclic, heterocyclic, substituted heterocyclic, aryl, substituted aryl, heteroaryl, or substituted heteroaryl, or fused multi-ring structures comprising one or more of the foregoing, and in each case such $C_1$-$C_8$ moiety optionally having a reactive functional group (masked or unmasked), where such functional group can be selected from amino (e.g., primary, secondary), ammonio, imidyl, nitrile, pyridyl, hydrazide, hydroxyl, carboxyl, ester, acyl, halo, sulfide, di-sulfide, thio, thiol, and alkenyl.

Preferably, each such $R^5$ is independently selected and preferably comprises hydrogen or a $C_1$-$C_8$ moiety selected from alkyl, substituted alkyl, carbocyclic, substituted carbocyclic, heterocyclic, substituted heterocyclic, aryl, substituted aryl, heteroaryl, or substituted heteroaryl, or fused multi-ring structures comprising one or more of the foregoing, and in each case such $C_1$-$C_8$ moiety having one or more reactive functional groups (masked or unmasked) selected from amino (e.g., primary, secondary), ammonio, imidyl, nitrile, pyridyl, hydrazide, hydroxyl, carboxyl, ester, acyl, halo, sulfide, di-sulfide, thio, thiol, and alkenyl.

Preferably, each such $R^5$ is independently selected and preferably comprises hydrogen or a $C_1$-$C_5$ moiety selected from alkyl, substituted alkyl, carbocyclic, substituted carbocyclic, heterocyclic, substituted heterocyclic, aryl, substituted aryl, heteroaryl, or substituted heteroaryl, or fused multi-ring structures comprising one or more of the foregoing, and in each case such $C_1$-$C_8$ moiety having one or more reactive functional groups (masked or unmasked) selected from amino (e.g., primary, secondary) and ammonio Preferably, each such $R^5$ is independently selected and preferably comprises a biomolecular moiety, Q, as described herein.

Preferred chain extension monomers can be monomers which form chain extension residues of Formula E1, Formula E2 or Formula E3, as described herein, during chain extension polymerization.

Preferred chain extension monomers (from which preferred chain extension residues, E, are derived by radical polymerization) can include, for example, maleimide, N-substituted maleimides, (including but not limited to, N-phenylmaleimide, N-methylmaleimide, N-ethylmaleimide, N-benzylmaleimide, N-propylmaleimide, N-(4-ethylphenyl)maleimide, N-(4-acetylphenyl) maleimide, N-(para-tolyl)-maleimide, N-cyclohexyl maleimide N-dodecyl maleimide, N-tert-butyl maleimide, N-isopropyl maleimide, N-(2-hydroxyethyl) maleimide, N-(3-hydroxypropyl) maleimide, and various N-aminoalkyl, such as N-(2-aminoethyl) maleimide, N-(2-aminopropyl) maleimide, and N-(3-aminopropyl) maleimide), maleic anhydride, maleic acid, fumaric acid, maleic esters (including but not limited to, di-n-butyl maleate, di-n-amyl maleate, diethyl maleate, diisoamyl maleate, dimethyl maleate, diphenyl maleate, and di-n-propylmaleate), fumaric esters (including but not limited to, di-n-amyl fumarate, diethyl fumarate, diisoamyl fumarate, diisobutyl fumarate, diisopropyl fumarate, dimethyl fumarate, diphenyl fumarate, and di-n-propyl fumarate), allyl and methallyl compounds, (such as (meth)allylsulfonate, (meth)allylglycidylether, (meth)alkylvinylether, (meth)allylbutyl ether, (meth)allylethyl ether, and (meth) allylmethyl ether), vinyl ethers, vinyl sulphonates, vinyl phosphonates, 1,3-butadiene derivatives, itaconic acid derivatives (including but not limited to, di-n-butyl ester, diethyl ester, dimethyl ester and dicyclohexyl ester), alpha-alkylstyrene, alpha-ethylacrylate, cis and trans stilbene, and other monomers which are substantially non-homopolymerizable under chain extension conditions.

The chain extension monomers of the immediately preceding paragraph can optionally be substituted (before use in a chain extension polymerization reaction). For example, such chain extension monomers can be substituted with any $R^5$ moiety as described in connection with Formula E2 or Formula E3. For example, bis-functional maleimides can be used. For example, such chain extension monomers can be substituted with any biomolecular moiety, Q, as described herein.

Particularly preferred chain extension monomers (from which preferred chain extension residues, E, are derived by radical polymerization) include monomers shown in Table 1. With respect to chain extension monomers represented by Formulas M1 through M19 in this table, each $R^5$ can be independently selected and can be as described in connection with Formula E2 or Formula E3. In the chain extension monomers represented by Formulas M16, M17, M18 and M19, each Q1 is independently selected from aryl, substituted aryl, heteroaryl, substituted heteroaryl, preferably where each such (substituted or unsubstituted) aryl or (substituted or unsubstituted) heteroaryl comprises from one to three ring structures, each such ring structure comprising from three to seven atoms, and each Q2 is independently selected from aryl, substituted aryl, heteroaryl, substituted heteroaryl, preferably where each such (substituted or unsubstituted) aryl or (substituted or unsubstituted) heteroaryl comprises from one to three ring structures, each such ring structure comprising from three to seven atoms. Preferably, for the chain extension monomers of Formulas M16, M17, M18 and M19, with respect to each of Q1 and Q2, a substituted aryl can preferably be an $R^5$-substituted aryl, and a substituted heteroaryl can preferably be an $R^5$-substituted heteroaryl, where each $R^5$ is independently selected and can be as described in connection with Formula E2 or Formula E3.

Preferably, with respect to chain extension monomers represented by Formulas M1 through M19 in Table 1, each $R^5$ can be independently selected and preferably comprises a $C_1$-$C_4$ amine (e.g., primary, secondary) and ammonium salts thereof.

Preferably, with respect to chain extension monomers represented by Formulas M1 through M19 in Table 1, each $R^5$ can be independently selected and preferably comprises a reaction functional group selected from amino (e.g., primary, secondary) and ammonio.

Chain Transfer Residue, —Y

Compounds of the invention, including for each of the various aspects and embodiments thereof, can include a chain transfer residue, —Y, on the ω-terminal end of a chain-extended polymer (e.g. in a compound comprising $P''$-$(E)_k$-Y). The chain transfer residue can be derived from radical polymerization. The chain transfer residue can be derived from controlled (living) radical polymerization of a chain extension monomer under chain extension conditions. Such controlled radical extension reactions can be effected for example in the presence of a chain transfer agent (CTA) such as a RAFT agent (e.g., Y—$R^L$) or such as a macro-CTA (e.g., $P''$—Y). The chain-transfer residue, —Y, is typically covalently bonded to a chain extension moiety of a chain-extended polymer on the ω-end thereof (also referred to as the living end of the chain extension moiety when included in a macro CTA).

In embodiments, therefore, the moiety —Y in the various compounds of the invention is a chain transfer residue. The chain transfer residue, —Y, can preferably be a thiocarbonylthio moiety having a formula —SC(=S)Z, where Z is an activating group. The activating group, Z, can be —X($R^Z$)$_a$ where X is selected from the group consisting of O, N, C and S, $R^Z$ is an activating substituent, and a is an integer equal to 1, 2 or 3, corresponding to the valency of X. For example, where X is O, the chain transfer residue, —Y, can be represented by a formula —SC(=S)O$R^Z$ (xanthates). In another embodiment, where X is N, the chain transfer residue, —Y, can be represented by a formula —SC(=S)N$R^{Z1}R^{Z2}$ (dithiocarbamates). In a further embodiment, where X is C, the chain transfer residue, —Y, can be represented by a formula —SC(=S) $R^{Z1}R^{Z2}R^{Z3}$ (diothioesters). In an additional embodiment, where X is S, the chain transfer residue, —Y, can be represented by a formula —SC(=S)S$R^Z$ (trithiocarbonates). In each case the activating substituents, $R^Z$, $R^{Z1}$, $R^{Z2}$, $R^{Z3}$ are not narrowly critical, and are generally selected from hydrogen, substituted or unsubstituted hydrocarbyl, and substituted or unsubstituted hetero-hydrocarbyl. Generally, activating substituents, $R^Z$, $R^{Z1}$, $R^{Z2}$, $R^{Z3}$ are known in the art, including as described above in connection with RAFT agents. As known in the art, for example, two or more of such activating substituents $R^{Z1}$, $R^{Z2}$, $R^{Z3}$ can be linked in a cyclic or heterocyclic moiety. One or more of such activating substituents $R^{Z1}$, $R^{Z2}$, $R^{Z3}$ can represent one bond of a double bond.

Various RAFT chain-transfer agents are known for use in controlled (living) radical polymerizations, including various xanthates, dithiocarbamates, diothioesters and trithiocarbonates. See for example, Moad et al., The Chemistry of Radical Polymerization, 2d Ed., Tables 9.10 to 9.18 at pp. 508 to 514, Elsevier (2006), which is incorporated herein by reference. The various chain transfer residues, —Y, and various activating groups, Z, are apparent therefrom.

Chain Transfer Residue Derivative (Y*)

Compounds of the invention, including for each of the various aspects and embodiments thereof, can include a chain transfer residue derivative, —Y*, on the ω-terminal end of a chain-extended polymer (e.g. in a compound comprising $P''$-$(E)_k$-Y*). The chain transfer residue derivative can be derived from a compound comprising a chain transfer residue, —Y, derived from radical polymerization. The chain transfer residue, —Y, can be derived from controlled (living) radical polymerization of a chain extension monomer under chain extension conditions.

Preferably, the chain transfer residue derivative, Y*, is a moiety other than a radical moiety, and is derived from cleavage of or derivatization of the chain transfer residue Y.

Various approaches are known for cleaving and/or derivatizing the chain transfer residue, Y. See for example, Moad et al., The Chemistry of Radical Polymerization, 2d Ed., pp. 538 to 539, Elsevier (2006), which is incorporated herein by reference. See also U.S. Pat. No. 6,619,409 to Charmot et al., which discloses cleavage of the thiocarbonylthio control transfer agent. The various chain transfer residue derivatives, —Y*, resulting from such known approaches are apparent therefrom.

In some embodiments, the chain transfer residue derivative, Y* is selected from the group consisting of hydrogen and —SH.

Polymer Chains

Generally, the various polymer chains included as constituent moieties of the compounds of the invention, generally represented by $P''$, $P'''$, $P°$, etc., can comprise one or more repeat units—monomer residues—derived from radical polymerization, preferably from reversible fragmentation-addition chain transfer (RAFT) polymerization, of one or more polymerizable monomers.

Generally, each polymer chain, $P^n$, $P^m$, $P^o$, etc., can be a homopolymer (derived from polymerization of one single type of monomer—having essentially the same chemical composition) or a copolymer (derived from polymerization of two or more different monomers—having different chemical compositions). Polymer chains which are copolymers can be a random copolymer chain or a block copolymer chain (e.g., diblock copolymer chain, triblock copolymer, etc). Any given block copolymer chain (e.g. $P^n$, $P^m$, $P^o$, etc.) can be conventionally configured and effected (e.g., without inclusion of chain extension residue(s)) according to methods known in the art.

Generally, each polymer chain, $P^n$, $P^m$, $P^o$, etc., can be a linear polymer, or a non-linear polymer. Non-linear polymers can have various architectures, including for example branched polymers, star-polymers, dendrimer polymers, and can be cross-linked polymers, semi-cross-linked polymers, graft polymers, and combinations thereof. Various polymer architectures are advantageously achieved with a high degree of control by the controlled (living) polymerization methods such as RAFT polymerization.

Generally, a polymer chain, $P^n$, $P^m$, $P^o$, etc., can be a prepared by controlled (living) radical polymerization, such as reversible addition-fragmentation chain transfer (RAFT) polymerization. Such methods and approaches are generally known in the art, and are further described herein. Alternatively, a polymer chain, $P^n$, $P^m$, $P^o$, etc., can be a prepared by conventional polymerization approaches, including conventional radical polymerization approaches. In such cases, before chain extension according to the present invention, the polymer chains can be covalently modified to include a chain transfer moiety (e.g., —SC(=S)Z, where Z is an activating group) at the ω-end of the polymer chain, thereby forming a macromolecular chain transfer agent (macro-CTA) effective for controlled (e.g., RAFT) chain extension.

Generally, a polymer chain, $P^n$, $P^m$, $P^o$, etc., is prepared by a method other than by stepwise coupling approaches involving a sequence of multiple individual reactions (e.g., such as known in the art for peptide synthesis or for oligonucleotide synthesis). Preferably, a polymer chain, $P^n$, $P^m$, $P^o$, etc., is a non-peptidic polymer chain (consists of a polymer other than an amino acid polymer). Preferably, a polymer chain, $P^n$, $P^m$ $P^o$, etc., is a non-nucleic acid polymer chain (consists of a polymer other than a nucleic acid polymer. For clarity, notwithstanding and without prejudice to the foregoing two sentences, the biomolecular agent, Q, of the invention can be an amino acid polymer (e.g., a peptide) or a nucleic acid polymer (e.g., an oligonucleotide). Preferably, a polymer chain is not polyethylene glycol (PEG) or polypropylene glycol (PPG).

Generally, polymer chains, $P^n$, $P^m$, $P^o$, etc., prepared by controlled (living) radical polymerization, such as reversible addition-fragmentation chain transfer (RAFT) polymerization, may include moieties other than the monomeric residues (repeat units). For example, and without limitation, such polymer chains may include polymerization-process-dependent moieties at the α-end or at the ω-end of the polymer chain. Typically, for example, a polymer chain, $P^n$, derived from controlled radical polymerization such as RAFT polymerization may further comprise a radical source residue covalently coupled with the α-end thereof. For example, the radical source residue can be an initiator residue, or the radical source residue can be a leaving group, $—R^L$, of a reversible addition-fragmentation chain transfer (RAFT) agent. Typically, as another example, a polymer chain, $P^n$, derived from controlled radical polymerization such as RAFT polymerization may further comprise a chain transfer residue covalently coupled with the ω-end thereof. As described further below (in connection with RAFT polymerization), such polymer chains (or such compounds of the invention) can comprises a chain transfer residue, —Y, which is a thiocarbonylthio moiety having a formula —SC(=S)Z, where Z is an activating group. Typical RAFT chain transfer residues are derived from radical polymerization in the presence of a chain transfer agent selected from xanthates, dithiocarbamates, dithioesters, and trithiocarbonates.

Further aspects of the polymer chains, $P^n$, $P^m$, $P^o$, etc., are disclosed in the following paragraphs, including preferred polymerizable monomers from which the repeat units of the polymer chains are derived.

Generally, and preferably, the polymer chains, $P^n$, $P^m$, $P^o$, etc can comprise repeat units derived from ethylenically unsaturated monomers. The term "ethylenically unsaturated monomer" is defined herein as a compound having at least one carbon double or triple bond. The non-limiting examples of the ethylenically unsaturated monomers are: an alkyl (alkyl)acrylate, a alkyl methacrylate, an alkylacrylic acid, an N-alkylacrylamide, a methacrylamide, a styrene, an allylamine, an allylammonium, a diallylamine, a diallylammonium, an n-vinyl formamide, a vinyl ether, a vinyl sulfonate, an acrylic acid, a sulfobetaine, a carboxybetaine, a phosphobetaine, or maleic anhydride.

In various embodiments, any monomer suitable for providing the polymer chains, $P^n$, $P^m$, $P^o$, etc described herein is used. In some embodiments, monomers suitable for use in the preparation of polymers chains provided herein include, by way of non-limiting example, one or more of the following monomers: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, vinylnaphthalene, vinyl pyridine, ethylvinylbenzene, aminostyrene, vinylimidazole, vinylpyridine, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylammonium ethyl methacrylate, trimethylammonium propyl acrylamide, dodecyl acrylate, octadecyl acrylate, or octadecyl methacrylate monomers, or combinations thereof.

In some embodiments, polymer chains can be derived from certain specific monomers and combinations of monomers, for example, for use in connection with various embodiments, such as for uses associated with polynucleotide-containing compositions. Such preferred polymer chains are described below.

Generally, polymer chains, $P''$, $P'''$, $P^o$, etc. can include repeat units derived from functionalized versions of the aforementioned monomers. A functionalized monomer, as used herein, can include a monomer comprising a masked (protected) or non-masked (unprotected) functional group, e.g. a group to which other moieties can be attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994).

As used herein, a "block" copolymer refers to a structure comprising one or more sub-combination of constitutional or monomeric units. In some embodiments, the block copolymer is a diblock copolymer. A diblock copolymer comprises two blocks; a schematic generalization of such a polymer is represented by the following: [AaBbCc . . . ]m-[XxYyZz . . . ]n, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by such schematic representation, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the form: x-x-y-z-x-y-y-z-y-z-z-z . . . An exemplary alternating random configuration may have the form: x-y-x-z-y-x-y-z-y-x-z . . . , and an exemplary regular alternating configuration may have the form: x-y-z-x-y-z-x-y-z . . . An exemplary regular block configuration may have the following general configuration: . . . x-x-x-y-y-y-z-z-x-x-x . . . , while an exemplary random block configuration may have the general configuration: . . . x-x-x-z-z-x-x-y-y-y-z-z-z-x-x-z-z-z- . . . In a gradient polymer, the content of one or more monomeric units increases or decreases in a gradient manner from the end of the polymer to the end. In none of the preceding generic examples is the particular juxtaposition of individual constitutional units or blocks or the number of constitutional units in a block or the number of blocks meant nor should they be construed as in any manner bearing on or limiting the actual structure of block copolymers forming the polymeric carrier of this invention.

As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers.

A "monoblock polymer" is a synthetic product of a single polymerization step. The term monoblock polymer includes a copolymer such as a random copolymer (i.e. a product of polymerization of more than one type of monomers) and a homopolymer (i.e. a product of polymerization of a single type of monomers).

Preparation of Chain-Extended Polymeric Compounds Via Chain Extension Polymerization As noted above, the various aspects of the invention disclosed herein comprise one or more polymer chains, $P''$, $P'''$, $P^o$, etc., and one or more chain extension moiety ($E^*$). Generally, a chain extension moiety of the various aspects of the invention is prepared by a radical chain extension polymerization method. Preferably, such chain extension polymerization is based on a controlled (living) radical chain extension polymerization method such as reversible addition-fragmentation chain transfer (RAFT) polymerization.

Methods for preparing polymer chains by RAFT polymerization are described below, and are generally applicable for the chain extension polymerizations, as described herein.

Polymeric compounds of the invention can be generally represented herein for discussion of the methods as a polymer having a formula IIA $$P''\text{-}(E)_k\text{-}[Y,Y^* \text{ or } P'''] \quad \text{(IIA)},$$

(as described above). Such polymeric compounds can be prepared as follows.

Generally, a polymeric compound of Formula IIA can be prepared by a method which includes (i) providing a macromolecular chain transfer agent having a formula $P''$-Y where —Y is the moiety —SC(=S)Z, and Z is activating group, and (ii) reacting a chain extension monomer, E, in the presence of an activated radical and the macromolecular chain transfer agent under chain extension conditions to form a chain-extension adduct having a formula $P''$-$(E)_k$-Y, where k is an integer ranging from 1 to 20, preferably from 1 to 10.

In preferred approaches, a polymeric compound of Formula IIA can be prepared where the extension moiety (E*) has a limited number of chain extension residues—for example where in Formula IIA, k is an integer not more than 20, preferably not more than 10, preferably not more than 5, preferably not more than 3 and most preferably k is 1. Such polymeric compound can be prepared for example, by a method which includes (i) providing a macromolecular chain transfer agent having a formula $P''$—Y where Y is $SC(=S)Z$, and Z is activating group and the macromolecular chain transfer agent having a polydispersity index, Mw/Mn, of less than 1.5, and (ii) reacting a chain extension monomer, E, in the presence of an activated radical and the macromolecular chain transfer agent under chain extension conditions to form a chain-extension adduct having a formula $P''$-$(E)_k$-Y, where k is an integer ranging from 1 to 20, preferably from 1 to 10, preferably 1 to 5, preferably 1 to 3 and most preferably 1, and where the chain-extension adduct has a polydispersity index, Mw/Mn, of less than 1.5.

Preferably, chain extension polymerization is effected so as to preserve the relatively narrow polydispersity of the parent polymer—the macromolecular chain transfer agent as recited in the immediately-preceding paragraph. Preferably, for example the polydispersity index of the chain-extension adduct, $P''$-$(E)_k$-Y, differs from the polydispersity index of the macromolecular chain transfer agent, $P''$—Y, by not more than 10%. Preferably, the polydispersity index of the chain-extension adduct, $P''$-$(E)_k$-Y, differs from the polydispersity index of the macromolecular chain transfer agent, $P''$—Y, by not more than 5%.

As noted, the chain extension monomers and corresponding chain extension residues resulting from the chain extension reaction can provide polymer chains which are selectively functionalized at the ω-terminal end of the chain.

Further, the living character of the chain transfer moiety at the ω-end allows for further radical polymerization to prepare block copolymers which are junction-functionalized, and optionally also ω-end functionalized. For example, diblock or higher-ordered block copolymers can be prepared having where the polymeric compound comprises a polymer compound or a polymer (bio)conjugate, in each case comprising an A-(E*)-B block copolymer (where (E*) represents a chain extension moiety comprising the extension residue(s)), the block copolymer having a formula IVE

   (IVE), where $P''$, E, k, l, $P'''$ are each as described above in connection with Formula IVE, and where optionally, at least one biomolecular agent, Q, is covalently bonded to a chain extension residue E, as likewise described above. Such di-block or higher-order block copolymers can be prepared by radical polymerization methods which include (i) providing a macromolecular chain transfer agent having a formula $P''$—Y where Y is $SC(=S)Z$, and Z is activating group, (ii) reacting a chain extension monomer, E, in the presence of an activated radical and the macromolecular chain transfer agent under chain extension conditions to form a chain-extension adduct having a formula $P''$-$(E)_k$-Y, where k is an integer ranging from 1 to 10, and reacting a second set B of one or more monomers in the presence of an activated radical and the chain-extension adduct under polymerization conditions to form an A-(E*)-B polymer having a formula $P''$-$(E)_k$-$P'''$-Y, the second set B of one or more monomers being the same as or different from the first set A of one or more monomers.

Generally, in any such methods of the invention, the macromolecular chain transfer agent of formula $P''$—Y can be prepared by radical polymerization approaches, preferably by reacting a first set A of one or more monomers in the presence of an activated radical and a chain transfer agent comprising a RAFT chain transfer moiety (e.g., a thiocabonyl-thio moiety) under polymerization conditions to form the macro-CTA. Such approach is advantageously consistent with known approaches for preparing polymer chains by controlled (living) radical polymerization, such as reversible addition-fragmentation chain transfer (RAFT) polymerization.

Alternatively, the macro-CTA for use in chain extension can be based on a polymer chain, $P''$, $P'''$, $P^o$, etc., prepared by conventional polymerization approaches, where such polymer chain has been covalently modified to include a chain transfer moiety (e.g., $—SC(=S)Z$, where Z is an activating group) at the ω-end of the polymer chain, thereby forming a macromolecular chain transfer agent (macro-CTA) effective for controlled (e.g., RAFT) chain extension.

These approaches can be effected with various chain extension monomers, as described above in connection with the chain extension moieties (E*), including using monomers which do not substantially homopropagate under chain extension polymerization conditions, and preferably also using monomers (e.g., N-substituted maleimides) that can accommodate a variety of reactive functional groups (e.g., amine functional groups). The availability and versatility of such reactive functional groups provides opportunities for effective bioconjugation, and thereby affords polymer conjugates such as polymer bioconjugates, with a (bio)conjugate moiety linked to the polymer chain through one or more chain extension residues, as described below.

Generally, chain extension polymerization conditions can be controllably varied to achieve an intended limited chain extension, for example and preferably to achieve incorporation of from 1 to 20, preferably from 1 to 10 monomeric residues by chain extension polymerization with a chain extension monomer in a process involving little or no homopolymerizability. Such conditions include for a selected chain extension monomer, as non-limiting examples, temperature, pressure, atmosphere, ratios of starting components used in the polymerization mixture and reaction time. The chain extension polymerization can be carried out in any suitable manner, including, e.g., in solution, dispersion, suspension, emulsion or bulk.

Generally, chain extension polymerization processes described herein optionally occur in any suitable solvent or mixture thereof. Suitable solvents generally include those described herein in connection with polymerization generally, below. Notably, depending on the selection of chain extension monomer, the value of homopropagation rate constant, $k_p$, can be influenced by reaction solvent, as is known in the art. For example, larger solvent effects have been reported for monomers which are ionizable (i.e., chargeable), involve precipitation polymerization and/or include hydroxy or amide groups. Solvent effects can be seen in combination with other effects, such as concentration of chain extension monomer in polar solvents (e.g., water).

Generally, chain extension polymerization described herein can be effected at temperature effective for the chain extension reaction, preferably to achieve incorporation of from 1 to 20, preferably from 1 to 10 monomeric residues by chain extension polymerization with a chain extension monomer in a process involving little or no homopolymerizability. Temperatures can be varied based on and in consideration of other reaction aspects, including for example selections as to solvent, monomer (or comonomers) being polymerized (or copolymerized), chain transfer agent, heat transfer (exotherm control), reaction kinetics, and reaction thermodynamics. Typical temperature ranges can generally include those described herein in connection with polymerization generally, below. Notably, however, and without being bound by theory not expressly recited in the claims, the propagation of polymer radicals, e.g., P''., with ethylenically unsaturated chain extension monomers has a thermodynamic basis as a reversible reaction (e.g., See Scheme 3.1, FIG. 8); such that an overall propagation rate constant can be a temperature-influenced variable. For example, as temperature is increased, the entropically-favored depropagation reaction becomes increasingly favored, thereby resulting in more limited chain extension propagation. This is expected especially for certain preferred chain extension monomers (e.g., alpha-substituted acrylate monomers or alpha-substituted acrylamide monomers).

Generally, the chain-extension reaction processes described herein can be effected at a pressure effective for the chain extension reaction, preferably to achieve incorporation of from 1 to 20, preferably from 1 to 10 monomeric residues by chain extension polymerization with a chain extension monomer in a process involving little or no homopolymerizability. Generally, reaction pressure ranges can generally include those described herein in connection with polymerization generally, below.

Generally, polymerization processes described herein can be effected under a reaction atmosphere effective for the chain extension reaction, preferably to achieve incorporation of from 1 to 20, preferably from 1 to 10 monomeric residues by chain extension polymerization with a chain extension monomer in a process involving little or no homopolymerizability. Generally, reaction atmosphere can include those described herein in connection with polymerization generally, below.

Generally, the chain-extension reaction processes described herein can be effected at various molar ratios of chain transfer agent (living chain transfer moieties or groups) to chain extension monomer effective for the chain extension reaction, preferably to achieve incorporation of from 1 to 20, preferably from 1 to 10 monomeric residues by chain extension polymerization with a chain extension monomer in a process involving little or no homopolymerizability. For example, polymerization can be effected with a molar ratio of chain transfer agent (groups) to monomer ranging from about 1:1 to about 1,000, preferably from about 1:5 to about 1:750, and most preferably from about 1:10 to about 1:500; In some embodiments, such molar ratio can range from about 1:50 to about 1:400, or from 1:75 to about 1:400.

Generally, the chain-extension reaction processes described herein can be effected at concentrations of monomer(s) in the solvent effective for the chain extension reaction, preferably to achieve incorporation of from 1 to 20, preferably from 1 to 10 monomeric residues by chain extension polymerization with a chain extension monomer in a process involving little or no homopolymerizability. Generally, monomer(s) concentration can generally include those described herein in connection with polymerization generally, below. Notably, however, monomer(s) concentration can have an impact on propagation rate constant, especially in polar solvents, as noted above.

Generally, the chain-extension reaction processes described herein can be effected at various molar ratios of chain transfer agent (living chain transfer moieties or groups) to initiator effective for the chain extension reaction, preferably to achieve incorporation of from 1 to 20, preferably from 1 to 10 monomeric residues by chain extension polymerization with a chain extension monomer in a process involving little or no homopolymerizability. Generally, molar ratio of CTA:Initiator can generally include those described herein in connection with polymerization generally, below.

Generally, the chain-extension reaction processes described herein can be effected for various reaction times effective to achieve incorporation of from 1 to 20, preferably from 1 to 10 monomeric residues by chain extension polymerization with a chain extension monomer in a process involving little or no homopolymerizability. Generally, reaction times can generally include those described herein in connection with polymerization generally, below.

The aforementioned aspects and other factors known in the art can be used to effect the chain extension polymerization reaction of interest. See generally, for example, Moad et al., The Chemistry of Radical Polymerization, 2d Ed., Elsevier (2006), which is incorporated herewith in this regard.

Polymerization, Generally

Generally, the various polymer chains included as constituent moieties of the compounds of the invention, generally represented by $P''$, $P'''$, $P^o$, etc. can be prepared in any suitable manner. Suitable synthetic methods used to produce the polymers provided herein include, by way of non-limiting example, cationic, anionic and free radical polymerization. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

Preferably the polymer chains (as well as the chain extension moieties, (E*) as described above) are prepared by the means of a free radical polymerization. When a free radical polymerization process is used, (i) the monomer, (ii) optionally, the co-monomer, and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Polymerization conditions are those conditions that cause at least one monomer to form at least one polymer, as discussed herein. Such conditions are optionally varied to any suitable level and include, by way of non-limiting example, temperature, pressure, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiator is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a controlled (living) mode. Preferred controlled (living) polymerization processes include reversible addition-fragmentation chain transfer (RAFT) polymerization processes. The universality and substantial flexibility of RAFT radical polymerization further enhances the applications of such approaches. Hence, among the aspects of the invention disclosed and claimed herein are polymeric compounds such as functionalized polymers and polymer (bio) conjugates with substantial architectural diversity.

In preferred embodiments, Reversible Addition-Fragmentation chain Transfer or RAFT is used in synthesizing polymer chains from ethylenic monomers, and preferably is also applied for chain extension reactions of the invention. RAFT is a controlled (living) polymerization process. RAFT comprises a free radical degenerative chain transfer process. In some embodiments, RAFT procedures for preparing a polymer described herein employs a chain transfer agent (CTA). In some embodiments, the chain transfer agents are thiocarbonylthio compounds such as, without limitation, dithioesters, dithiocarbamates, trithiocarbonates and xanthates to mediate polymerization by a reversible chain transfer mechanism. In certain instances, reaction of a polymeric radical with the C=S group of any of the preceding compounds leads to the formation of stabilized radical intermediates. Typically, these stabilized radical intermediates do not undergo the termination reactions typical of standard radical polymerization but, rather, reintroduce a radical capable of re-initiation or propagation with monomer, reforming the C—S bond in the process. In most instances, this cycle of addition to the C—S bond followed by fragmentation of the ensuing radical continues until all monomer has been consumed or the reaction is quenched. Generally, the low concentration of active radicals at any particular time limits normal termination reactions.

Generally, polymer chains and/or chain extension moieties can be independently derived in a method comprising polymerizing in the presence of a reversible addition-fragmentation chain-transfer (RAFT) agent. Such RAFT agents can generally have the formula Y—$R^L$, where $R^L$ is a leaving group, typically coupled to a chain-transfer moiety, Y, through a relatively weak covalent bond. Typically, Y can be a chain-transfer moiety capable of reversible addition-fragmentation chain transfer. For example, Y can form a radical intermediate moiety, —Y.—, generated from or in the presence of a radical moiety (e.g., such as an initiator radical (e.g., derived from an initiator such as $I_2$, AIBN, etc.) under initiation reaction conditions, or such as a propagating polymer chain radical, P"., under radical polymerization conditions). See generally, FIG. 8, Scheme 2.

In generally preferred embodiments, the chain transfer agent (CTA) can comprise a thiocarbonylthio moiety. For example, the CTA can comprise a thiocarbonylthio moiety, —SC(=S)—, covalently bonded to an activating group, Z, and to a leaving group, -$R^L$. Such CTA can be represented for example, by a compound having the formula $R^L$SC(=S) Z. The activating group, Z, can be —X($R^Z$)a where X is selected from the group consisting of O, N, C and S, $R^Z$ is an activating substituent, and a is an integer equal to 1, 2 or 3, corresponding to the valency of X. For example, a preferred CTA can be selected from xanthate compounds (where X is O), e.g., represented by a formula $R^L$ SC(=S) O$R^Z$. Another preferred CTA can be selected from dithiocarbamate compounds (where X is N), e.g., represented by a formula $R^L$ SC(=S)NR$R^{Z1}R^{Z2}$. A preferred CTA can alternatively be selected from dithioester compounds (where X is C), e.g., represented by a formula $R^L$SC(=S)C $R^{Z1}R^{Z2}R^{Z3}$. A further preferred CTA can be selected from trithiocarbonate compounds (where X is S), e.g., represented by a formula $R^L$SC(=S)S$R^Z$. The activating substituents, $R^Z$, $R^{Z1}$, $R^{Z2}$, and $R^{Z3}$ are not narrowly critical, and are generally independently selected from hydrogen, substituted or unsubstituted hydrocarbyl, or substituted or unsubstituted hetero-hydrocarbyl. Generally, activating substituents, $R^Z$, $R^{Z1}$, $R^{Z2}$, and $R^{Z3}$ are known in the art, including as described and shown below in connection with RAFT chain-transfer agents. As known in the art, for example, two or more of such activating substituents $R^{Z1}$, $R^{Z2}$, and $R^{Z3}$ can be linked in a cyclic or heterocyclic moiety. One or more of such activating substituents $R^{Z1}$, $R^{Z2}$, and $R^{Z3}$ can represent one bond of a double bond.

Various RAFT chain-transfer agents are known for use in controlled (living) radical polymerizations, including various xanthates, dithiocarbamates, diothioesters and trithiocarbonates.). See for example, Moad et al., The Chemistry of Radical Polymerization, 2d Ed., Tables 9.10 to 9.18 at pp. 508 to 514, Elsevier (2006), which is incorporated herein by reference.

Generally, the chain transfer agent (CTA) can be a macromolecular chain transfer agent (macro-CTA). For example, a chain-transfer moiety, Y, of a RAFT chain transfer agent can be incorporated onto the ω-end of a polymer chain, P", to form a macro-CTA comprising a polymer compound, and represented by a formula P"—Y. (In such case, the polymer chain, P", can effectively function as a leaving group, $R^L$, of the macromolecular chain transfer agent.) Significantly, additionally or alternatively, a chain-transfer moiety, Y, of a CTA can be incorporated onto the ω-end of a chain-extended polymer chain, P"-(E)$_k$, to form a macro-CTA comprising a polymer chain and a chain extension moiety, and represented by a formula P"-(E)$_k$-Y. (In such case, the chain-extended polymer chain, P"-(E)$_k$ can effectively function as a leaving group, $R^L$, of the macromolecular chain transfer agent.) As used herein, k is an integer ranging from 1 to 20, preferably from 1 to 10.

As incorporated into a compound of the invention, such as into a chain-extended polymer (e.g., P"-(E)$_k$-Y), the moiety, —Y, is referred to as a chain transfer residue. Hence, in the context of compounds of the invention derived from radical polymerization, —Y can be a chain-transfer residue. The chain transfer residue can be derived from controlled (living) radical polymerization of a chain extension monomer under chain extension conditions. Such controlled radical extension reactions can be effected for example in the presence of a chain transfer agent (CTA) such as a RAFT agent (e.g., Y—$R^L$) or such as a macro-CTA (e.g., P"—Y). The chain-transfer residue, —Y, is typically covalently bonded to a chain extension moiety of a chain-extended polymer on the ω-end thereof (also referred to as the living end of the chain extension moiety when included in a macro CTA).

In embodiments, therefore, the moiety —Y in the various compounds of the invention is a chain transfer residue. The chain transfer residue, —Y, can preferably be a thiocarbonylthio moiety having a formula —SC(=S)Z, where Z is an activating group. The activating group, Z, can be —X($R^Z$)a where X is selected from the group consisting of O, N, C and S, $R^Z$ is an activating substituent, and a is an integer equal to 1, 2 or 3, corresponding to the valency of X. For example, where X is O, the chain transfer residue, —Y, can be represented by a formula —SC(=S)O$R^Z$ (xanthates). In another embodiment, where X is N, the chain transfer residue, —Y, can be represented by a formula —SC(=S)NR$^{Z1}$R$^{Z2}$ (dithiocarbamates). In a further embodiment, where X is C, the chain transfer residue, —Y, can be represented by a formula —SC(=S)CR$^{Z1}$R$^{Z2}$R$^{Z3}$ (diothioesters). In an additional embodiment, where X is S, the chain transfer residue, —Y, can be represented by a formula —SC(=S)SR$^Z$ (trithiocarbonates). In each case the activating substituents, R$^Z$, R$^{Z1}$, R$^{Z2}$, or R$^{Z3}$ are not narrowly critical, and are generally selected from hydrogen, substituted or unsubstituted hydrocarbyl, and substituted or unsubstituted hetero-hydrocarbyl. Generally, activating substituents, R$^Z$, R$^{Z1}$, R$^Z$, or R$^{Z3}$ are known in the art, including as described above in connection with RAFT agents. As known in the art, for example, two or more of such activating substituents R$^{Z1}$, R$^{Z2}$, or R$^{Z3}$ can be linked in a cyclic or heterocyclic moiety. One or more of such activating substituents R$^{Z1}$, R$^{Z2}$, or R$^{Z3}$ can represent one bond of a double bond.

Various approaches are known for cleaving and/or derivatizing the chain transfer residue, Y, to form a chain transfer residue derivative. See for example, Moad et al., The Chemistry of Radical Polymerization, 2d Ed., pp. 538 to 539, Elsevier (2006), which is incorporated herein by reference. See also U.S. Pat. No. 6,919,409 to Charmot et al., which discloses cleavage of the thiocarbonylthio control transfer agent.

Although RAFT agents are preferably employed, other controlled (living) radical polymerization methods are also suitable in connection with the invention. See for example, Moad et al., The Chemistry of Radical Polymerization, Elsevier (2006), which is incorporated herein by reference. In particular, atom transfer radical polymerization (ATRP) and stable free radical polymerization (SFRP) approaches are suitable. See Moad et al., Id.

Generally, polymer chains can have a low polydispersity index (PDI) or differences in chain length. Polydispersity index (PDI) can be determined in any suitable manner, e.g., by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity, such as, but not limited to, size exclusion chromatography, dynamic light scattering, matrix-assisted laser desorption/ionization chromatography and electrospray mass chromatography are well known in the art. In some embodiments, block copolymers of the polymeric compounds provided herein have a polydispersity index (PDI) of less than 2.0, or less than 1.5, or less than 1.4, or less than 1.3, or less than 1.2

Generally, polymerization processes described herein optionally occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

Generally, polymerization processes described herein can be effected at temperature effective for the polymerization reaction. Temperatures can be varied based on and in consideration of other reaction aspects, including for example selections as to solvent, monomer (or comonomers) being polymerized (or copolymerized), chain transfer agent, heat transfer (exotherm control), reaction kinetics, and reaction thermodynamics. Typical temperature ranges can generally include a temperature ranging from about 2° C. to about 200° C., preferably from about 20° C. to about 110° C., and in some embodiments from about 40° C. to about 90° C., and or from about 50° C. to about 80° C.

Generally, polymerization processes described herein can be effected at a pressure effective for the polymerization reaction. Generally, reaction pressure is not narrowly critical, and can be at ambient pressure of about 1 atm or at higher pressures (e.g., ranging from 1 atm to about 10 atm) or a lower pressure (e.g., below 1 atm).

Generally, polymerization processes described herein can be effected under a reaction atmosphere effective for the polymerization reaction. For example, polymerization can be effected under an inert gas atmosphere (e.g., Ar, N$_2$), or under ambient atmosphere.

Generally, polymerization processes described herein can be effected at various molar ratios of chain transfer agent (living chain transfer moieties or groups) to monomer effective for the polymerization reaction. For example, polymerization can be effected with a molar ratio of chain transfer agent (groups) to monomer ranging from about 1:1 to about 1:10,000, preferably from about 1:5 to about 1:5000, and most preferably from about 1:10 to about 1:2000 In some embodiments, such molar ratio can range from about 1:10 to about 1:1500.

Generally, polymerization processes described herein can be effected at concentrations of monomer(s) in the solvent ranging from about 5% to about 95% by weight, preferably from about 10% to about 90% solids, by weight, and in some embodiments, from about 20% to about 80% solids, by weight, in each case relative to total weight of solution.

Generally, polymerization processes described herein can be effected at various molar ratios of chain transfer agent (living chain transfer moieties or groups) to initiator effective for the polymerization reaction. For example, polymerization can be effected with a molar ratio of chain transfer agent (groups) to initiator ranging from about 12 to about 50:1, and preferably from about 1:1 to about 40:1, and in some embodiments from about 2:1 to about 30:1.

Generally, polymerization processes described herein can be effected for various reaction times effective for the polymerization reaction. For example, the polymerization can be effected over a reaction time period ranging from about 0.5 hr to about 96 hr, preferably from about 1 hour to about 72 hours, more preferably from about 1 hour to 36 hours, and in some embodiments from about 2 hours to 24 hours, or from about 3 hours to about 12 hours.

Generally, the aforementioned aspects and other factors known in the art can be used to effect the polymerization reaction of interest. See generally, for example, Moad et al., The Chemistry of Radical Polymerization, 2d Ed., Elsevier (2006), which is incorporated herewith in this regard.

Biomolecular Agent

In certain of the various aspects of the invention disclosed or claimed herein (including certain embodiments of each aspect of the invention) the compounds of the invention (or compositions including such compounds) can comprise a polymer conjugate. The polymer conjugate can comprise one or more polymer chains, one or more chain extension moieties and a biomolecular agent covalently linked to the chain extension moiety.

Generally, the biomolecular agent is a biologically relevant moiety. The biomolecular agent can be, for example, a therapeutic agent, a diagnostic agent, a targeting moiety, or an analytical agent. A biomolecular agent can be a therapeutic agent (i.e., a therapeutic moiety) having biological activity and being effective for therapeutic or prophylactic treatment of a disease condition. A biomolecular agent can be a targeting agent (i.e., a targeting moiety) effective for mediating enhanced site-specific directive to a polymeric compound or composition of the invention. A biomolecular agent can be a diagnostic agent (i.e. a diagnostic moiety) effective for evaluating or determining a disease condition. The diagnostic agent can have biological activity relevant to the disease conditioned being evaluated or determined. The diagnostic agent can have an affinity for a biological molecule. The diagnostic agent can be used to evaluate or determine, for example, the presence or absence of, or the relative extent or concentration of a biological molecule which is an indicator the disease condition being evaluated or determined. A biomolecular agent can be an analytical agent (i.e., an analytical moiety) effective for evaluating or determining a biological molecule. The analytical agent can have biological activity relevant to the biological molecule being evaluated or determined. The analytical agent can have an affinity for a biological molecule. The analytical agent can be used to evaluate or determine, for example, the presence or absence of, or the relative extent or concentration of a biological molecule.

In some preferred embodiments (including certain embodiments of each aspect of the invention), the biomolecular agent can be a biological molecule. A biological molecule can include biologically active macromolecules, such as polynucleic acids (e.g., (poly)deoxyribonucleic acids, (poly)ribonucleic acids, etc.), polyamino acids (e.g., peptides, proteins), polysaccharides (e.g., disaccharides, trisaccharides), polyaminoglycosides, and mimetics of the foregoing. Preferred polyamino acids can be hormones, enzymes, or antibodies or antibody fragments. Preferred polynucleic acids can be genomic agents such as DNA or RNA which interact with various aspects related to the expression of proteins from genes in cells. For example, the polynucleotide can be a gene expression modulator, or a knockdown agent. Alternatively for example, the polynucleotide can be a siRNA, RNAi, miRNA, or shRNA. As another example, the polynucleotide can be an antisense oligonucleotide or an aptamer. For example, the polynucleotide can be a dicer substrate. In especially preferred embodiments, the polynucleotide can be a siRNA. The polynucleotide can be a mammalian expression vector. The polynucleotide can be an agent which recombines with and corrects an endogenous gene sequence in a human. In some preferred embodiments, the biological molecules can be an agonist or an antagonist for a biological receptor.

In some preferred embodiments (including certain embodiments of each aspect of the invention), the biomolecular agent can be a small molecule such as a small organic molecule or metallo-organic molecule, preferably having a molecular weight of not more than about 1000 Daltons, preferably not more than about 500 Daltons. In preferred embodiments, the small organic molecules can be an agonist or an antagonist for a biological receptor. In preferred embodiments, the small molecule can be a signaling molecule. As non-limiting examples which can independently be selected in preferred embodiments, small molecules can include alkaloids, glycosides, lipids, flavonoids, non-ribosomal peptides, polyketides, phenazines, phenols, steroids, terpenes, pyrroles, etc.

Hence, provided in certain embodiments herein is a polymer bioconjugate comprising at least one therapeutic agent, at least one diagnostic agent, at least one targeting agent, at least one analytical agent or a combination thereof. Such bioconjugate agents can be covalently coupled to the polymer chain, $P''$, through a covalent bond directly to the extension moiety, or indirectly through a linking moiety.

In some embodiments, a polymer bioconjugate comprises two or more bioconjugate moieties, Q, covalently linked to one or more, or preferably to two or more chain extension moieties (E*).

In some embodiments, the biomolecular agent is a therapeutic agent.

In some embodiments, for example, a polymer bioconjugate comprises a first biomolecular agent which is a first therapeutic agent and a second biomolecular agent which is a second therapeutic agent. In some embodiments, for example, a polymer bioconjugate comprises a first biomolecular agent which is a therapeutic agent and a second biomolecular agent which is a targeting moiety. In specific preferred embodiments, the first therapeutic agent is a polynucleotide which is an active pharmaceutical, and the second therapeutic agent is an (another) active pharmaceutical. In certain embodiments, provided herein is a polymer bioconjugate comprising at least 1-5, 5-250, 5-1000, 250-1000, at least 2, at least 5, at least 10, at least 20, or at least 50 therapeutic agents. In some embodiments, provided herein is a composition comprising a plurality of polymer bioconjugates as described herein, wherein the plurality of polymer bioconjugates comprise, on average, at least 1-5, 5-250, 5-1000, 250-1000, at least 2, at least 5, at least 10, at least 20, or at least 50 therapeutic agents.

In certain embodiments, at least one or more polymer chains, $P''$, comprises an endosomal membrane destabilizing polymer. Such embodiments can be especially adapted for use in connection with intracelluar delivery of therapeutic agents. In such embodiments, for example, a polymeric compound of the invention can comprise one or more polymer chains, $P''$, which comprise an endosomal membrane destabilizing polymer (e.g., a homopolymer, a random copolymer or a block copolymer), a chain extension moiety and one or more therapeutic agents coupled to the chain extension moiety. Further preferred aspects of such embodiments are described hereinafter.

In certain embodiments, a conjugate of one or more therapeutic agent (e.g., oligonucleotide) with a polymeric compound (e.g., a block copolymer compound) provided herein is prepared according to a process comprising the following two steps: (1) activating a modifiable end group (for example, 5'- or 3'-hydroxyl or) of an oligonucleotide using any suitable activation reagents, such as but not limited to 1-ethyl-3,3-dimethylaminopropyl carbodiimide (EDAC), imidazole, N-hydroxysuccinimide (NHS) and dicyclohexylcarbodiimide (DCC), HOBt (1-hydroxybenzotriazole), p-nitrophenylchloroformate, carbonyldiimidazole (CDI), and N,N'-disuccinimidyl carbonate (DSC); and (2) covalently linking a block copolymer to the end of the oligonucleotide. In some embodiments, the 5'- or 3'-end modifiable group of an oligonucleotide is substituted by other functional groups prior to conjugation with the block copolymer. For example, hydroxyl group (—OH) is optionally substituted with a linker carrying sulfhydryl group (—SH), carboxyl group (—COOH), or amine group (—NH$_2$).

In yet another embodiment, an oligonucleotide comprising a functional group introduced into one or more of the bases (for example, a 5-aminoalkylpyrimidine), is conjugated to a polymeric compound (e.g., block copolymer), provided herein using an activating agent or a reactive bifunctional linker according to any suitable procedure. A variety of such activating agents and bifunctional linkers is available commercially from such suppliers as Sigma, Pierce, Invitrogen and others.

In some embodiments, the therapeutic agent is a proteinaceous agent. Polypeptide functional groups that are usually involved include but are not limited to amino, hydroxy, thiol, or carboxyl groups. Such groups can be present as a terminal group or present on the amino acid side chains. In some embodiments, the proteinaceous therapeutic agents are engineered to contain non-natural amino acids comprising special functional groups for formation of site-specific conjugates, e.g., azido groups for conjugation via "click" chemistry.

In some embodiments, a biomolecular agent provided in connection with the polymeric compounds of the invention can be a diagnostic agent.

In alternative embodiments, diagnostic agents (such as described above) can be non-covalently associated with the polymeric compounds provided herein by complexing with a chelating residue (e.g., a carboxylic acid residue) incorporated into one or more polymer chains. In some embodiments, a radiolabeled monomer (e.g., a $^{14}$C-labeled monomer) is incorporated into the polymeric compounds. In some embodiments, a polymeric compound associated with a diagnostic agent comprises a targeting moiety.

In each of such foregoing embodiments, the diagnostic agent can be a diagnostic imaging agent, e.g., an agent useful in imaging the mammalian vascular system which includes but is not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{14}$C, or the like, fluorescently labeled compounds, or their complexes, chelates, adducts and conjugates. In other embodiments, the diagnostic agent is a marker gene that encode proteins that are readily detectable when expressed in a cell (including, but not limited to, -galactosidase, green fluorescent protein, luciferase, and the like) and labeled nucleic acid probes (e.g., radiolabeled or fluorescently labeled probes).

In certain embodiments, polymeric compounds described herein comprise at least one targeting moiety (e.g., a moiety that targets a specific cell or type of cell), for example as a biomolecular agent, Q, as described above.

In some embodiments, the bioconjugate moiety can be a targeting moiety, having a specific affinity for one or more biological receptors or other compounds or cell surfaces of interest. In some preferred embodiments, a targeting moiety can be a ligand having affinity for one or more receptors effective for mediating cell uptake, e.g., via endocytosis.

In some embodiments, the biomolecular agent can be a targeting moiety adapted for interaction with other compounds of interest, e.g., such as a one or more therapeutic agents. Such bioconjugate moieties can effect interaction with one or more therapeutic agent and/or polymers that have an affinity for one another, such as biotin-streptavidin, arylboronic acid-salicyihydroxamic acid, leucine zipper or other peptide motifs, ionic interactions between positive and negative charges on the polymeric compound and therapeutic agent, or other types of non-covalent chemical affinity linkages. For example, an affinity binder pair, such as biotin/avidin pair used for preparation of biomolecular complexes, is optionally employed for non-covalent attachment of biotin-modified therapeutic agent to avidin-modified polymeric compounds. Additionally, in some embodiments, a double-stranded polynucleotide is associated with (e.g., complexed to) a polymeric compound of the invention. In some embodiments, a polymeric compound can be non-covalently associated (e.g., non-covalently complexed) with a nucleic acid minor groove binding agent or an intercalating agent which itself is attached (e.g., covalently) to an extension moiety of a polymeric compound.

In specific instances, the polymeric compounds provided herein are useful for delivery of therapeutic agents to specifically targeted cells of an individual. In certain instances, the efficiency of the cell uptake of the polymeric compounds is enhanced by incorporation of targeting moieties covalently bonded to the polymeric compounds. In the context of cell uptake, a targeting moiety (targeting agent) is an affinity reagent which recognizes the surface of a cell (e.g., a select cell). In some embodiments, targeting moieties recognize a cell surface antigen or bind to a receptor on the surface of the target cell. Suitable targeting moieties include, by way of non-limiting example, antibodies, antibody-like molecules, or peptides, such as an integrin-binding peptides such as RGD-containing peptides, or small molecules, such as vitamins, e.g., folate, sugars such as lactose and galactose, or other small molecules. Cell surface antigens include a cell surface molecule such as a protein, sugar, lipid or other antigen on the cell surface. In specific embodiments, the cell surface antigen undergoes internalization. Examples of cell surface antigens targeted by the targeting moieties of the polymeric compounds provided herein include, but are not limited, to the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, and the asialoglycoprotein receptor.

Targeting moieties can be covalently attached, in various embodiments, to a polymeric compound (e.g., block copolymer compound), preferably for example through a side chain of a chain extension residue monomeric unit, or otherwise incorporated, preferably in each case where the chain extension moiety is provided at a terminal end of a polymeric compound or between two polymer chains of a polymeric compound. Attachment of the targeting moiety to the polymer chain can be achieved in any suitable manner, e.g., by any one of a number of conjugation chemistry approaches including but not limited to a linking moiety as described below.

In alternative embodiments, targeting ligands are attached to a monomer residue of the polymer chain, and the resulting compound is then used in the polymerization synthesis of a polymer (e.g., block copolymer) as described herein. In some embodiments, targeting moieties are covalently bonded to a block of a first block copolymer, or to a block of a second block copolymer. In some embodiments, the targeting moieties are attached to the sense or antisense strand of siRNA covalently bound to non-covalently associated with a polymeric compound. In certain embodiments, the targeting agent is attached to a 5' or a 3' end of the sense or the antisense strand.

In specific embodiments, the polymeric compounds provided herein are biocompatible. As used herein, "biocompatible" refers to a property of a polymer characterized by it, or its in vivo degradation products, being not, or at least minimally and/or reparably, injurious to living tissue; and/or not, or at least minimally and controllably, causing an immunological reaction in living tissue. With regard to salts, it is presently preferred that both the cationic and the anionic species be biocompatible. As used herein, "physiologically acceptable" is interchangeable with biocompatible. In some instances, the polymer chains used therein (e.g., block copolymers) exhibit low toxicity compared to cationic lipids.

In some instances, one or more of the polymer chains (e.g., block copolymers) utilized in polymeric compounds described herein comprise polyethyleneglycol (PEG) chains or blocks with molecular weights of approximately from 1,000 to approximately 30,000. In some embodiments, PEG is conjugated to polymer ends groups, or to one or more pendant modifiable group present in a polymeric compound provided herein. In some embodiments, PEG residues are conjugated to modifiable groups within the hydrophilic segment or block (e.g., a shell block) of a polymer (e.g., block copolymer) of a polymeric compound provided herein. In certain embodiments, a monomer comprising a PEG residue is co-polymerized to form the hydrophilic portion of a polymer chain of a polymeric compound provided herein.

Linking Moiety

Generally, the biomolecular agent can be linked to the chain extension moiety through one or more linking moieties.

The linking moiety can be a covalent bond.

The linking moiety can be a multifunctional (e.g., difunctional) moiety, such as a hydrocarbyl, substituted hydrocarbyl, hetero-hydrocarbyl or substituted heterohydrocarbyl, in each case comprising two or more reactive functional groups. In some embodiments, the linking moiety comprises a cleavable bond, e.g. a bond that is unstable and/or is cleaved upon changes in certain intracellular parameters (e.g., pH or redox potential). For example, the linking moiety can be a disulfide linking moiety L. For example, the linking moiety can be an acid-labile linking moiety L. In some preferred embodiments, the linking moiety L can comprise at least one bond which is acid labile at an endosomal pH.

In some embodiments, a biomolecular agent (e.g., an oligonucleotide) is conjugated to an extension moiety of the polymeric compound by a suitable chemical conjugation approach. In some embodiments, the covalent bond between an extension moiety and a biomolecular agent can be optionally, non-cleavable, or cleavable. In certain embodiments, a precursor of one or more RNAi agent (e.g. a dicer substrate) is attached to the polymeric compound by a non-cleavable bond. In some embodiments, one or more RNAi agent is attached through a cleavable bond. In certain embodiments, the cleavable bonds utilized in such approach include, by way of non-limiting example, disulfide bonds (e.g., disulfide bonds that dissociate in the reducing environment of the cytoplasm).

Linking moieties can include, for example, amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In specific embodiments, "click" chemistry is used to attach the bioconjugate such as a targeting ligand to the polymeric compounds (e.g., a block copolymer) as provided herein (for example of "click" reactions, see Wu, P.; Fokin, V. V. Catalytic Azide-Alkyne Cycloaddition: Reactivity and Applications. *Aldrichim. Acta* 2007, 40, 7-17). A large variety of conjugation chemistries are optionally utilized (see, for example, *Bioconjugation*, Aslam and Dent, Eds, Macmillan, 1998 and chapters therein). In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, *Bioconjugation*, Aslam and Dent, Eds, Macmillan, 1998 and chapters therein).

Polynucleotide-Containing Compositions and Uses Thereof

As described herein, the polymeric compounds of the invention can comprise polynucleotide(s) or can be a constituent component of compositions comprising polynucleotide(s). The polynucleotides can be covalently bonded to (e.g., as biomolecular agent), or non-covalently associated with the polymeric compounds of the invention. Such compounds and compositions are especially suitable for delivery of polynucleotides (e.g., RNAi) into a cell, in-vitro, or in-vivo in an individual in need thereof.

Generally, the compositions can include polynucleotide-containing compositions, where such compositions comprise a polymeric compound and a polynucleotide associated therewith, the polymeric compound comprising a polymer having a formula IIA

$$P''\text{-}(E)_K\text{-}[Y,Y^* \text{ or } P''']\qquad\qquad(\text{IIA}),$$

where each of $P''$, $E$, $k$, $Y$, $Y^*$ and $P'''$ is as described above in connection with Formula IIA or Formula IA (e.g., including where E is a chain extension residue comprising one or more bioconjugate moieties, Q, covalently linked thereto, e.g., through a linking moiety, L), In some embodiments, the polynucleotide can be covalently linked to the polymeric compound. For example, the polynucleotide can be covalently bonded to a chain extension residue, E, of one or more of the chain extension moieties, (E*), in each case through an independently selected linking moiety, L. Without limitation, as depicted in FIG. 7C through FIG. 7G, for example, compounds and compositions of the invention can comprise a polymeric compound comprising a polynucleotide (shown as RNAi) conjugated to an extension residue, (E*), of a polymer having a formula IIA, e.g., through a linking moiety, L (not shown). In some depicted embodiments (FIGS. 7D, 7F, 7G), the polymeric compound further comprises one or more targeting moieties (e.g., shown as triangles) covalently conjugated thereto, for example through an extension moiety (E*) or through another functional group (e.g., an α-end functional group as shown in FIG. 7D).

In some embodiments, the polynucleotide can be associated with the polymeric compounds through non-covalent interactions with the polymeric compound (e.g., through ionic interactions therewith). For example, the polymeric compounds of Formula IIA can comprise a polymer chain(s) which includes one or more monomeric residues adapted for non-covalent association with a polynucleotide. In one non-limiting approach, for example, the polymeric compounds can comprise a polymer chain(s) which include one or more monomeric residues having cationic (chargeable) species. Such polycationic character provides a basis for non-covalent association, which includes ionic association, with polynucleotides. Without limitation, as depicted in FIG. 7A and FIG. 7B, for example, a polymeric compound comprising a diblock copolymer can have a polynucleotide (shown as RNAi) associated therewith by ionic interactions with at cationic block of the copolymer. In one depicted embodiment (FIG. 7B), the polymeric compound further comprises one or more targeting moieties (e.g., shown as a triangle) covalently conjugated thereto, for example through an extension moiety (E*). As an example, such polymeric compound can associate with a mammalian expression vector DNA and complex the DNA.

In some embodiments, the polymeric compound-polynucleotide complex is charge neutralized (e.g., the one or more polymer chains of the polymeric compound and the polynucleotide are substantially charge neutralized, considered as a whole). Depending on the length of the polynucleotide, the length of the polycationic polymer chain(s) can be adjusted to provide charge neutralization for the polynucleotide of interest. In some instances, charge-neutralization can be achieved or further tuned by addition of cations and/or polycations into a formulation comprising the polymeric compounds.

In certain embodiments, including in combination with either of the aforedescribed embodiments in which polynucleotides are covalently bonded to (e.g., as biomolecular agent), or are non-covalently associated with the polymeric compounds of the invention, the polymeric composition can comprise at least one or more polymer chains, $P^n$, which comprise an endosomal membrane destabilizing polymer. Generally in this regard, the polymeric compounds of such compositions can preferably comprise at least one membrane disruptive polymer chain (e.g., a pH sensitive polymer having membrane disrupting activity at endosomal pH).

Preferably in this regard, for example, the polymeric compounds of such compositions can preferably comprise at least polymer chain which is hydrophobic. Preferably in this regard, the polymeric compounds of such compositions can preferably comprise at least one polymer chain which includes a plurality of monomeric residues having a first chargeable species, the first chargeable species being anionic at serum physiological pH, and being substantially neutral or non-charged at an endosomal pH.

Preferably, in this regard, for example, the polymeric compounds of such compositions can preferably comprise at least one polymer chain which includes (i) a plurality of hydrophobic monomeric residues, and (ii) a plurality of monomeric residues having a first chargeable species, the first chargeable species being anionic at serum physiological pH, and being substantially neutral or non-charged at an endosomal pH.

In some embodiments, membrane destabilizing block copolymers provided herein are membrane destabilizing at any suitable pH. In some embodiments, the membrane destabilizing block copolymers are membrane destabilizing (e.g., in an aqueous medium) at an endosomal pH. In some embodiments, the membrane destabilizing block copolymers are membrane destabilizing (e.g., in an aqueous medium) at a pH of about 6.5, or lower, about 5.0 to about 6.5, or about 6.2, or lower.

As a general, non-limiting example, a composition can comprise polymeric compounds which comprise a block copolymer, and a polynucleotide associated therewith, where the block copolymer comprises one or more polymer chains, $P^n$, which comprise an endosomal membrane destabilizing polymer. For example, in one orientation, the block copolymer can preferably comprise a first polymer chain defining a first block A of the copolymer, and a second membrane disruptive polymer chain defining a second block B of the copolymer. For example, the block copolymer can comprise a first polymer chain defining a first block A of the copolymer, and a second polymer chain defining a second block B of the copolymer which includes (i) a plurality of hydrophobic monomeric residues, and (ii) a plurality of monomeric residues having a first chargeable species, the first chargeable species being anionic at serum physiological pH, and being substantially neutral or non-charged at an endosomal pH. For example, in an alternative orientation, the block copolymer can preferably comprise a first membrane disruptive polymer chain defining a first block A of the copolymer, and a second polymer chain defining a second block B of the copolymer. For example, the block copolymer can comprise a first polymer chain defining a first block A of the copolymer and which includes (i) a plurality of hydrophobic monomeric residues, and (ii) a plurality of monomeric residues having a first chargeable species, the first chargeable species being anionic at serum physiological pH, and being substantially neutral or non-charged at an endosomal pH, and a second polymer chain defining a second block B of the copolymer.

Further in connection with the immediately foregoing block copolymer embodiment, a polynucleotide can be covalently linked to the polymeric compound, for example covalently bonded to a chain extension residue, E, of one or more of the chain extension moieties, (E*)—including for example to a junctional chain extension moiety between the first block A and the second block B, or to a terminal extension moiety (e.g., located at the ω-terminal end of the polymeric compound.

Alternatively, and further in connection with the foregoing block copolymer embodiment, a polynucleotide can be non-covalently associated with the polymeric compound, for example through interactions with the second block B of such polymeric compound. For example, in this regard the block copolymer can comprise a second polymer chain defining a second block B of the copolymer which includes a plurality of monomeric residues having a cationic species at serum physiological pH, wherein the polynucleotide is associated with the block copolymer through non-covalent interactions between the polynucleotide and the cationic species of the second block B of the copolymer.

Generally, including in combination with either of the aforedescribed embodiments in which polynucleotides are covalently bonded to (e.g., as biomolecular agent), or are non-covalently associated with the polymeric compounds of the invention, and in the various embodiments for various polymer chains (e.g., the aforementioned block copolymer example), the polymeric compounds of such compositions can further comprise one or more targeting moieties covalently bonded to the polymeric compounds (e.g., covalently bonded to a chain extension residue E of one or more of the chain extension moieties, (E*), in each case through an independently selected linking moiety, L). Generally, and preferably in this regard, such targeting moiety can be a ligand having affinity for one or more receptors effective for mediating endocytosis.

Especially preferred are such embodiments which include one or more polymer chains, $P^n$, comprising an endosomal membrane destabilizing polymer, and/or comprising a conjugate moiety, Q, which is a targeting moiety which is a ligand having affinity for one or more receptors effective for mediating endocytosis. These embodiments can be especially adapted for use in connection with intracelluar delivery of therapeutic agents, such as polynucleotides. In such embodiments, for example, a polymeric compound of the invention can comprise one or more polymer chains, P'', which comprise an endosomal membrane destabilizing polymer (e.g., a homopolymer, a random copolymer or a block copolymer), and one or more chain extension moieties (E*). In one approach, one or more polynucleotides can be covalently coupled to the chain extension moiety, as described. In an alternative approach, one or more polynucleotide can be non-covalently associated with the polymeric compound, as described.

In any of the aforementioned embodiments, the composition can comprise a plurality of the polymeric compounds in a micellic assembly. Such micellic assembly can comprise a core defined by an association of the first hydrophobic polymer chains, P''', of the plurality of polymeric compounds, and a shell defined by the second polymer chains, P''', of the plurality of polymeric compounds. The polynucleotides of interest can be covalently bonded to (e.g., as biomolecular agent) to one or more of the polymeric compounds of the micellic assembly, or alternatively, polynucleotides can be non-covalently associated with the polymeric compounds of the micellic assembly, in each using approaches as described herein. In some such embodiments, the micellic assembly can be a nanoparticle (e.g., a micelle) comprising a core, a shell and one or more polynucleotide. Preferably, the polynucleotide is not in the core of the micellic assembly.

In specific embodiments, the block copolymer (e.g., membrane destabilizing block copolymer) is a diblock copolymer, having the chemical formula:

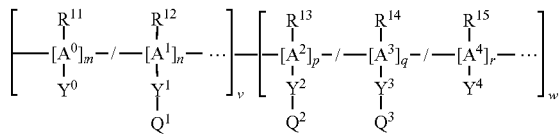

wherein:
A$^0$, A$^1$, A$^2$, A$^3$ and A$^4$ are selected from the group consisting of —C—, —C—C—, —C(O)(CR$^6$R$^7$)$_a$C(O)O—, —O(CR$^6$R$^7$)$_a$C(O)— and O(CR$^6$R$^7$)$_b$O;
wherein,
a is 1-4;
b is 2-4;
Y$^0$ and Y$^4$ are independently selected from the group consisting of hydrogen, (1C-10C)alkyl, (3C-6C)cycloalkyl, O(1C-10C)alkyl, O(2C-50C)heteroalkyl, —C(O)O(1C-10C)alkyl, C(O)O(2C-100C)heteroalkyl, C(O)NR$^8$(1C-10C)alkyl, C(O)NR$^8$(2C-100C)heteroalkyl, (5C-10C)aryl, (4C-10C)heteroaryl, any of which is optionally substituted with one or more fluorine, cyano or azido groups;
Y$^1$ and Y$^2$ are divalent linkers and are independently selected from the group consisting of a covalent bond, (1C-10C)alkyl-, —C(O)O(2C-10C) alkyl-, —OC(O)(1C-10C) alkyl-, —O(2C-10C) alkyl- and —S(2C-10C) alkyl- —C(O)NR$^8$(2C-10C) alkyl, (5C-10C)aryl, (4C-10C)heteroaryl, any of which is optionally substituted with one or more fluorine, cyano or azido groups;

Y$^3$ is a divalent linker and is selected from the group consisting of a covalent bond, (1C-10C)alkyl and (6C-10C)aryl;
wherein tetravalent carbon atoms of A$^1$—A$^4$ that are not fully substituted with R$^1$—R$^5$ and Y$^0$—Y$^4$ are completed with an appropriate number of hydrogen atoms;
R$^{11}$, R$^{12}$, R$^{13}$, R$^{14}$, R$^{15}$, R$^6$, R$^7$ and R$^8$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;
Q$^1$ and Q$^2$ are residues which are positively charged at physiologic pH, including but not limited to amino, alkylamino, ammonium, alkylammonium, guanidine, imidazolyl, and pyridyl.
Q$^3$ is a residue which is negatively charged at physiologic pH, but undergoes protonation at lower pH, including but not limited to carboxyl, sulfonamide, boronate, phosphonate, and phosphate group;
m, n, p, q and r denote molar proportions of monomeric units in a given block, and wherein
m+n=1;
p+q+r=1;
v and w signify molecular weight of each block, and wherein
v is from about 5 to about 25 kDa; and,
w is from about 5 to about 50 kDa.

In certain embodiments, the block copolymer is a diblock copolymer, having the chemical formula (at normal physiological pH):

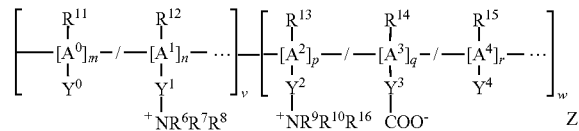

wherein:
A$^0$, A$^1$, A$^2$, A$^3$ and A$^4$ are selected from the group consisting of —C—, —C—C—, —C(O)(CR$^{17}$R$^{18}$)$_a$C(O)O—, —O(CR$^{17}$R$^{18}$)$_a$C(O)— and O(CR$^{17}$R$^{18}$)$_b$O;
wherein,
a is 1-4;
b is 2-4;
R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ are independently selected from the group consisting of hydrogen, (1C-5C)alkyl, (3C-6C)cycloalkyl, (5C-10C)aryl, (4C-10C)heteroaryl, any of which may be optionally substituted with one or more fluorine atoms;
Y$^0$ and Y$^4$ are independently selected from the group consisting of hydrogen, (1C-10C)alkyl, (3C-6C)cycloalkyl, O-(1C-10C)alkyl, —C(O)O(1C-10C)alkyl and phenyl, any of which is optionally substituted with one or more fluorine groups;
Y$^1$ and Y$^2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl-;

$Y_3$ is selected from the group consisting of a covalent bond, (1C-5C)alkyl and phenyl; wherein tetravalent carbon atoms of $A^1$—$A^4$ that are not fully substituted with $R^{11}$—$R^{15}$ and $Y^0$—$Y^4$ are completed with an appropriate number of hydrogen atoms;

Z is a physiologically acceptable counterion, m is 0 to about 0.49;

n is about 0.51 to about 1.0; wherein m+n=1 p is about 0.2 to about 0.5;

q is about 0.2 to about 0.5; wherein:

p is substantially the same as q;

r is 0 to about 0.6; wherein p+q+r=1 v is from about 5 to about 25 kDa; and, w is from about 5 to about 50 kDa.

In some embodiments:

$A^1$ is —C—C—

$Y^1$ is —C(O)OCH$_2$CH$_2$—;

$R^6$ is hydrogen;

$R^7$ and $R^8$ are each —CH$_3$; and, $R^{12}$ is —CH$_3$.

In some embodiments:

$A^2$ is —C—C—;

$Y^2$ is —C(O)OCH$_2$CH$_2$—;

$R^9$ is hydrogen;

$R^{10}$ and $R^{16}$ are each —CH$_3$; and, $R^{13}$ is —CH$_3$.

In some embodiments, $A^3$ is —C—C—;

$R^{14}$ is CH$_3$CH$_2$CH$_2$—;

$Y^3$ is a covalent bond; and

Z$^-$ is a physiologically acceptable anion.

In some embodiments:

$A^4$ is —C—C—;

$R^{15}$ is selected from the group consisting of hydrogen and —CH$_3$; and, $Y^4$ is —C(O)O(CH$_2$)$_3$CH$_3$.

In some embodiments, $A^0$ is C—C—

$R^{11}$ is selected from the group consisting of hydrogen and (1C-3C)alkyl; and, $Y^0$ is selected from the group consisting of —C(O)O(1C-3C)alkyl.

In some embodiments, m is 0. In some embodiments, r is 0. In some embodiments, m and r are both 0.

In some embodiments, a polymeric compound can be a membrane destabilizing block copolymer compounds, as described herein, and can comprise a first polymer chain defining a first block of the copolymer, and a second polymer chain defining a second block of the copolymer.

Such first polymer chain can include monomeric residues having at least one first chargeable species, and monomeric residues having at least one second chargeable species. Each of the first chargeable species, and the second chargeable species, is charged or chargeable to one of either anionic species or cationic species. In some embodiments, the polymeric compound can optionally comprise at least one additional non-chargeable and/or hydrophobic species. The variable chargeable species provides an opportunity to tune the charge profile of the first block of the copolymer.

For example, such first polymer chain can be a random copolymer block which comprises at least one anionic chargeable species, at least one cationic chargeable species, and optionally at least one additional non-chargeable and/or hydrophobic species.

The first chargeable species of the first polymer chain can be a Bronsted acid. In some embodiments, the first chargeable species are at least 50%, at least 60%, at least 70%, at least 80%, at least 85%, or at least 95% negatively charged at about physiological pH (e.g., at a pH of about 7.4). In specific embodiments, these first chargeable species, units are charged by loss of an H$^+$, to an anionic species at about neutral pH. The pKa of the first chargeable species can be such that at a different pH, the first chargeable species, of the first block are species that are at least 20%, at least 30%, at least 40%, at least 50%, at least 60%, at least 70%, at least 80%, at least 85%, or at least 95% neutral or non-charged at a slightly acidic pH (e.g., a pH of about 6.5, or less; about 6.2, or less; about 6, or less; about 5.9, or less; about 5.8, or less; or at about an endosomal pH).

The first chargeable species or group is, by way of non-limiting example, a carboxylic acid, anhydride, sulfonamide, sulfonic acid, sulfinic acid, sulfuric acid, phosphoric acid, phosphinic acid, boric acid, phosphorous acid, or the like. Similarly, in certain embodiments, a first chargeable monomeric residue comprises a carboxylic acid, anhydride, sulfonamide, sulfonic acid, sulfinic acid, sulfuric acid, phosphoric acid, phosphinic acid, boric acid, phosphorous acid, or the like.

In some embodiments, the anionic chargeable species is any organic or inorganic acid residue that is optionally present, either as a protected species, e.g., an ester, or as the free acid, in the selected polymerization process. In some embodiments, the anionic chargeable species is a weak acid, such as but not limited to the following groups: boronic acid, sulfonamide, phosphonic acid, arsonic acid, phosphinic acid, phosphate, carboxylic acid, xanthenes, tetrazole or their derivatives (e.g. esters). In certain embodiments monomers such as maleic-anhydride, (Scott M. Henry, Mohamed E. H. El-Sayed, Christopher M. Pirie, Allan S. Hoffman, and Patrick S. Stayton pH-Responsive Poly(styrene-alt-maleic anhydride) Alkylamide Copolymers for Intracellular Drug Delivery. *Biomacromolecules* 2006, 7, 2407-2414) are used for introduction of first chargeable species by post-polymerization hydrolysis of the maleic anhydride monomeric units.

A preferred first chargeable monomeric residue is derived from a (C$_2$-C$_5$)alkylacrylic acid monomer. In specific embodiments, a chargeable species that are anionic at normal physiological pH are carboxylic acids such as, but not limited to, 2-propyl acrylic acid or, more accurately, the constitutional unit derived from it, 2-propylpropionic acid, —CH$_2$C((CH$_2$)$_2$CH$_3$)(COOH) (PAA).

The second chargeable species of the first polymer chain can be a Bronsted base. The second chargeable species of the first polymer chain are at least 20%, at least 30%, at least 40%, at least 50%, at least 60%, at least 70%, at least 80%, at least 85%, or at least 95% positively charged at about physiological pH (e.g., at a pH of about 7.4). In specific embodiments, these second chargeable species are charged by addition of an H$^+$, to a cationic species. The pKa of the second chargeable species can be such that at a different pH, the second chargeable species are at least 20%, at least 30%, at least 40%, at least 50%, at least 60%, at least 70%, at least 80%, at least 85%, or at least 95% positively charged at a slightly acidic pH (e.g., a pH of about 6.5, or less; about 6.2, or less; about 6, or less; about 5.9, or less; about 5.8, or less; or about endosomal pH).

The second chargeable species can be, in some embodiments, an amine (including, e.g., non-cyclic and cyclic amines), for example, as an amine moiety of a monomeric residue.

A preferred second chargeable species of the first polymer can be a monomeric residue comprising an amine, such as a monomeric residue derived from a monomer selected from N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, or N,N-di($C_1$-$C_6$)alkyl-amino($C_1$-$C_6$)alkyl-acrylate. In some embodiments, the second chargeable monomeric unit can comprise a nitrogen heterocycle, e.g. an imidazole, a pyridine, a piperidine, a pyrimidine, or the like.

The second chargeable species, which is cationic at physiological pH species, can be nitrogen-containing species such as ammonium, —NRR'R", guanidinium (—NRC(—NR'H)$^+$NR"R'", including canonical forms), wherein the R groups are independently hydrogen, alkyl, cycloalkyl or aryl or two R groups bonded to the same or adjacent nitrogen atoms may be also be joined to one another to form a heterocyclic species such as but not limited to pyrrole, imidazole, pyrimidine, or indole.

In some embodiments, the first and/or second chargeable species is present in a zwitterionic monomeric units (i.e., wherein an anionic and a cationic chargeable species are present in the same monomeric unit).

The first block comprises at least one non-chargeable species. In some embodiments, the non-chargeable species is a hydrophobic species (e.g., comprises a hydrophobic group). In certain embodiments, the hydrophobic group has a π value of about 1, or more; about 2, or more; about 3, or more; about 4, or more; about 5, or more; or the like.

The non-chargeable monomeric residues of the first chain can be for example, a ($C_2$-$C_8$)alkyl-ethacrylate, a ($C_2$-$C_7$)alkyl-methacrylate, or a ($C_2$-$C_8$)alkyl-acrylate.

In some embodiments, the first block of the block copolymer comprises a plurality of hydrophobic species. In certain embodiments, the hydrophobic monomeric unit is a vinyl substituted aromatic or hereoaromatic compound. In further specific embodiments, hydrophobic monomers are alkyl (alkyl)acrylates. In specific embodiments, the hydrophobic monomer is a styrene derivative.

The first block of the membrane destabilizing block copolymer can have a number average molecular weight (Mn) of about 2,000 dalton to about 250,000 dalton; about 5,000 dalton to about 100,000 dalton; about 5,000 dalton to about 50,000 dalton; or about 10,000 dalton to about 50,000 dalton.

The second polymer chain defining a second block of a membrane destabilizing block copolymer described herein can be hydrophilic. In some embodiments, the second block of a membrane destabilizing polymer described herein can be hydrophilic and can be charged at an approximately physiological pH, e.g. pH 7.4. In specific embodiments, the second block of the membrane destabilizing polymer comprises at least one chargeable species. In specific embodiments, the chargeable species is charged or chargeable to a cationic species. In other specific embodiments, the chargeable species is charged or chargeable to an anionic species. In other embodiments, none of the monomeric residues comprise charged species.

The second polymer chain of the second block of one or more of the membrane destabilizing block copolymers can be polycationic at about neutral pH (e.g., at a pH of about 7.4).

The second block of one or more of the membrane destabilizing block copolymers can be a homopolymeric block. In certain embodiments, a homopolymeric second block comprises cationic chargeable monomeric units, wherein some of the cationic chargeable monomeric units are cationic and wherein others of the cationic chargeable monomeric units are non-charged. In further or alternative embodiments, the second block of one or more of the membrane destabilizing block copolymers is heteropolymeric. In specific embodiments, a heteropolymeric second block comprises cationic chargeable monomeric units and non-chargeable monomeric units.

The chargeable monomeric residue of the second block can be a Bronsted base. The chargeable species of the second polymer chain defining the second block of the membrane destabilizing block copolymers are species that are at least 20%, at least 30%, at least 40%, at least 50%, at least 60%, at least 70%, at least 80%, at least 85%, or at least 95% positively charged at about neutral pH (e.g., at a pH of about 7.4). In specific embodiments, these chargeable species in the second block are charged by addition of an $H^+$, to a cationic species. The pKa of such chargeable species can be such that, the chargeable species, in the second polymer chain are species that are at least 20%, at least 30%, at least 40%, at least 50%, at least 60%, at least 70%, at least 80%, at least 85%, or at least 95% positively charged at a slightly acidic pH (e.g., a pH of about 6.5, or less; about 6.2, or less; about 6, or less; about 5.9, or less; about 5.8, or less; or about endosomal pH).

In certain embodiments, the chargeable species or group of the second block is an amine (including, e.g., non-cyclic and cyclic amines).

A preferred chargeable monomeric residue of the second block is a monomeric residue comprising an amine, such as, by way of non-limiting example, a monomeric residue derived from a monomer selected from N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, or N,N-di($C_1$-$C_6$)alkyl-amino($C_1$-$C_6$)alkyl-acrylate. In some embodiments, the chargeable monomeric unit of the second block is a monomeric unit comprising a nitrogen heterocycle, e.g., an imidazole or pyridine.

The chargeable species of the second polymer chain, which can be cationic at physiological pH, can be nitrogen species such as ammonium, —NRR'R", guanidinium (—NRC(=NR'H)$^+$NR"R'", including canonical forms) wherein the R groups are independently hydrogen, alkyl, cycloalkyl or aryl or two R groups bonded to the same or adjacent nitrogen atoms may be also be joined to one another to form a heterocyclic species such as but not limited to pyrrole, imidazole, or indole. In some embodiments, the second block is a nucleic-acid binding polyamide, an intercalator, or a duplex- or triplex-forming oligonucleotide.

The chargeable species of the second polymer chain can be present in a zwitterionic monomeric units (i.e., wherein an anionic and a cationic chargeable species are present in the same monomeric unit).

The second block can be cationic at or near physiological pH (e.g., the pH of circulation human plasma). In some embodiments, the second block comprises a polycation. In some embodiments, the second block is attached to a therapeutic agent (e.g., a polynucleotide, such as siRNA) which is a polyanion comprising x anions, and the polycationic second block comprises about 0.6 x, about 0.7·x, about 0.8 x, about 0.9 x, about 1.0 x, about 1.1 x cations, or more. In specific embodiments, the therapeutic agent (e.g., a polynucleotide, such as siRNA) is polyanionic comprising x anions, and the polycationic second block comprises about 0.7·x cations, or more.

In an alternative approach, the second polymer chain defining the second block of the membrane destabilizing block copolymer can be non-charged and hydrophilic at about neutral pH (e.g., at a pH of about 7.4). In certain embodiments, the hydrophilic second block is free or substantially free of chargeable groups. In some embodiments, a non-charged hydrophilic second block comprises or is polyethylene glycol (PEG), polyethylene oxide (PEO), poly (alkylene oxide) or the like.

The polymer chain defining the second block of the membrane destabilizing block copolymer can have a number average molecular weight (Mn) of about 1,000 dalton to about 200,000 dalton; about 3,000 dalton to about 100,000 dalton; about 5,000 dalton to about 50,000 dalton; about 5,000 dalton to about 25,000 dalton; or about 5,000 dalton to about 20,000 dalton.

In certain embodiments, the second block of the membrane destabilizing block copolymer comprises a functionalizing group (e.g., a solubilizing group). In specific embodiments, the functionalizing group is a polyethylene glycol (PEG) group. In certain embodiments, the second block comprises a polyethylene glycol (PEG) groups, chains or blocks with molecular weights of approximately from 1,000 to approximately 30,000. In some embodiments, the PEG is a part of (e.g., incorporated into) the second block chain. In certain embodiments, the PEG is incorporated into the second block chain during polymerization. In some embodiments, the second block of one or more of the membrane destabilizing block copolymers is PEG. In certain embodiments, provided herein are micellic assemblies comprising a first membrane destabilizing block copolymer with a polycationic second block, and a second membrane destabilizing block copolymer with a PEG second block. In certain embodiments, one or more monomeric units of the second block are substituted or functionalized with a PEG group. In some embodiments, PEG is conjugated to block copolymer ends groups, or to one or more pendant modifiable group present in polymeric compound provided herein. In some embodiments, PEG residues are conjugated to modifiable groups within the hydrophilic segment or block (e.g., a second block) of a polymer (e.g., block copolymer) of a polymeric compound provided herein. In certain embodiments, a monomer comprising a PEG residue is co-polymerized to form the hydrophilic portion of the polymer forming the polymeric compound provided herein.

In certain embodiments, a polymeric compound can be a block copolymer. In one orientation, the block copolymer can comprise a first polymer chain, P″, which can preferably include poly(DMAEMA) (e.g., as a first block of the block copolymer), a second polymer chain, P‴, which can preferably include a random copolymer comprising monomeric residues derived from polymerization of BMA, DMAEMA and PAA (e.g., as a second block of the block copolymer), and a chain extension (E*) comprising one or more chain extension residue(s), $E_k$ between the first chain, P″, and the second chain, P‴, where k is an integer ranging from 1 to 20, preferably 1 to 10, as described herein. For example, poly (BMA/DMAEMA/PAA) can be prepared by copolymerizing BMA, DMAEMA, and PAA in the presence of a RAFT CTA (e.g., ECT) and a radical initiator. In an alternative orientation, the block copolymer can comprise a first polymer chain, P″, which can preferably include a random copolymer block comprising monomeric residues derived from polymerization of BMA, DMAEMA and PAA (e.g., as a first block of a block copolymers), a second polymer chain, P‴, which can preferably include poly(DMAEMA), and a chain extension (E*) comprising one or more chain extension residue(s), $E_k$ between the first chain, P″, and the second chain, P‴, where k is an integer ranging from 1 to 20, preferably from 1 to 10, as described herein. For example, poly(DMAEMA) can be prepared by polymerizing DMAEMA the presence of a RAFT CTA (e.g., ECT) and a radical initiator.

In specific instances, provided herein are the polymers (e.g., block copolymers including membrane destabilizing block copolymers) of the following structure:

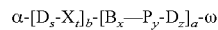   [Structure 1]

   [Structure 2]

wherein x, y, z, s and t are the mole % composition (generally, 0-50%) of the individual monomeric units D (DMAEMA), B (BMA), P (PAA), and a hydrophilic neutral monomer (X) in the copolymer polymeric compound, a and b are the molecular weights of the blocks, In certain embodiments, x is 50%, y is 25% and z is 25%. In certain embodiments, x is 60%, y is 20% and z is 20%. In certain embodiments, x is 70%, y is 15% and z is 15%. In certain embodiments, x is 50%, y is 25% and z is 25%. In certain embodiments, x is 33%, y is 33% and z is 33%. In certain embodiments, x is 50%, y is 20% and z is 30%. In certain embodiments, x is 20%, y is 40% and z is 40%. In certain embodiments, x is 30%, y is 40% and z is 30%. In some embodiments, a block of a copolymer compound can have a molecular weight of about 2,000 KDa to about 30,000 KDa, about 5,000 KDa to about 20,000 KDa, or about 7,000 KDa to about 15,000 KDa. In specific embodiments, a block can be about 7,000 KDa, 8,000 KDa, 9,000 KDa, 10,000 KDa, 11,000 KDa, 12,000 KDa, 13,000 KDa, 14,000 KDa, or 15,000 KDa. In other embodiments, a polymer chain described herein can define a block having a molecular weight of about 10,000 KDa to about 50,000 KDa, about 15,000 KDa to about 35,000 KDa, or about 20,000 KDa to about 30,000 KDa.

As described in certain embodiments, a second block of a block copolymer can comprises a plurality a cationic chargeable species, for example, dimethylaminoethylmethacrylate (DMAEMA). Thus, in some embodiments, the structure of such a polymeric segment is represented by the Structure 3:

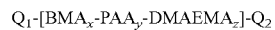   [Structure 3]

wherein $Q_1$ and $Q_2$ in the above designation denote other polymer blocks or end group functionalities, and wherein x, y, and z are the mole % composition (generally, 0-50%) of the individual monomeric units. In certain instances, the individual monomeric units serve individual and synergistic functions. For example, polypropyl acrylic acid, which comprises both anionic species and hydrophobic species, with a pKa value of ~6.7 is hydrophilic above a pH of about 6.7 and is increasingly hydrophobic below a pH of about 6.7, where the carboxylates become protonated. In certain instances, increasing the hydrophobicity of the local environment, for example, by increasing the mole % of the predominantly hydrophobic monomer unit BMA in the block raises the PAA pKa and results in protonation of PAA at a higher pH, that is, the PAA containing block becomes more membrane destabilizing at a higher pH and thus more responsive to smaller acidic changes in pH below physiological pH~7.4. In some instances, protonation of PAA results in a large increase in hydrophobicity and subsequent conformational change to a form with membrane destabilizing properties. A third monomeric unit in the above described polymer block is the cationic species, for example DMAEMA, which, in some instances, serves multiple functions, including but not limited to the following. When matched in equivalent molar amounts to the anionic species of PAA, it creates charge neutralization and the potential for forming electrostatic interactions that can contribute to the stability of the hydrophobic core of a micelle structure where either $Q_1$ or $Q_2$ in the above structure is a hydrophilic homopolymer block, for example poly-DMAEMA.

In general, when the polymer is a multiblock polymer, it is preferred that at least one of the polymer block(s) be a copolymer block and, still more preferred that at least one of polymer block(s) be a random copolymer block. Thus, for example, for certain applications it is generally preferred that the polymer contains a hydrophobic block that is a random copolymer block comprising two or more compositionally distinct monomeric residues. When the polymer additionally comprises a hydrophilic block, the hydrophilic block or the hydrophobic block may be a random copolymer block comprising two or more compositionally distinct monomeric residues; in this embodiment, the hydrophilic block, the hydrophobic block or both of the hydrophobic and hydrophilic blocks may be a random copolymer block comprising two or more compositionally distinct monomeric residues. Additionally, when the polymer comprises at least two compositionally distinct hydrophilic blocks, the hydrophobic block or at least one of the hydrophilic blocks may be a random copolymer block comprising two or more compositionally distinct monomeric residues; in this embodiment, at least one of the hydrophilic blocks, the hydrophobic block or each of the hydrophobic and hydrophilic blocks may be a random copolymer block comprising two or more compositionally distinct monomeric residues. Additionally, when the polymer comprises at least two compositionally distinct hydrophobic blocks, at least one of the hydrophobic blocks may be a random copolymer block comprising two or more compositionally distinct monomeric residues. In each of these embodiments, the polymer comprises at least one chain extension moiety, (E*), at the junction between two of the copolymer blocks.

Advantageously, when the polymer is a multiblock copolymer, each of the blocks may possess somewhat different characteristics or provide a somewhat different function to the polymer. For example, in one embodiment, the polymer is a multiblock polymer comprising a hydrophilic block, a hydrophobic block and, optionally, one or more additional hydrophilic and/or hydrophobic polymeric blocks with a chain extension moiety, (E*), at the junction between two of the blocks. For example, the polymer may have a therapeutic agent attached (covalently or non-covalently) to a block thereof (hydrophilic or hydrophobic) and the polymer may comprise a hydrophobic membrane destabilizing block with a chain extension moiety, E*, between two of the blocks. By way of further example, the polymer may be a multiblock polymer comprising a hydrophilic block (optionally possessing, for example, a targeting moiety) and at least one additional compositionally distinct hydrophilic block. The additional hydrophilic block(s) may be used, for instance, to contribute water solubility to the copolymer, to aid in micelle formation, to enhance the targeting of the copolymer to a cellular or other biological target, to shield a therapeutic agent that is associated with the copolymer, or a combination of two or more thereof. Optionally, the polymer may contain an additional, compositionally distinct hydrophilic block, that complements the other hydrophilic blocks by providing a property or function not provided by the other hydrophilic blocks; for example, the additional hydrophilic block may be used to provide means for attaching a therapeutic agent, contribute water solubility to the copolymer, aid in micelle formation, further target the copolymer to a cellular or other biological target, shield a therapeutic agent that is associated with the copolymer, or a combination of two or more thereof. Alternatively, or additionally, the polymer may comprise, a hydrophobic block to decrease the water solubility of the copolymer, aid in micelle formation, carry a therapeutic agent, destabilize a cellular membrane or other biological target, or a combination of two or more thereof. The copolymer may optionally possess further additional polymeric blocks that amplify the function of the copolymers of the present invention, or which introduce other functionalities or properties to the copolymer. In each of the forgoing embodiments, the polymer preferably contains a chain extension moiety, (E*), at the junction between two of the blocks.

In some embodiments, a composition comprising a polymeric compound of the invention and a polynucleotide (e.g., a 200+mer) associated therewith can be provided in an appropriate buffer and added directly to cells in an in-vitro culture. Expression of the transfected gene or cDNA in the resulting cells can be readily measured by including in the mammalian expression vector an expression cassette driving an indicator gene such as luciferase, chloramphenicol acetyl transferase or GFP. These genes are readily available and reporter assays are described.

In some embodiments, the compositions comprising polymeric compounds and therapeutic agents (e.g., oligonucleotides or siRNA) are delivered to cells by endocytosis. Intracellular vesicles and endosomes are used interchangeably throughout this specification. Successful therapeutic agent (e.g., oligonucleotide or siRNA) delivery into the cytoplasm generally has a mechanism for endosomal escape. In certain instances, the compositions comprising polymeric compounds and comprising therapeutic agents (e.g., oligonucleotide or siRNA) provided herein are sensitive to the lower pH in the endosomal compartment upon endocytosis. In certain instances, endocytosis triggers protonation or charge neutralization of anionically chargeable species (e.g., propyl acrylic acid units) of the polymer chain, resulting in a conformational transition in the polymeric compounds. In certain instances, this conformational transition results in a more hydrophobic membrane destabilizing form which mediates release of the therapeutic agent (e.g., oligonucleotide or siRNA) from the endosomes to the cytoplasm. In those compositions comprising polymeric compounds and comprising siRNA, delivery of siRNA into the cytoplasm allows its mRNA knockdown effect to occur. In those compositions comprising polymeric compounds and comprising other types of oligonucleotides, delivery into the cytoplasm allows their desired action to occur.

In some embodiments, polymeric compounds provided herein are used for gene therapy. The treatment of diseases and disorders by gene therapy generally involves the transfer of new genetic information into cells. "Gene therapy vectors" comprise the new genetic material to be delivered, which is, optionally, in a mammalian expression vector. The uses of polymeric compounds of the invention include delivery of DNA sequences for gene replacement, inhibition of gene expression, gene correction or gene augmentation, or the introduction of genes to have some other desired effect, such as the modulation of immune responses. Inhibition of gene expression is accomplished in any suitable manner, including, by way of non-limiting example, by expression of gene cassettes in cells which express shRNAs or other RNAi agents.

In some embodiments, the non-covalent association (e.g., complex) between the polymeric compound and therapeutic agent (e.g., oligonucleotide or siRNA) forms at a preferred charge ratio as compared between a polymer chain which is polycationic under relevant physiological conditions and the therapeutic agent (e.g., oligonucleotide or siRNA), where preferably such charge ratio ranges from between 1:1 and 16:1. In specific embodiments, the complex forms at the charge ratio of 2:1, 4:1 or 8:1. In other words, in some embodiments, the ratio of the number of cationic charges present in the polymer chain of the polymeric compound to the number of anionic charges present in the therapeutic agent (e.g., oligonucleotide or siRNA) can be a preferred value, e.g., ranging from about 1:1 to about 16:1, about 2:1 to about 8:1, about 4:1 to about 12:1, about 2:1, about 4:1, or about 8:1. In some embodiments, an siRNA is charge-neutralized by a polycationic polymer chain of a polymeric compound. For example, in some specific embodiments, a 20-base pair polynucleotide (e.g., oligonucleotide or siRNA) comprising 40 negative charges at physiologic pH is associated (e.g., complexed) with polymer chain of a polymeric compound which is a block copolymer comprising a polyDMAEMA block (80 monomeric units in length, MW=11, 680) with a pKa of about 7.4. At this pH, polyDMAEMA contains 40 negative charges, thereby resulting in a polynucleotide-polymer chain association (e.g., complex) that is substantially net neutral in charge. In certain instances, avoiding a large number of excess positive charges helps to reduce in vitro and in vivo toxicity. In some embodiments, a therapeutic agent (e.g., oligonucleotide or siRNA) spontaneously associates with a positively charged cationic polymer chain of a polymeric compound, as provided herein.

In some embodiments, the polymeric compounds provided herein are useful in treating a subject at risk for or afflicted with disorders associated with and/or caused by high plasma levels or cholesterol, apolipoprotein b, and/or LDL cholesterol, e.g. hypercholesterolemia. The treatment comprises providing a composition comprising a polymeric compound and a therapeutic agent (e.g., an oligonucleotide agent), wherein the therapeutic agent silences (e.g., by cleavage) a gene or a gene product which promotes such condition. In some embodiments the therapeutic agent silences proprotein convertase subtilisin/kexin type 9 (PCSK9) gene responsible for regulation of low density lipoprotein (LDLR) levels and function, and thus polymeric compounds comprising such therapeutic agents are used to treat a subject having or at risk for a disorder characterized by unwanted PCSK9 expression, e.g., disorders associated with and/or caused by high plasma levels or cholesterol, apolipoprotein b, and/or LDL cholesterol, e.g. hypercholesterolemia. In some embodiments, the polymeric compounds deliver PCSK9-silencing RNAi agent (e.g., siRNA) to a cell expressing PCSK9. In some embodiments, the cell is a liver cell.

In some embodiments, the polymeric compounds provided herein are useful in treating a subject at risk for or afflicted with unwanted cell proliferation (e.g., malignant or nonmalignant cell proliferation). The treatment comprises providing a composition comprising polymeric compounds and a therapeutic agent (e.g., an oligonucleotide agent), wherein the therapeutic agent can silence (e.g., by cleavage) a gene or a gene product which promotes unwanted cell proliferation; and administering a therapeutically effective dose of the polymeric compounds to a subject (e.g., a human subject.) In some embodiments, the therapeutic agent is a polynucleotide (e.g., an oligonucleotide) which is homologous to and can silence (e.g., by cleavage) a gene.

In certain embodiments, the gene is but is not limited to a growth factor or growth factor receptor gene, a phosphatase, a kinase, e.g., a protein tyrosine, serine or threonine kinase gene, an adaptor protein gene, a gene encoding a G protein superfamily molecule, or a gene encoding a transcription factor. In some instances, a composition comprising polymeric compounds and a therapeutic agent comprises a polynucleotide which silences a gene which is expressed in a specific tissue or organ, including, but not limited to lung, pancreas, liver, kidney, ovary, muscle, skin, breast, colon, stomach, and the like.

In some embodiments, the oligonucleotide agent silences one or more of the following genes: the PDGF beta gene, and thus can be used to treat a subject having or at risk for a disorder characterized by unwanted PDGF beta expression, e.g., testicular and lung cancers; an Erb-B gene (e.g., Erb-B-2 or Erb-B-3), and thus can be used to treat a subject having or at risk for a disorder characterized by unwanted Erb-B expression, e.g., breast or lung cancer; the Src gene, and thus can be used to treat a subject having or at risk for a disorder characterized by unwanted Src expression, e.g., colon cancers; the CRK gene, and thus can be used to treat a subject having or at risk for a disorder characterized by unwanted CRK expression, e.g., colon and lung cancers; the GRB2 gene, and thus can be used to treat a subject having or at risk for a disorder characterized by unwanted GRB2 expression, e.g., squamous cell carcinoma; the RAS gene, and thus can be used to treat a subject having or at risk for a disorder characterized by unwanted RAS expression, e.g., pancreatic, colon and lung cancers, and chronic leukemia; the MEKK gene, and thus can be used to treat a subject having or at risk for a disorder characterized by unwanted MEKK expression, e.g., squamous cell carcinoma, melanoma or leukemia; the JNK gene, and thus can be used to treat a subject having or at risk for a disorder characterized by unwanted JNK expression, e.g., pancreatic or breast cancers; the RAF gene, and thus can be used to treat a subject having or at risk for a disorder characterized by unwanted RAF expression, e.g., lung cancer or leukemia; the Erk1/2 gene, and thus can be used to treat a subject having or at risk for a disorder characterized by unwanted Erk1/2 expression, e.g., lung cancer; the PCNA (p21) gene, and thus can be used to treat a subject having or at risk for a disorder characterized by unwanted PCNA expression, e.g., lung cancer; the MYB gene, and thus can be used to treat a subject having or at risk for a disorder characterized by unwanted MYB expression, e.g., colon cancer or chronic myelogenous leukemia; the c-MYC gene, and thus can be used to treat a subject having or at risk for a disorder characterized by unwanted c-MYC expression, e.g., Burkitt's lymphoma or neuroblastoma; the JUN gene, and thus can be used to treat a subject having or at risk for a disorder characterized by unwanted JUN expression, e.g., ovarian, prostate or breast cancers; the FOS gene, and thus can be used to treat a subject having or at risk for a disorder characterized by unwanted FOS expression, e.g., skin or prostate cancers; the BCL-2 gene, and thus can be used to treat a subject having or at risk for a disorder characterized by unwanted BCL-2 expression, e.g., lung or prostate cancers or Non-Hodgkin lymphoma; the Cyclin D gene, and thus can be used to treat a subject having or at risk for a disorder characterized by unwanted Cyclin D expression, e.g., esophageal and colon cancers; the VEGF gene, and thus can be used to treat a subject having or at risk for a disorder characterized by unwanted VEGF expression, e.g., esophageal and colon cancers; the EGFR gene, and thus can be used to treat a subject having or at risk for a disorder characterized by unwanted EGFR expression, e.g., breast cancer; the Cyclin A gene, and thus can be used to treat a subject having or at risk for a disorder characterized by unwanted Cyclin A expression, e.g., lung and cervical cancers; the Cyclin E gene, and thus can be used to treat a subject having or at risk for a disorder characterized by unwanted Cyclin E expression, e.g., lung and breast cancers; the WNT-1 gene, and thus can be used to treat a subject having or at risk for a disorder characterized by unwanted WNT-1 expression, e.g., basal cell carcinoma; the beta-catenin gene, and thus can be used to treat a subject having or at risk for a disorder characterized by unwanted beta-catenin expression, e.g., adenocarcinoma or hepatocellular carcinoma; the c-MET gene, and thus can be used to treat a subject having or at risk for a disorder characterized by unwanted c-MET expression, e.g., hepatocellular carcinoma; the PKC gene, and thus can be used to treat a subject having or at risk for a disorder characterized by unwanted PKC expression, e.g., breast cancer; the NFKB gene, and thus can be used to treat a subject having or at risk for a disorder characterized by unwanted NFKB expression, e.g., breast cancer; the STAT3 gene, and thus can be used to treat a subject having or at risk for a disorder characterized by unwanted STAT3 expression, e.g., prostate cancer; the survivin gene, and thus can be used to treat a subject having or at risk for a disorder characterized by unwanted survivin expression, e.g., cervical or pancreatic cancers; the Her2/Neu gene, and thus can be used to treat a subject having or at risk for a disorder characterized by unwanted Her2/Neu expression, e.g., breast cancer; the topoisomerase I gene, and thus can be used to treat a subject having or at risk for a disorder characterized by unwanted topoisomerase I expression, e.g., ovarian and colon cancers; the topoisomerase II alpha gene, and thus can be used to treat a subject having or at risk for a disorder characterized by unwanted topoisomerase II expression, e.g., breast and colon cancers.

In other embodiments the oligonucleotide agent silences mutations in one of the following genes: the p73 gene, and thus can be used to treat a subject having or at risk for a disorder characterized by unwanted p73 expression, e.g., colorectal adenocarcinoma; the p21 (WAF1/CIP1) gene, and thus can be used to treat a subject having or at risk for a disorder characterized by unwanted p21 (WAF1/CIP1) expression, e.g., liver cancer; the p27 (KIP1) gene, and thus can be used to treat a subject having or at risk for a disorder characterized by unwanted p27 (KIP1) expression, e.g., liver cancer; the PPM1D gene, and thus can be used to treat a subject having or at risk for a disorder characterized by unwanted PPM1D expression, e.g., breast cancer; the RAS gene, and thus can be used to treat a subject having or at risk for a disorder characterized by unwanted RAS expression, e.g., breast cancer; the caveolin I gene, and thus can be used to treat a subject having or at risk for a disorder characterized by unwanted caveolin I expression, e.g., esophageal squamous cell carcinoma; the MIB I gene, and thus can be used to treat a subject having or at risk for a disorder characterized by unwanted MIB I expression, e.g., male breast carcinoma (MBC); MTAI gene, and thus can be used to treat a subject having or at risk for a disorder characterized by unwanted MTAI expression, e.g., ovarian carcinoma; the M68 gene, and thus can be used to treat a subject having or at risk for a disorder characterized by unwanted M68 expression, e.g., human adenocarcinomas of the esophagus, stomach, colon, and rectum.

In some embodiments the oligonucleotide agent silences mutations in tumor suppressor genes, and thus can be used as a method to promote apoptotic activity in combination with chemotherapeutics. In some embodiments the in the tumor suppressor gene is selected from one or more of the following tumor suppressor genes: the p53 tumor suppressor gene, the p53 family member DN-p63, the pRb tumor suppressor gene, the APC1 tumor suppressor gene, the BRCA1 tumor suppressor gene, the PTEN tumor suppressor gene.

In some embodiments the oligonucleotide agent silences one of the following fusion genes: mLL fusion genes, e.g., mLL-AF9, and thus can be used to treat a subject having or at risk for a disorder characterized by unwanted mLL fusion gene expression, e.g., acute leukemias; the BCR/ABL fusion gene, and thus can be used to treat a subject having or at risk for a disorder characterized by unwanted BCR/ABL fusion gene expression, e.g., acute and chronic leukemias; the TEL/AML1 fusion gene, and thus can be used to treat a subject having or at risk for a disorder characterized by unwanted TEL/AML1 fusion gene expression, e.g., childhood acute leukemia; the EWS/FLI1 fusion gene, and thus can be used to treat a subject having or at risk for a disorder characterized by unwanted EWS/FLI1 fusion gene expression, e.g., Ewing Sarcoma; the TLS/FUS1 fusion gene, and thus can be used to treat a subject having or at risk for a disorder characterized by unwanted TLS/FUS1 fusion gene expression, e.g., Myxoid liposarcoma; the PAX3/FKHR fusion gene, and thus can be used to treat a subject having or at risk for a disorder characterized by unwanted PAX3/FKHR fusion gene expression, e.g., Myxoid liposarcoma; the AML1/ETO fusion gene, and thus can be used to treat a subject having or at risk for a disorder characterized by unwanted AML1/ETO fusion gene expression, e.g., acute leukemia.

In some aspects herein the composition comprising polymeric compounds and a therapeutic agent provide therapeutic agents for treating a subject, e.g., a human, at risk for or afflicted with a disease or disorder that may benefit by angiogenesis inhibition e.g., cancer or retinal degeneration. The treatment comprises providing a composition comprising polymeric compounds and a therapeutic agent comprising an oligonucleotide agent, wherein said oligonucleotide agent is homologous to and/or can silence, e.g., by cleavage, a gene which mediates angiogenesis (e.g., VEGF-R1, VEGF-R2 or a gene encoding signaling proteins for these receptors' pathways); and administering a therapeutically effective dosage of said polymeric compounds comprising the oligonucleotide agent to a subject, e.g., a human subject.

In some embodiments the oligonucleotide agent silences one of the following genes: the alpha v-integrin gene, and thus can be used to treat a subject having or at risk for a disorder characterized by unwanted alpha V integrin, e.g., brain tumors or tumors of epithelial origin; the Flt-1 receptor gene, and thus can be used to treat a subject having or at risk for a disorder characterized by unwanted Flt-1 receptors, e.g., cancer and rheumatoid arthritis; the tubulin gene, and thus can be used to treat a subject having or at risk for a disorder characterized by unwanted tubulin, e.g., cancer and retinal neovascularization.

In some aspects the composition comprising polymeric compounds and a therapeutic agent comprising oligonucleotide agents provided herein relate to a method of treating a subject infected with a virus or at risk for or afflicted with a disorder or disease associated with a viral infection. The method comprises providing a polymeric compounds comprising an oligonucleotide agent, wherein said oligonucleotide agent is homologous to and/or can silence, e.g., by cleavage, a viral gene or a cellular gene which mediates viral function, e.g., entry or growth; and administering a therapeutically effective dose of said oligonucleotide agent to a subject, e.g., a human subject.

In some embodiments, composition comprising polymeric compounds and a therapeutic agent comprising an oligonucleotide agent are useful in treatment of subjects infected with the Human Papilloma Virus (HPV) or at risk for or afflicted with a disorder mediated by HPV, e.g., cervical cancer.

In some embodiments, the composition comprising polymeric compounds and a therapeutic agent comprises an oligonucleotide agent silencing expression of a HPV gene is reduced. In some embodiments, the HPV gene is selected from the group of E2, E6, or E7.

In another embodiment the expression of a human gene that is required for HPV replication is reduced.

In some embodiments, the composition comprising polymeric compounds and a therapeutic agent comprises an oligonucleotide agent useful in treating patients infected by the Human Immunodeficiency Virus (HIV) or at risk for or afflicted with a disorder mediated by HIV, e.g., Acquired Immune Deficiency Syndrome (AIDS). In some embodiments, the expression of an HIV gene is reduced. In other embodiments, the HIV gene is CCR5, Gag, or Rev. In some embodiments the expression of a human gene that is required for HIV replication is reduced. In some embodiments, the gene is CD4 or Tsg101.

In some embodiments, the composition comprising polymeric compounds and a therapeutic agent comprises an oligonucleotide agent useful for treating patients infected by the Hepatitis B Virus (HBV) or at risk for or afflicted with a disorder mediated by HBV, e.g., cirrhosis and hepatocellular carcinoma. In one embodiment, the expression of a HBV gene is reduced. In other embodiment, the targeted HBV gene encodes one of the groups of the tail region of the HBV core protein, the pre-cregious (pre-c) region, or the cregious (c) region. In other embodiments a targeted HBV-RNA sequence is comprised of the poly(A) tail. In some embodiments the expression of a human gene that is required for HBV replication is reduced.

In some embodiments, the composition comprising polymeric compounds and a therapeutic agent comprises an oligonucleotide agent useful for treating patients infected with, or at risk for or afflicted with a disorder mediated by a virus selected from the following viruses: the Hepatitis A Virus (HAV); Hepatitis C Virus (HCV); any of the group of Hepatitis Viral strains comprising hepatitis D, E, F, G, or H; the Respiratory Syncytial Virus (RSV); the herpes Cytomegalovirus (CMV); the herpes Epstein Barr Virus (EBV); Kaposi's Sarcoma-associated Herpes Virus (KSHV); the JC Virus (JCV); myxovirus (e.g., virus causing influenza), rhinovirus (e.g., virus causing the common cold), or coronavirus (e.g., virus causing the common cold); the St. Louis Encephalitis flavivirus; the Tick-borne encephalitis flavivirus; the Murray Valley encephalitis flavivirus; the dengue flavivirus; the Simian Virus 40 (SV40); the encephalomyocarditis virus (EMCV); the measles virus (MV); the Varicella zoster virus (VZV); an adenovirus (e.g. virus causing a respiratory tract infection); the poliovirus; or a poxvirus (a poxvirus causing smallpox). In some embodiments the expression of a human gene that is required for the replication of these viruses is reduced.

In some embodiments, the composition comprising polymeric compounds and a therapeutic agent comprises an oligonucleotide agent useful for treating patients infected by the Herpes Simplex Virus (HSV) or at risk for or afflicted with a disorder mediated by HSV, e.g., genital herpes and cold sores as well as life-threatening or sight-impairing disease, e.g., mainly in immunocompromised patients. In some embodiments, the expression of a HSV gene is reduced. In other embodiment, the targeted HSV gene encodes DNA polymerase or the helicase-primase. In some embodiments the expression of a human gene that is required for HSV replication is reduced.

In some embodiments, the composition comprising polymeric compounds and a therapeutic agent comprises an oligonucleotide agent useful for treating patients infected by the West Nile Virus or at risk for or afflicted with a disorder mediated by West Nile Virus. In some embodiments, the expression of a West Nile Virus gene is reduced. In other preferred embodiments, the West Nile Virus gene is selected from the group comprising E, NS3, or NS5. In some embodiments the expression of a human gene that is required for West Nile Virus replication is reduced.

In some embodiments, the composition comprising polymeric compounds and a therapeutic agent comprises an oligonucleotide agent useful for treating patients infected by the Human T Cell Lymphotropic Virus (HTLV), or a disease or disorder associated with this virus, e.g., leukemia or myelopathy. In some embodiments, the expression of a HTLV gene is reduced. In some embodiments, the HTLV1 gene is the Tax transcriptional activator. In some embodiments, the expression of a human gene that is required for HTLV replication is reduced.

In some aspects, the composition comprising polymeric compounds and a therapeutic agent comprises an oligonucleotide agent useful for treating a subject infected with a pathogen, e.g., a bacterial, amoebic, parasitic, or fungal pathogen. The method of treatment comprises providing a composition comprising a polymeric compound and comprising an oligonucleotide agent, wherein said oligonucleotide is homologous to and/or can silence, e.g., by cleavage of a pathogen gene or a gene involved in the pathogen's growth; and administering a therapeutically effective dose of said oligonucleotide agent to a subject, e.g., a human subject. The target gene can be selected from a gene involved in the pathogen's growth, cell wall synthesis, protein synthesis, transcription, energy metabolism, e.g., the Krebs cycle, or toxin production.

Thus, in some embodiments, the composition comprising polymeric compounds and a therapeutic agent comprises an oligonucleotide agent useful for of treating patients infected by a *plasmodium* that causes malaria. In some embodiments, the expression of a *plasmodium* gene is reduced. In other embodiments, the gene is apical membrane antigen 1 (AMA1). In some embodiments, the expression of a human gene that is required for *plasmodium* replication is reduced.

In some embodiments, the composition comprising polymeric compounds and a therapeutic agent comprises an oligonucleotide agent useful for treating patients infected by *Mycobacterium ulcerans, Mycobacterium tuberculosis, Mycobacterium leprae, Staphylococcus aureus, Streptococcus pneumoniae, Streptococcus pyogenes, Chlamydia pneumoniae, Mycoplasma pneumoniae*, or a disease or disorder associated with any of these pathogens. In some embodiments, the expression of a bacterial gene and/or a human gene that is required for the replication of these bacteria is reduced.

In some embodiments, the diseases treated by the compositions comprising polymeric compounds provided herein may be systemic or present in a specific tissue, e.g., the lung, skin, liver, breast, kidney, pancreas, CNS, or the like. In certain aspects, the oligonucleotide silences a gene which mediates or is involved in a metabolic disease or disorder, e.g., diabetes, obesity, and the like. In certain embodiments, the oligonucleotide silences a gene which mediates or is involved in a pulmonary disease or disorder, e.g., chronic obstructive pulmonary disease (COPD), cystic fibrosis, or lung cancer. In some aspects herein, the compositions comprise polymeric compounds and comprise an oligonucleotide agent useful for and/or related to a method of treating a subject, e.g., a human, at risk for or afflicted with a disease or disorder characterized by an unwanted immune response, e.g., an inflammatory disease or disorder or an autoimmune disease or disorder. The method comprises providing composition comprising a polymeric compound and comprising an oligonucleotide agent, wherein said oligonucleotide agent is homologous to and/or can silence, e.g., by cleavage, a gene which mediates an unwanted immune response; and administering said oligonucleotide agent to a subject, e.g., a human subject. In some embodiments, the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis. In other embodiments, the disease or disorder is restenosis, e.g., restenosis associated with surgical intervention e.g., angioplasty, e.g., percutaneous transluminal coronary angioplasty. In other embodiments, the disease or disorder is Inflammatory Bowel Disease, e.g., Crohn Disease or Ulcerative Colitis. In some embodiments, the disease or disorder is inflammation associated with an infection or injury. In other embodiments, the disease or disorder is asthma, allergy, lupus, multiple sclerosis, diabetes, e.g., type II diabetes, arthritis, e.g., rheumatoid or psoriatic. In certain embodiments the oligonucleotide agent silences an integrin or co-ligand thereof, e.g., VLA4, VCAM, ICAM. In other embodiments the oligonucleotide agent silences a selectin or co-ligand thereof, e.g., P-selectin, E-selectin (ELAM), I-selectin, P-selectin glycoprotein-1 (PSGL-1). In certain embodiments the oligonucleotide agent silences a component of the complement system, e.g., C3, C5, C3aR, C5aR, C3 convertase, and C5 convertase. In some embodiments the oligonucleotide agent silences a chemokine or receptor thereof, e.g., TNFI, TNFJ, IL-1I, IL-1J, IL-2, IL-2R, IL-4, IL-4R, IL-5, IL-6, IL-8, TNFRI, TNFRII, IgE, SCYA11, and CCR3. In other embodiments the oligonucleotide agent silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, or I-309.

In some aspects, the composition comprising polymeric compounds and a therapeutic agent comprise an oligonucleotide agent useful for treating a subject, e.g., a human, at risk for or afflicted with a neurological disease or disorder. The method comprises providing a compositions comprising polymeric compounds and an oligonucleotide agent, wherein said oligonucleotide is homologous to and/or can silence, e.g., by cleavage, a gene which mediates a neurological disease or disorder; and administering a therapeutically effective dose of said oligonucleotide agent to a subject, e.g., a human. In some embodiments the disease or disorder is Alzheimer Disease or Parkinson Disease. In certain embodiments the oligonucleotide agent silences an amyloid-family gene, e.g., APP; a presenilin gene, e.g., PSEN1 and PSEN2, or I-synuclein. In other embodiments the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8. In some embodiments the oligonucleotide agent silences HD, DRPLA, SCA1, SCA2, MJD1, CACNL1A4, SCA7, or SCA8.

In certain aspects, the composition comprising polymeric compounds and a therapeutic agent provided herein comprise an oligonucleotide agent capable of cleaving or silencing more than one gene. In these embodiments the oligonucleotide agent is selected so that it has sufficient homology to a sequence found in more than one gene, e.g. a sequence conserved between these genes. Thus in some embodiments an oligonucleotide agent targeted to such sequences effectively silences the entire collection of genes.

In some aspects, the composition comprising polymeric compounds and a therapeutic agent provided herein comprise two or more types of oligonucleotide agents wherein the oligonucleotide agents silence different genes of the same disease or different diseases.

Pharmaceutical Compositions

Compositions comprising polymeric compounds provided herein (e.g., those associated with one or more therapeutic agent, such as one or more oligonucleotide) are optionally provided in a pharmaceutical composition (e.g., pharmaceutically acceptable composition) comprising the polymeric compound and a pharmaceutically acceptable excipient. In some embodiments, the compositions comprising polymeric compounds provided herein can be administered to a patient in any suitable manner, e.g., with or without stabilizers, buffers, and the like, to form a pharmaceutical composition. In some embodiments, the compositions comprising polymeric compounds provided herein are formulated and used as tablets, capsules or elixirs for oral administration, suppositories for rectal administration, sterile solutions, suspensions for injectable administration, and any other suitable compositions.

Provided are pharmaceutically acceptable formulations of the compositions comprising polymeric compounds comprising at least one therapeutic agent described herein. These formulations include salts of the above compounds, e.g., acid addition salts, e.g., salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, e.g., oral, transdermal, or by injection. Thus, in specific embodiments wherein the compositions comprising polymeric compounds comprises and is delivering a polynucleotide, the formulation is in a form that does not prevent the compositions comprising polymeric compounds and, more specifically, the polynucleotide (e.g., oligonucleotide or siRNA) from reaching a target cell with the polynucleotide intact and/or functional. For example, in certain embodiments, pharmacological compositions injected into the blood stream are soluble and/or dispersible. Moreover, pharmaceutical compositions described herein are, preferably, non-toxic. In some embodiments, wherein a compositions comprising polymeric compounds described herein is administered for therapeutic benefit, a therapeutic effective amount of the compositions comprising polymeric compounds comprising a therapeutic agent (e.g., a polynucleotide, such as an siRNA) is administered. In an exemplary embodiment, a therapeutically effective amount includes an amount of compositions comprising polymeric compounds sufficient to provide about 10 mg or less of siRNA per kg of individual.

In some embodiments, pharmaceutical compositions comprising a compositions comprising polymeric compounds, which comprise a therapeutic agent (e.g., a polynucleotide, such as an siRNA), are administered systemically. As used herein, "systemic administration" means in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular. In some embodiments, the compositions comprising polymeric compounds are administered topically.

In some embodiments, the compositions are prepared for storage or administration and include a pharmaceutically effective amount of the therapeutic agent comprising compositions comprising polymeric compounds in a pharmaceutically acceptable carrier or diluent. Any acceptable carriers or diluents are optionally utilized herein. Specific carriers and diluents and are described, e.g., in *Remington's Pharmaceutical Sciences*, Mack Publishing Co., A. R. Gennaro Ed., 1985. For example, preservatives, stabilizers, dyes and flavoring agents are optionally added. These include sodium benzoate, sorbic acid and esters of p-hydroxybenzoic acid. In addition, antioxidants and suspending agents are optionally used. As used herein, the term "pharmaceutically acceptable carrier" means a non-toxic, inert solid, semi-solid or liquid filler, diluent, encapsulating material or formulation auxiliary of any type. Some examples of materials optionally used as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In some embodiments, the pharmaceutical compositions provided herein are administered to humans and/or to animals, orally, rectally, parenterally, intracistemally, intravaginally, intranasally, intraperitoneally, topically (as by powders, creams, ointments, or drops), bucally, or as an oral or nasal spray.

In various embodiments, liquid dosage forms for oral administration include pharmaceutically acceptable emulsions, microemulsions, solutions, suspensions, syrups, and elixirs. In addition to the active ingredients (i.e., polymeric compounds-oligonucleotide complexes provided herein), the liquid dosage forms optionally further contain inert diluents or excipients, such as by way of non-limiting example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions optionally also include adjuvants such as wetting agents, emulsifying and suspending agents, sweetening, flavoring, and perfuming agents.

In some embodiments, injectable preparations, for example, sterile injectable aqueous or oleaginous suspensions are formulated according in any suitable manner, e.g., using dispersing agents, wetting agents and/or suspending agents. The sterile injectable preparation is, optionally, a sterile injectable solution, suspension, or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil is optionally employed including synthetic mono- or diglycerides. In additional embodiments, fatty acids such as oleic acid are used in the preparation of injectables. In a specific embodiment, the compositions comprising polymeric compounds are suspended in a carrier fluid comprising 1% (w/v) sodium carboxymethyl cellulose and 0.1% (v/v) Tween 80.

In some embodiments, the injectable formulations are sterilized, for example, by filtration through a bacteria-retaining filter, or by incorporating sterilizing agents in the form of sterile solid compositions which are optionally dissolved or dispersed in sterile water or other sterile injectable medium prior to use.

In certain embodiments, compositions for rectal or vaginal administration are suppositories. Suppositories are optionally prepared by mixing the composition comprising the polymeric compound and the therapeutic agent as provided herein with suitable non-irritating excipients or carriers such as cocoa butter, polyethylene glycol, or a suppository wax which are solid at ambient temperature but liquid at body temperature and therefore melt in the rectum or vaginal cavity and release the compositions comprising polymeric compounds.

Suitable solid dosage forms for oral administration include, by way of non-limiting example, capsules, tablets, pills, powders, and granules. In such solid dosage forms, the compositions comprising polymeric compounds and comprising a therapeutic agent (e.g., oligonucleotide) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type are also optionally employed as fillers in soft and hard-filled gelatin capsules using such excipients as lactose or milk sugar as well as high molecular weight polyethylene glycols and the like.

In some embodiments, the solid dosage forms of tablets, dragees, capsules, pills, and granules are prepared with coatings and shells such as enteric coatings and other suitable coatings. They optionally contain opacifying agents. In certain embodiments, they are of a composition that they release the active ingredient(s) only, or preferentially, in a certain part of the intestinal tract, optionally, in a delayed manner. Examples of suitable embedding compositions include, by way of non-limiting example, polymeric substances and waxes.

Solid compositions of a similar type are optionally employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include, by way of non-limiting example, ointments, pastes, creams, lotions, gels, powders, solutions, sprays, inhalants, or patches. In some embodiments, the compositions comprising polymeric compounds and therapeutic agent provided herein are admixed under sterile conditions with a pharmaceutically acceptable carrier and, optionally, one or more preservative, one or more buffer, or a combination thereof (e.g., as may be required). Ophthalmic formulation, ear drops, and eye drops are also contemplated as being within the scope of this invention.

Ointments, pastes, creams, and gels provided herein optionally contain, in addition to the compositions comprising polymeric compounds and therapeutic agent provided herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays optionally contain, in addition to the compositions comprising polymeric compounds and therapeutic agent provided herein, excipients such as lactose, talc, silicic acid, aluminum hydroxide, calcium silicates, and polyamide powder, or mixtures of these substances. In some embodiments, sprays additionally contain customary propellants such as chlorofluorohydrocarbons.

Transdermal patches have the added advantage of providing controlled delivery of a compound to the body. Such dosage forms are made in any suitable manner, e.g., by dissolving or dispensing the microparticles or nanoparticles in a proper medium. Absorption enhancers are optionally used to increase the flux of the compound across the skin. The rate can be controlled by either providing a rate controlling membrane or by dispersing compositions comprising polymeric compounds and therapeutic agent provided herein in a polymer matrix or gel.

In some aspects of the invention, the compositions comprising polymeric compounds (s) provide some properties (e.g. mechanical, thermal, etc.) that are usually performed by excipients, thus decreasing the amount of such excipients required for the formulation.

As used herein, the following phrases can have the ascribed meanings, unless otherwise apparent from the context. As used in this specification and the appended claims, the singular forms "a," "an" and "the" include plural referents unless the context clearly dictates otherwise. In describing and claiming the present invention, the following terminology will be used in accordance with the definitions set out below. The word "about" generally means approximately the value as stated, and includes, both generally and specifically the exact value as stated.

As used herein, the phrase "having a formula" or "having a structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms. The term "aryloxy" is used in a similar fashion, with aryl as defined below.

Similarly, the term "alkyl thio" as used herein intends an alkyl group bound through a single, terminal thioether linkage; that is, an "alkyl thio" group may be represented as —S-alkyl where alkyl is as defined above. A "lower alkyl thio" group intends an alkyl thio group containing one to six, more preferably one to four, carbon atoms.

The term "allenyl" is used herein in the conventional sense to refer to a molecular segment having the structure —CH═C═CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. In particular embodiments, aryl substituents have 1 to about 200 carbon atoms, typically 1 to about 50 carbon atoms, and preferably 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are groups such as hydroxyl, alkoxy, thio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

As used herein the term "silyl" refers to the $-SiZ^1Z^2Z^3$ radical, where each of $Z^1$, $Z^2$, and $Z^3$ is independently selected from the group consisting of hydrido and optionally substituted alkyl, alkenyl, alkynyl, aryl, aralkyl, alkaryl, heterocyclic, alkoxy, aryloxy and amino.

As used herein, the term "phosphino" refers to the group $-PZ^1Z^2$, where each of $Z^1$ and $Z^2$ is independently selected from the group consisting of hydrido and optionally substituted alkyl, alkenyl, alkynyl, aryl, aralkyl, alkaryl, heterocyclic and amino.

The term "amino" is used herein to refer to the group $-NZ^1Z^2$, where each of $Z^1$ and $Z^2$ is independently selected from the group consisting of hydrido and optionally substituted alkyl, alkenyl, alkynyl, aryl, aralkyl, alkaryl and heterocyclic.

The term "thio" is used herein to refer to the group $-SZ^1$, where $Z^1$ is selected from the group consisting of hydrido and optionally substituted alkyl, alkenyl, alkynyl, aryl, aralkyl, alkaryl and heterocyclic.

As used herein all reference to the elements and groups of the Periodic Table of the Elements is to the version of the table published by the Handbook of Chemistry and Physics, CRC Press, 1995, which sets forth the new IUPAC system for numbering groups.

Aliphatic or aliphatic group: the term "aliphatic" or "aliphatic group", as used herein, means a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms.

Aryl or aryl group: as used herein, the term "aryl" or "aryl group" refers to monocyclic, bicyclic, and tricyclic ring systems having a total of five to fourteen ring atoms, wherein at least one ring in the system is aromatic and wherein each ring in the system contains three to seven ring atoms.

Charge Neutralized: As used herein, a "charge neutralized" means a particle having a Zeta potential that is between ±10 to ±30 mV, and/or the presence of a first number (z) of chargeable species that are chargeable to a negative charge (e.g., acidic species that become anionic upon de-protonation) and a second number (0.5·z) of chargeable species that are chargeable to a positive charge (e.g., basic species that become cationic upon protonation).

Heteroalkyl: the term "heteroalkyl" means an alkyl group wherein at least one of the backbone carbon atoms is replaced with a heteroatom.

Heteroaryl: the term "heteroaryl" means an aryl group wherein at least one of the ring members is a heteroatom.

Hetero-hydrocarbyl: the term "hetero-hydrocarbyl" means a hydrocarbyl moiety wherein at least one of the backbone carbon atoms is replaced with a heteroatom.

As used herein, a "chargeable species", "chargeable group", or "chargeable monomeric unit" is a species, group or monomeric unit in either a charged or non-charged state. In certain instances, a "chargeable monomeric unit" is one that is converted to a charged state (either an anionic or cationic charged state) such as by the addition or removal of an electrophile (e.g., a proton (H*), for example, in a pH dependent manner). The use of any of the terms "chargeable species", "chargeable group", or "chargeable monomeric unit" includes the disclosure of any other of a "chargeable species", "chargeable group", or "chargeable monomeric unit" unless otherwise stated. A "chargeable species" that is "chargeable to an anion" or "chargeable to an anionic species" is a species or group that is either in an anionic charged state or non-charged state, but in the non-charged state is capable of being converted to an anionic charged state, e.g., by the removal of an electrophile, such as a proton (H+). A "chargeable species" that is "chargeable to a cation" or "chargeable to a cationic species" is a species or group that is either in an cationic charged state or non-charged state, but in the non-charged state is capable of being converted to a cationic charged state, e.g., by the addition of an electrophile, such as a proton (H+). "Chargeable monomeric units" described herein are used interchangeably with "chargeable monomeric residues".

Heteroatom: the term "heteroatom" means an atom other than hydrogen or carbon, such as oxygen, sulfur, nitrogen, phosphorus, boron, arsenic, selenium or silicon atom.

Hydrophobic species: "hydrophobic species", as used herein, is a moiety such as a substituent, residue or a group which, when covalently attached to a molecule, such as a monomer or a polymer increases the molecule's hydrophobicity or serves as a hydrophobicity enhancing moiety. The term "hydrophobicity" is a term of art describing a physical property of a compound measured by the free energy of transfer of the compound between a non-polar solvent and water (Hydrophobicity regained. Karplus P. A., *Protein Sci.*, 1997, 6: 1302-1307.) A compound's hydrophobicity can be measured by its log P value, the logarithm of a partition coefficient (P), which is defined as the ratio of concentrations of a compound in the two phases of a mixture of two immiscible solvents, e.g. octanol and water. Experimental methods of determination of hydrophobicity as well as methods of computer-assisted calculation of log P values are known to those skilled in the art. Hydrophobic species of the present invention include but are not limited to aliphatic, heteroaliphatic, aryl, and heteroaryl groups.

Inhibition: The terms "inhibition," "silencing," and "attenuation" as used herein refer to a measurable reduction in expression of a target mRNA or the corresponding protein as compared with the expression of the target mRNA or the corresponding protein in the absence of a knockdown agent. "Knockdown", or the reduction in expression of the target mRNA or the corresponding protein, can be assessed by measuring the mRNA levels using techniques well known in the art such as quantitative polymerase chain reaction (qPCR) amplification, RNA solution hybridization, nuclease protection, northern blotting and hybridization, and gene expression monitoring with a microarray; and in the case of proteins by techniques well known in the art such as SDS-PAGE, antibody binding, western blot analysis, immunoprecipitation, radioimmunoassay or enzyme-linked immunosorbent assay (ELISA), fluorescence activated cell analysis and immunocytochemistry.

Membrane Destabilizing: As used herein, "membrane-destabilizing" refers to the ability of a polymer to either directly elicit a rift in a cellular membrane structure or to weaken the membrane such that other factors can complete the disruption so as to permit substances to enter a cell or a cellular organelle or to exit the cell or organelle. Means of assessing the membrane-destabilizing properties of the polymers of this invention are well-known to those skilled in the art and include, without limitation, such an in vitro technique as pH dependent red blood cell lysis.

Micellic Assembly: As used herein, a "micellic assembly" includes a particle comprising a core and a hydrophilic shell, wherein the core is held together at least partially, predominantly or substantially through hydrophobic interactions.

Micelle: As used herein, a "micelle" includes a particle comprising a hydrophobic core and a hydrophilic shell. In certain instances, as used herein, a "micelle" is a multi-component, nanoparticle comprising at least two domains, the inner domain or core, and the outer domain or shell. The core is at least partially, predominantly or substantially held together by hydrophobic interactions, and is present in the center of the micelle. As used herein, the "shell of a micelle" is defined as non-core portion of the micelle.

Nucleotide/Polynucleotide: As used herein, the term "nucleotide" refers to a nucleic acid or a nucleic acid residues (e.g. nucleotides and/or nucleosides) of a polynucleotide. A polynucleotide is a nucleic acid polymer comprising two or more nucleotides.

Oligonucleotide gene expression modulator: as used herein, an "oligonucleotide gene expression modulator" is an oligonucleotide agent capable of inducing a selective modulation of gene expression (e.g., increase or decrease) in a living cell by mechanisms including but not limited to an antisense mechanism or by way of an RNA interference (RNAi)-mediated pathway which may include (i) transcription inactivation; (ii) mRNA degradation or sequestration; (iii) transcriptional inhibition or attenuation or (iv) inhibition or attenuation of translation. Oligonucleotide gene expression modulators include virtually any regulatory RNA, such as but not limited to antisense oligonucleotides, miRNA, siRNA, RNAi, shRNA, aptamers and any analogs or precursors thereof.

Oligonucleotide knockdown agent: as used herein, an "oligonucleotide knockdown agent" is an oligonucleotide species which can inhibit gene expression by targeting and binding an intracellular nucleic acid in a sequence-specific manner. Non-limiting examples of oligonucleotide knockdown agents include siRNA, miRNA, shRNA, dicer substrates, antisense oligonucleotides, decoy DNA or RNA, antigene oligonucleotides and any analogs and precursors thereof.

As used herein, the term "oligonucleotide" refers to a polymer comprising 7-200 nucleotide monomeric units. In some embodiments, "oligonucleotide" encompasses single and or/double stranded RNA as well as single and/or double-stranded DNA.

Furthermore, the terms "nucleotide", "nucleic acid," "DNA," "RNA," and/or similar terms include nucleic acid analogs, i.e. analogs having a modified backbone, including but not limited to peptide nucleic acids (PNA), locked nucleic acids (LNA), phosphono-PNA, morpholino nucleic acids, or nucleic acids with modified phosphate groups (e.g., phosphorothioates, phosphonates, 5'-N-phosphoramidite linkages). Nucleotides can be purified from natural sources, produced using recombinant expression systems and optionally purified, chemically synthesized, etc. As used herein, a "nucleoside" is the term describing a compound comprising a monosaccharide and a base. The monosaccharide includes but is not limited to pentose and hexose monosaccharides. The monosaccharide also includes monosaccharide mimetics and monosaccharides modified by substituting hydroxyl groups with halogens, methoxy, hydrogen or amino groups, or by esterification of additional hydroxyl groups. In some embodiments, a nucleotide is or comprises a natural nucleoside phosphate (e.g. adenosine, thymidine, guanosine, cytidine, uridine, deoxyadenosine, deoxythymidine, deoxyguanosine, and deoxycytidine phosphate). In some embodiments, the base includes any bases occurring naturally in various nucleic acids as well as other modifications which mimic or resemble such naturally occurring bases. Nonlimiting examples of modified or derivatized bases include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, 2-aminoadenine, pyrrolopyrimidine, and 2,6-diaminopurine. Nucleoside bases also include universal nucleobases such as difluorotolyl, nitroindolyl, nitropyrrolyl, or nitroimidazolyl. Nucleotides also include nucleotides which harbor a label or contain abasic, i.e. lacking a base, monomers. A nucleic acid sequence is presented in the 5' to 3' direction unless otherwise indicated. A nucleotide can bind to another nucleotide in a sequence-specific manner through hydrogen bonding via Watson-Crick base pairs. Such base pairs are said to be complementary to one another. An oligonucleotide can be single stranded, double-stranded or triple-stranded.

RNA interference (RNAi): As used herein, the term "RNA interference" or "RNAi" refers to sequence-specific inhibition of gene expression and/or reduction in target mRNA and protein levels mediated by an at least partially double-stranded RNA, which also comprises a portion that is substantially complementary to a target RNA.

RNAi agent: As used herein, the term "RNAi agent" refers to an oligonucleotide which can mediate inhibition of gene expression through an RNAi mechanism, including but not limited to siRNA, microRNA (miRNA), short hairpin RNA (shRNA), dicer substrate and the precursors thereof.

Short interfering RNA (siRNA): As used herein, the term "short interfering RNA" or "siRNA" refers to an RNAi agent comprising a nucleotide duplex that is approximately 15-50 base pairs in length and optionally further comprises zero to two single-stranded overhangs. One strand of the siRNA includes a portion that hybridizes with a target RNA in a complementary manner. In some embodiments, one or more mismatches between the siRNA and the targeted portion of the target RNA may exist. In some embodiments, siRNAs mediate inhibition of gene expression by causing degradation of target transcripts.

Short hairpin RNA (shRNA): Short hairpin RNA (shRNA) refers to an oligonucleotide having at least two complementary portions hybridized or capable of hybridizing with each other to form a double-stranded (duplex) structure and at least one single-stranded portion. Inhibit gene expression: As used herein, the phrase "inhibit gene expression" means to cause any measurable reduction in the amount of an expression product of the gene. The expression product can be an RNA transcribed from the gene (e.g. an mRNA) and/or a polypeptide translated from an mRNA transcribed from the gene. The level of expression may be determined using standard techniques for measuring mRNA or protein.

Dicer Substrate: a "dicer substrate" is a greater than 25 base pair duplex RNA that is a substrate for the RNase III family member Dicer in cells. Dicer substrates are cleaved to produce approximately 21 base pair duplex small interfering RNAs (siRNAs) that evoke an RNA interference effect resulting in gene silencing by mRNA knockdown.

As used herein, a "substantially non-charged" includes a Zeta potential that is between ±10 to ±30 mV, and/or the presence of a first number (z) of chargeable species that are chargeable to a negative charge (e.g., acidic species that become anionic upon de-protonation) and a second number (0.5·z) of chargeable species that are chargeable to a positive charge (e.g., basic species that become cationic upon protonation).

Therapeutic agent: As used herein, the phrase "therapeutic agent" refers to any agent that, when administered to a subject, organ, tissue, or cell has a therapeutic effect and/or elicits a desired biological and/or pharmacological effect.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition.

References cited herein, and other references include the following:

(1) Georges, M. K., Veregin, R. P. N., Kazmaier, P. M., and Hamer, G. K. (1993) Narrow Molecular-Weight Resins by a Free-Radical Polymerization Process. *Macromolecules* 26, 2987-2988.

(2) Wang, J. S., and Matyjaszewski, K. (1995) Controlled Living Radical Polymerization—Atom-Transfer Radical Polymerization in the Presence of Transition-Metal Complexes. *J Am Chem Soc* 117, 5614-5615.

(3) Maydunne, R. T. A., Rizzardo, E., Chiefari, J., Chang, Y. K., Moad, G., and Thang, S. H. (1999) A more versatile route to block copolymer and other polymers of complex architecture by living radical polymerization: the RAFT process. *Macromolecules* 32, 6977-6980.

(4) Chiefari, J., Chang, Y. K., Ercole, F., Krstina, J., Jeffery, J., Le, T. P. T., Mayadunne, R. T. A., Meijs, G. F., Moad, C. L., Moad, G., Rizzardo, E., and Thang, S. H. (1999) Living free-radical polymerization by reversible addition-fragmentation transfer: the RAFT process. *Macromolecules* 31, 5559-5562.

(5) Convertine, A. J., Ayres, N., Scales, C. W., Lowe, A. B., and McCormick, C. L. (2004) Facile, controlled, room-temperature RAFT polymerization of N-isopropylacrylamide. *Biomacromolecules* 5, 1177-1180.

(6) Moad, G., Rizzardo, E., and Thang, S. H. (2005) Living radical polymerization by the RAFT process. *Aust J Chem* 58, 379-410.

(7) Sumerlin, B. S., Donovan, M. S., Mitsukami, Y., Lowe, A. B., and McCormick, C. L. (2001) Water-soluble polymers. 84. Controlled polymerization in aqueous media of anionic acrylamido monomers via RAFT. *Macromolecules* 34, 6561-6564.

(8) Schilli, C., Lanzendorfer, M. G., and Muller, A. H. E. (2002) Benzyl and cumyl dithiocarbamates as chain transfer agent in the RAFT polymerization of N-isopropylacrylamide. In situ FT-NIR and MALDI-TOF MS investigation. *Macromolecules* 35, 6819-6827.

(9) Vasilieva, Y. A., Thomas, D. B., Scales, C. W., and McCormick, C. L. (2004) Direct controlled polymerization of a cationic methacrylamido monomer in aqueous media via the RAFT p(r)ocess. *Macromolecules* 37, 2728-2737.
(10) Ganachaud, F., Monteiro, M. J., Gilbert, R. G., Dourges, M. A., Thang, S. H., and Rizzardo, E. (2000) Molecular weight characterization of poly(N-isopropylacrylamide) prepared by living free-radical polymerization. *Macromolecules* 33, 6738-6745.
(11) Segui, F., Qiu, X. P., and Winnik, F. M. (2008) An efficient synthesis of telechelic poly(N-isopropylacrylamides) and its application to the preparation of alpha, omega-dicholesteryl and alpha, omega-dipyrenyl polymers. *J Polym Sci Pol Chem* 46, 314-326.
(12) Lowe, A. B., Sumerlin, B. S., Donovan, M. S., and McCormick, C. L. (2002) Facile preparation of transition metal nanoparticles stabilized by well-defined (co)polymers synthesized via aqueous reversible addition-fragmentation chain transfer polymerization. *J Am Chem Soc* 124, 11562-3.
(13) Scales, C. W., Convertine, A. J., and McCormick, C. L. (2006) Fluorescent labeling of RAFT-generated poly(N-isopropylacrylamide) via a facile maleimide-thiol coupling reaction. *Biomacromolecules* 7, 1389-1392.
(14) Kulkarni, S., Schilli, C., Muller, A. H. E., Hoffman, A. S., and Stayton, P. S. (2004) Reversible meso-scale smart polymer-protein particles of controlled sizes. *Bioconjugate Chem* 15, 747-753.
(15) Boyer, C., Bulmus, V., Liu, J. Q., Davis, T. P., Stenzel, M. H., and Barner-Kowollik, C. (2007) Well-defined protein-polymer conjugates via in situ RAFT polymerization. *J Am Chem Soc* 129, 7145-7154.
(16) De, P., Gondi, S. R., and Sumerlin, B. S. (2008) Folate-conjugated thermoresponsive block copolymers: Highly efficient conjugation and solution self-assembly. *Biomacromolecules* 9, 1064-1070.
(17) Heredia, K. L., Nguyen, T. H., Chang, C., Bulmus, V., Davis, T. P., and Maynard, H. D. (2008) Reversible siRNA-polymer conjugates by RAFT polymerization. *Chemical Communications* 28, 3245-3247.
(18) Maynard, H. D., Heredia, K. L., Li, R. C., Parra, D. P., and Vazquez-Dorbatt, V. (2007) Thermoresponsive biohybrid materials synthesized by ATRP. *J Mater Chem* 17, 4015-4017.
(19) Venkataraman, S., and Wooley, K. L. (2006) ATRP from an amino acid-based initiator: A facile approach for alpha-functionalized polymers. *Macromolecules* 39, 9661-9664.
(20) Bathfield, M., D'Agosto, F., Spitz, R., Charreyre, M. T., and Delair, T. (2006) Versatile precursors of functional RAFT agents. Application to the synthesis of bio-related end-functionalized polymers. *J Am Chem Soc* 128, 2546-2547.
(21) Hong, C. Y., and Pan, C. Y. (2006) Direct synthesis of biotinylated stimuli-responsive polymer and diblock copolymer by RAFT polymerization using biotinylated trithiocarbonate as RAFT agent. *Macromolecules* 39, 3517-3524.
(22) Gondi, S. R., Vogt, A. P., and Sumerlin, B. S. (2007) Versatile pathway to functional telechelics via RAFT polymerization and click chemistry. *Macromolecules* 40, 474-481.
(23) Ranjan, R., and Brittain, W. J. (2007) Combination of living radical polymerization and click chemistry for surface modification. *Macromolecules* 40, 6217-6223.
(24) Liu, J., Bulmus, V., Bamer-Kowollik, C., Stenzel, M. H., and Davis, T. P. (2007) Direct synthesis of pyridyl disulfide-terminated polymers by RAFT polymerization. *Macromol Rapid Comm* 28, 305-314.
(25) Carter, S., Hunt, B., and Rimmer, S. (2005) Highly branched poly(N-isopropylacrylamide)s with imidazole end groups prepared by radical polymerization in the presence of a styryl monomer containing a dithioester group. *Macromolecules* 38, 4595-4603.
(26) Patton, D. L., Mullings, M., Fulghum, T., and Advincula, R. C. (2005) A facile synthesis route to thiol-functionalized alpha, w-telechelic polymers via reversible addition fragmentation chain transfer polymerization. *Macromolecules* 38, 8597-8602.
(27) Deletre, M., and Levesque, G. (1990) Kinetics and Mechanism of Polythioamidation in Solution. 1. Reaction of Mono(Dithioester)S and Bis(Dithioester)S with Excess Amine. *Macromolecules* 23, 4733-4741.
(28) Qiu, X. P., and Winnik, F. M. (2007) Synthesis of alpha, omega-dimercapto poly(N-isopropylacrylamides) by RAFT polymerization with a hydrophilic difunctional chain transfer agent. *Macromolecules* 40, 872-878.
(29) Roberts, M. J., Bentley, M. D., and Harris, J. M. (2002) Chemistry for peptide and protein PEGylation. *Adv Drug Deliver Rev* 54, 459-476.
(30) Toutchkine, A., Nalbant, P., and Hahn, K. M. (2002) Facile synthesis of thiol-reactive Cy3 and Cy5 derivatives with enhanced water solubility. *Bioconjugate Chem* 13, 387-391.
(31) Dufresne, M. H., Gauthier, M. A., and Leroux, J. C. (2005) Thiol-functionalized polymeric micelles: From molecular recognition to improved mucoadhesion. *Bioconjugate Chem* 16, 1027-1033.
(32) Wang, L. X., Kristensen, J., and Ruffner, D. E. (1998) Delivery of antisense oligonucleotides using HPMA polymer: Synthesis of a thiol polymer and its conjugation to water-soluble molecules. *Bioconjugate Chem* 9, 749-757.
(33) Segura, T., and Hubbell, J. A. (2007) Synthesis and in vitro characterization of an ABC triblock copolymer for siRNA delivery. *Bioconjugate Chem* 18, 736-745.
(34) York, A. W., Scales, C. W., Huang, F. Q., and McCormick, C. L. (2007) Facile synthetic procedure for omega, primary amine functionalization directly in water for subsequent fluorescent labeling and potential bioconjugation of RAFT-synthesized (Co)polymers. *Biomacromolecules* 8, 2337-2341.
(35) Nakayama, M., and Okano, T. (2005) Polymer terminal group effects on properties of thermoresponsive polymeric micelles with controlled outer-shell chain lengths. *Biomacromolecules* 6, 2320-2327.
(36) Henry, S. M., El-Sayed, M. E. H., Pirie, C. M., Hoffman, A. S., and Stayton, P. S. (2006) pH-responsive poly(styrene-alt-maleic anhydride) alkylamide copolymers for intracellular drug delivery. *Biomacromolecules* 7, 2407-2414.
(37) El-Sayed, M. E. H., Hoffman, A. S., and Stayton, P. S. (2005) Rational design of composition and activity correlations for pH-sensitive and glutathione-reactive polymer therapeutics (vol 101, pg 47, 2005). *J Control Release* 104, 415-+.
(38) Cheung, C. Y., Stayton, P. S., and Hoffman, A. S. (2005) Poly(propylacrylic acid)-mediated serum stabilization of cationic lipoplexes. *J Biomat Sci-Polym E* 16, 163-179.
(39) Kyriakides, T. R., Cheung, C. Y., Murthy, N., Bornstein, P., Stayton, P. S., and Hoffman, A. S. (2002) pH-sensitive polymers that enhance intracellular drug delivery in vivo. *J Control Release* 78, 295-303.
(40) Johns, R. E., Hoffman, A. S., and Stayton, P. S. (2004) Expression analysis of LPS stimulated THP-1 cells treated with antisense IRAK1 delivered using a pH-sensitive, membrane disruptive polymer. *Mol Ther* 9, S242-S242.
(41) Convertine, A. J., Benoit, D. S. W., Duvall, C. L., Hoffman, A. S., and Stayton, P. S. (2008) Novel endosomolytic diblock copolymer for siRNA delivery. *J Control Release In Press.*
(42) Flanary, S., Hoffman, A. S., and Stayton, P. S. (2008) Antigen delivery with poly(propylacrylic acid) conjugation enhances MHC-1 presentation and T-cell activation. *Bioconjugate Chem In Press.*
(43) Narain, R., Gonzales, M., Hoffman, A. S., Stayton, P. S., and Krishnan, K. M. (2007) Synthesis of monodisperse biotinylated p(NIPAAm)-coated iron oxide magnetic nanoparticles and their bioconjugation to streptavidin. *Langmuir* 23, 6299-6304.
(44) Lai, J. J., Hoffman, J. M., Ebara, M., Hoffman, A. S., Estournes, C., Wattiaux, A., and Stayton, P. S. (2007) Dual magnetic-/temperature-responsive nanoparticles for microfluidic separations and assays. *Langmuir* 23, 7385-7391.
(45) Ebara, M., Hoffman, J. M., Stayton, P. S., and Hoffman, A. S. (2007) Surface modification of microfluidic channels by UV-mediated graft polymerization of non-fouling and 'smart' polymers. *Radiat Phys Chem* 76, 1409-1413.
(46) Amou, S., Nishimura, S., Takahashi, A., Hagiwara, T., Hamana, H., and Narita, T. (1999) Synthesis and polymerization of N-(4-Tetrahydropyranyloxyphenyl)maleimide. *J Polym Sci Pol Chem* 37, 341-347.
(47) Hill, D. T., Shao, L. Y., Pomery, P. J., and Whittaker, A. K. (2001) The radical homopolymerization of N-phenylmaleimide, N-n-hexylmaleimide and N-cyclohexylmaleimide in tetrahydrofuran. *Polymer* 42, 4791-4802.
(48) Zhao, B., Wang, Y., Lu, C., Shen, Q., and Deng, M. (2005) Polymerization of N-Phenyl Maleimide by Lanthanide Complexes. *J Polym Sci Pol Chem* 43, 3966-3972.
(49) Sandreczki, T. C., and Brown, I. M. (1990) Characterization of the free-radical homopolymerization of N-methylmaleimide. *Macromolecules* 23, 1979-1983.
(50) Caulfield, M. J., and Solomon, D. H. (1999) Studies on polyimides: 2. Formation of high molecular weight poly(N-(hydroxyphenyl) maleimides). *Polymer* 40, 1251-1260.
(51) Ferritto, M., and Tirrell, D. A. (1992) Poly(2-Ethylacrylic Acid). *Macromolecular Syntheses* 11, 59-62.
(52) Li, M., De, P., Gondi, S. R., and Sumerlin, B. S. (2008) End group transformations of RAFT-generated polymers with bismaleimides: Functional telechelics and modular block copolymers. *J Polym Sci Pol Chem* 46, 5093-5100.
(53) Jeong, J. H., Kim, S. H., Kim, S. W., and Park, T. G. (2005) In vivo tumor targeting of ODN-PEG-folic acid/PEI polyelectrolyte complex micelles. *J Biomater Sci Polym Ed* 16, 1409-19.
(54) Song, E., Zhu, P., Lee, S. K., Chowdhury, D., Kussman, S., Dykxhoorn, D. M., Feng, Y., Palliser, D., Weiner, D. B., Shankar, P., Marasco, W. A., and Lieberman, J. (2005) Antibody mediated in vivo delivery of small interfering RNAs via cell-surface receptors. *Nat Biotechnol* 23, 709-17.
(55) Hilgenbrink, A. R., and Low, P. S. (2005) Folate receptor-mediated drug targeting: From therapeutics to diagnostics. *Journal of Pharmaceutical Science* 94, 2135-2146.
(56) Bae, K. H., Lee, Y., and Park, T. G. (2007) Oil-encapsulating PEO-PPO-PEO/PEG shell cross-linked nanocapsules for target-specific delivery of paclitaxel. *Biomacromolecules* 8, 650-6.

The following Examples demonstrate various aspects of the invention, including polymer chain extension using functionalized chain extension monomers, and use thereof to form polymeric compounds such as chain-extended polymer compounds and polymer bioconjugates. The Examples, however, are not intended to be limiting.

EXAMPLES

Overview and Discussion of Experimental Results

In the following examples, N-substituted maleimido chain extension monomers have been used in a chain extension polymerization to add a single maleimido chain extension residue onto a RAFT polymer chain with near quantitative efficiency. See Scheme 1, FIG. 8. The maleimido residue includes an amine-functional reactive group, which is available for conjugation reactions. In one approach, the chain extension monomer N-(2-aminoethyl)maleimide trifluoroacetate was used to introduce a single primary amine to the ω-terminus of various polymer chains, including: (i) a poly(dimethylaminoethyl methacrylate) (polyDMAEMA) chain (Example 1A); (ii) a block copolymer [poly(dimethylaminoethyl methacrylate)]-b-[dimethylaminoethyl methacrylate/butyl methacrylate/propylacrylic acid](poly(DMAMEA)-b-DMAEMA/PAA/BMA) chain (Example 1B), and poly(N-isopropyl acrylamide) (polyNIPAM) chain (Example 1C). Evidence for retention of functional RAFT end groups is provided, including for example by synthesis results where chain extended polyDMAEMA (Mn=10,600, Mw/Mn=1.14) (Example 2) was subsequently used as a macromolecular chain transfer agent for the further polymerization with styrene, yielding a diblock polymer of low polydispersity (Mn=20,300, Mw/Mn=1.11) (Example 3). Such example also demonstrates diblock copolymers with an amine-functional bioconjugation site located at the junction between the two blocks. The chain-extended polymers are shown to be functionalized with an amine-reactive fluorescent dye (Example 4) and with folic acid (Example 5) at conjugation efficiencies of 86 and 94%, respectively.

Figure 2A:
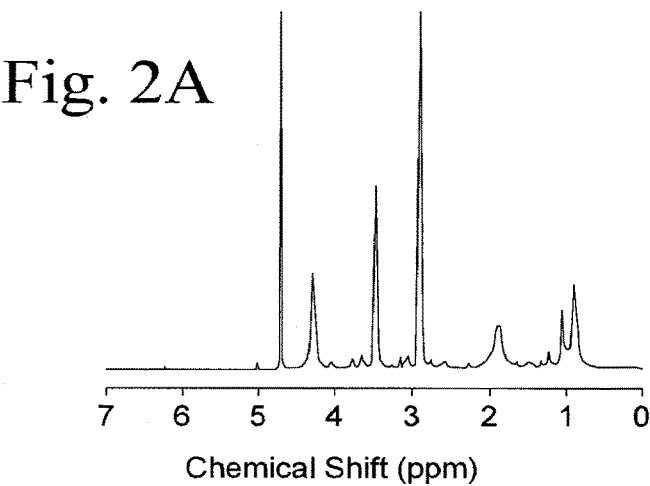
FIG. 2 (A, B) illustrates experimental analytical data regarding chain extension of a DMAEMA polymer chain prepared by RAFT radical polymerization (Example 1A), with N-(2-aminoethyl) maleimide trifluoroacetate ("AM") as a chain extension monomer (Example 2), including $^1$H-NMR (main, FIG. 2A) of pDMAEMA after chain extension with AM, and a triplet at δ=3.77 (inset, FIG. 2B) that results from the addition of AM to the polymer chain.
Figure 2B:
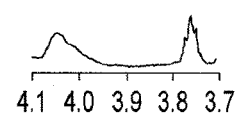

With further reference to Scheme 1 (FIG. 8), the triflate salt of N-(2-aminoethyl)maleimide (AM) was used to introduce primary amine functionality on the ω-end of polymer chains. (Example 1). The incorporation of a chain extension residue was determined using 1H-NMR. (Example 2). FIG. 2 shows the spectrum of a chain extended pDMAEMA-AM macro-CTA. The emergence of the triplet at δ=3.77 corresponding to the ($NCH_2CH_2$) group in AM and the absence of free vinyl peaks at δ=6.8 shows that AM is incorporated into the pDMAEMA polymer and not present as a contaminating monomer. By comparing the pDMAEMA ($CO_2CH_2$) peak area at δ=4.1 to the AM peak area at δ=3.77, and using the molecular weight of pDMAEMA determined by GPC (Example 1), the number of AM residues incorporated into each polymer chain is calculated at 1.02 (P1, Table 2). This result demonstrates the addition of a single amine-functional maleimide to the ω-end of the polymer chain.

Figure 3A:
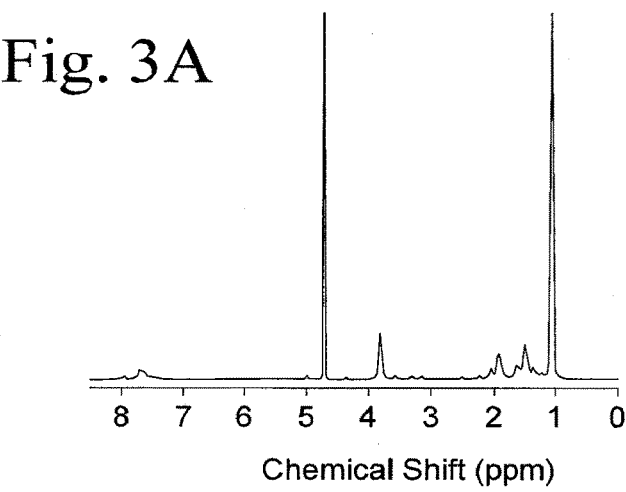
FIG. 3 (A, B) illustrates experimental analytical data regarding chain extension of a NIPAM polymer chain prepared by RAFT radical polymerization (Example 1C) with N-(2-aminoethyl)maleimide trifluoroacetate ("AM") as a chain extension monomer (Example 2), including $^1$H-NMR spectrum (main FIG. 3A) of pNIPAM following chain extension with AM. The inset (FIG. 3B) shows the triplet at δ=3.15 that results from the addition of AM to the polymer chain and the quartet at δ=3.31 that indicates the presence of intact RAFT chain transfer residues, Y.
Figure 3B:
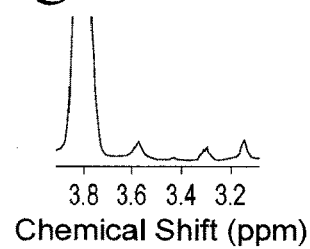

The applicability of functionalizing polymer chains by such chain extension approach was demonstrated beyond methacrylic polymers. Experiments using poly(N-isopropylacrylamide) (pNIPAM) showed that acrylamido polymers were likewise functionalized by maleimido chain extension. FIG. 3 shows the 1H-NMR spectrum of a chain extended pNIPAM-AM macro-CTA. The triplet at δ=3.15 corresponds to the ($CH_2CH_2NH_2$) group in AM and the spectrum is free of vinyl peaks, indicating incorporation of AM into the pNIPAM polymer. The number of AM residues incorporated into each polymer was determined to be 0.97 (P3, Table 2) by comparing the pNIPAM methine peak area (NHCH(CHs)$_2$) at δ=3.81 to the AM peak area at δ=3.15 and using the molecular weight of pNIPAM determined by GPC. Moreover, the AM peak area can be compared directly to the (SCH$_2$CH$_3$) peak from the Z-group of the CTA at δ=3.31, indicating that the CTA and AM are present on the polymer in a 1:1 ratio. Calculation of the degree of polymerization based on the pNIPAM methine peak and the CTA peak at δ=3.31 yields the degree of polymerization expected from GPC measurements, providing further evidence that pNIPAM has been successfully functionalized by a single AM residue and that functional CTA moieties are retained on the polymer chain end.

Figure 4A:
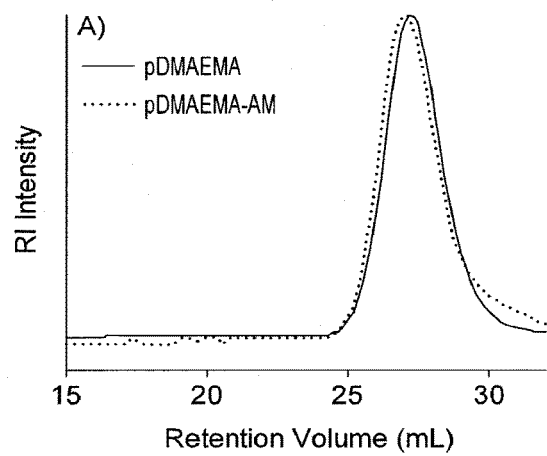
FIG. 4 (A, B) illustrates experimental analytical data, including GPC traces showing the molecular weight distribution of a pDMAEMA polymer chain (Example 1A) and a pDMAEMA-AM chain-extended polymer compound (Example 2) (FIG. 4A), and GPC traces of a pDMAEMA-AM-STY block copolymer (Example 3) and the corresponding pDMAEMA-AM macro-CTA (Example 2A) (FIG. 4B).

The chain extension conditions did not result in changes to the molecular weight distribution of the polymer undergoing extension. FIG. 4A shows the RI traces for pDMAEMA and pDMAEMA-AM (P1, Table 2) following chain extension. No apparent shift in the peak elution volume results from chain extension, consistent with the addition of a single monomer to the chain end, and no change was observed in the calculated Mn (8,100 g/mol) upon chain extension. Moreover, no peak broadening is exhibited in the RI traces, as would be expected if significant polymer-polymer coupling or formation of homomaleimide polymer fragments were to occur (Mw/Mn=1.21 and 1.26 before and after chain extension, respectively). Similarly, no significant changes in molecular weight distribution were observed after chain extension of pNIPAM (Mn=8,000 Mw/Mn=1.16, and Mn=8,000 Mw/Mn=1.17) or the block copolymer pDMAEMA-b-DMAEMA/BMA/PAA (Mn=19,400 Mw/Mn=1.42, and Mn=19,500 Mw/Mn=1.45) (P4, Table 2).

Figure 4B:
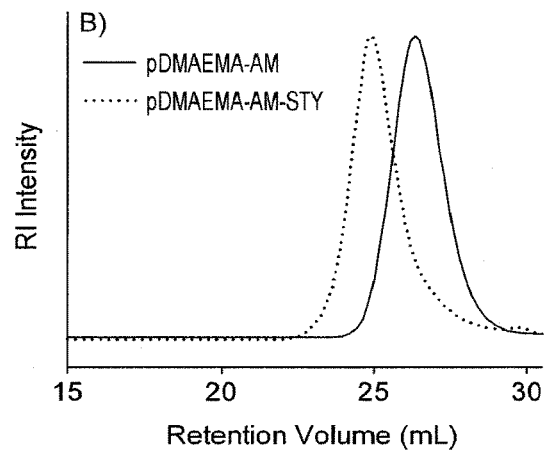

The absence of substantial aminolysis of the chain transfer agent and/or chain transfer residue via side reaction was demonstrated. GPC traces provided no evidence of polymer coupling following chain extension (Example 1). Also, an additional chain-extended pDMAEMA-AM was prepared for use as a macro-CTA in a subsequent styrene polymerization (Mn=10,600, Mw/Mn=1.14) (Example 3). The living character of the macro-CTA was demonstrated by subsequent block formation using the pDMAEMA-AM macro-CTA to polymerize styrene and form the block copolymer pDMAEMA-AM-STY, without yielding polymers with broad or multi-modal molecular weight distributions (e.g., as would have been expected in the presence of non-functional macro-CTA). FIG. 4B shows RI traces for the pDMAEMA-AM macro-CTA and for the triblock polymer obtained by block polymerization, pDMAEMA-AM-STY (P2, Table 2). A clear shift in the retention volume of the polymer was observed following polymerization, and the molecular weight distribution of the triblock polymer was characteristically narrow (Mn=20,300 and Mw/Mn=1.11). These results are consistent with an absence of significant aminolysis of the CTA. Further evidence is demonstrated by examination of the 1H-NMR spectrum of pNIPAM-AM, shown in FIG. 3. This spectrum shows the methylene peak from the Z-group of the CTA at δ=3.31. The ratio of this peak area to the methine peak area in chain-extended pNIPAM-AM is the same as the corresponding ratio in the parent pNIPAM, indicating that no detectable aminolysis of the CTA occurs during chain-extension.

Figure 5A:
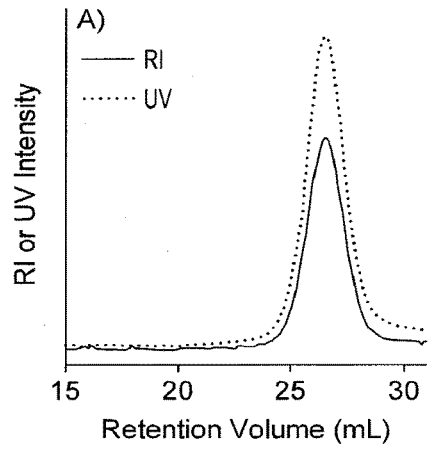
FIG. 5 (A, B) illustrates experimental analytical data relating to chain extended polymers conjugated to amine-reactive pyrene dye ("P"), including RI and UV traces of pDMAEMA-AM-P following pyrene conjugation (Example 4A) (FIG. 5A) and UV absorbance of unmodified (non-conjugated) pDMAEMA-AM (Example 2A) (showing limited UV absorbance due to the trithiocarbonate moiety on the chain end) and of pyrene-conjugated pDMAEMA-AM-P (Example 4A) (exhibiting significantly increased absorption) (FIG. 5B).
Figure 5B:
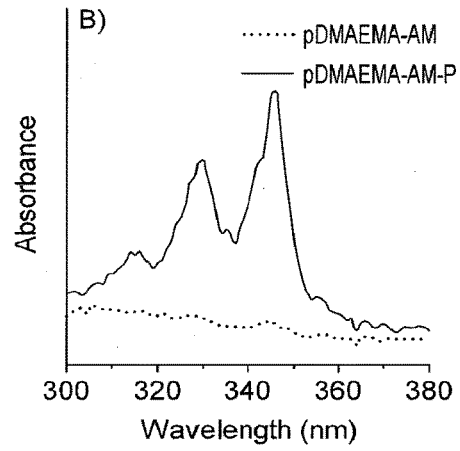

Further experiments confirmed that the functional amine groups introduced to the polymer chains by chain-extension were reactive and available. A fluorescent dye was used as a model compound for imaging agent conjugations. (Example 4) Briefly, amine reactive 1-pyrenebutanoic acid succinimidyl ester (PNHS) was used to label pDMAEMA-AM, and the amount of pyrene conjugated was evaluated by GPC and UV spectroscopy following purification. FIG. 5A shows normalized RI and UV traces for pyrene-labeled pDMAEMA-AM. Upon reaction with PNHS, an intense UV signal was observed with polymer elution that was not present in unconjugated pDMAEMA-AM, indicating that the pDMAEMA-AM chains were successfully labeled with pyrene. FIG. 5B shows the UV absorbance spectra of pyrene-labeled pDMAEMA-AM and unlabeled pDMAEMA-AM, illustrating the significant increase in absorptivity that occurred upon pyrene addition. The percentage of pDMAEMA-AM chains conjugated to pyrene was determined to be 86.1% (P1, Table 2) by comparing the UV peak area associated with polymer elution to a calibration curve. Similarly, PNHS was also used to label the primary amine located at the maleimido-junction of the DMAEMA and STY block segments in pDMAEMA-AM-STY (P2, Table 2). The degree of conjugation to this polymer was 44%; steric effects of the large styrene block may have reduced the conjugation efficiency.

Figure 6A:
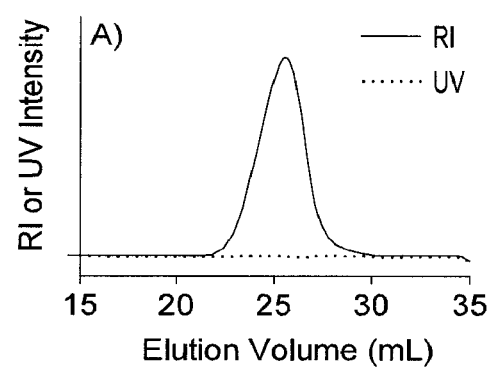
FIG. 6 (A, B) illustrates experimental analytical data, relating to chain extended polymers conjugated to folic acid, including RI and UV traces of pDMAEMA-b-DMAEMA/BMA/PAA-AM before conjugation to folic acid (Example 2B) (FIG. 6A), and RI and UV traces of pDMAEMA-b-DMAEMA/BMA/PAA after the addition of folic acid (Example 5) (FIG. 6B).
Figure 6B:
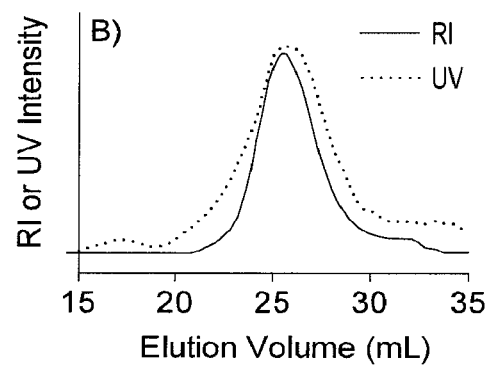

Further demonstration of bioconjugation to an amine-functional maleimido chain extension residues was effected using folic acid and the AM chain-extended pDMAEMA-b-DMAEMA/BMA/PAA block copolymer. (Example 5). Folic acid is a targeting ligand, mediating greater internalization for cells that express or over-express the folic acid receptor (55, 56). FIG. 6A shows the RI and UV GPC traces of the unmodified copolymer while FIG. 6B shows the RI and UV GPC traces of the copolymer-folate conjugate. The unmodified copolymer shows negligible UV absorbance at 363 nm (FIG. 6A), while an intense UV signal was associated with polymer elution in the case of the copolymer-folate conjugate (FIG. 6B). The degree of folate conjugation to the copolymer was determined by comparison to a calibration curve of free folic acid, and found to be 94% (P4, Table 1). Notably, such efficient conjugation reactions here were conducted under relatively moderate conditions—for less than 24 hours at room temperature and relatively low stoichiometric ratios.

The preparation of biotin-conjugated polymers was effectively demonstrated using two general approaches: (i) one approach involved conjugation of a biomolecular moiety to the chain-extended polymer—after chain extension polymerization; and (ii) the other approach involved a chain-extension polymerization reaction using a chain extension monomer to which the biomolecular moiety was conjugated—before chain extension polymerization. Specifically, in one example, the polymer bioconjugate, pNIPAM-AM-Biotin, was prepared by conjugation of biotin-NHS to chain-extended polymer (NIPAM-AM) (Example 6A). In another example, the polymer bioconjugate, pDMAEMA-AM-Biotin, was prepared by chain extension polymerization using biotin-maleimide monomer (Example 6B). Both approaches were effective for preparing biotin-conjugated chain-extended polymers.

Polymer chains (or compositions such as polynucleotide-containing compositions comprising such polymer chains) can be evaluated for effectiveness as a pH-sensitive, membrane disruptive polymer (Example 7). For example, under one, non-limiting, standard applicable for example for screening of polymer chain candidates, a polymer or polymer composition can be considered to be a pH responsive membrane-disruptive if the polymer or polymer composition is substantially non-hemolytic at pH 7.4 and becomes increasingly more hemolytic at the lower pH values (e.g., correlating to pH values associated with endosomes) and at higher concentrations of polymer.

Materials and General Methods

All reagents were purchased from Sigma-Aldrich and used without further purification unless otherwise noted. Dimethylaminoethyl methacrylate (DMAEMA), butyl methacrylate (BMA), and styrene were purified by vacuum distillation. N-isopropylacrylamide (NIPAM) was recrystallized from hexanes. Propylacrylic acid (PAA) was synthesized as previously published (51). Unless noted otherwise, the primary radical source used in all polymerizations was 2,2-azobisisobutyronitrile (AIBN), which was recrystallized from methanol. All polymerizations were conducted under $N_2$ atmosphere.

RAFT Chain Transfer Agent. The trithiocarbonate CTA ethyl cyanovaleric trithiocarbonate (ECT) was synthesized as previously described (41), and used as the CTA in all RAFT polymerizations. Briefly, the synthesis of the chain transfer agent (CTA), 4-Cyano-4-(ethylsulfanylthiocarbonyl) sulfanylpentanoic acid (ECT), utilized for the following RAFT polymerizations, was adapted from a procedure by Moad et al., Polymer, 2005, 46(19): 8458-68. Briefly, ethane thiol (4.72 g, 76 mmol) was added over 10 minutes to a stirred suspension of sodium hydride (60% in oil) (3.15 g, 79 mmol) in diethyl ether (150 ml) at 0° C. The solution was then allowed to stir for 10 minutes prior to the addition of carbon disulfide (6.0 g, 79 mmol). Crude sodium S-ethyl trithiocarbonate (7.85 g, 0.049 mol) was collected by filtration, suspended in diethyl ether (100 mL), and reacted with Iodine (6.3 g, 0.025 mol). After 1 hour the solution was filtered, washed with aqueous sodium thiosulfate, and dried over sodium sulfate. The crude bis (ethylsulfanylthiocarbonyl) disulfide was then isolated by rotary evaporation. A solution of bis-(ethylsulfanylthiocarbonyl) disulfide (1.37 g, 0.005 mol) and 4,4'-azobis(4-cyanopentanoic acid) (2.10 g, 0.0075 mol) in ethyl acetate (50 mL) was heated at reflux for 18 h. Following rotary evaporation of the solvent, the crude 4-Cyano-4 (ethylsulfanylthiocarbonyl) sulfanylpentanoic acid (ECT) was isolated by column chromatography using silica gel as the stationary phase and 50:50 ethyl acetate hexane as the eluent.

The polymers in this study were characterized by gel permeation chromatography using three Tosoh TSK-GEL columns (TSK-α3000, α3000, α4000) connected in series to a Viscotek GPCmax VE2001 and Viscotek RI and UV detectors (VE3580 and VE3210 respectively) (Viscotek, Houston Tx). The mobile phase was HPLC-grade DMF containing 0.1 wt % LiBr. Molecular weight distributions were determined relative to a series of poly(methyl methacrylate) standards. Characterization of polymer-folate conjugates was performed on an HP Agilent 8453 UV-vis spectrophotometer. All NMR spectroscopy was done on a Bruker DRX499 system in $D_2O$.

Example 1

Synthesis of Polymer Chains Using RAFT Polymerization

Example 1A.

Synthesis of Poly(N,N-dimethylaminoethyl methacrylate) (PolyDMAEMA)

The polymer chain poly(DMAEMA) was obtained by RAFT polymerization using experimental conditions appropriate to target the various molecular weights used in this study. As an example of typical conditions, the $[CTA_o]/[I_o]$ ratio was 10:1, the $[CTA_o]/[M_o]$ ratio was 1:150, and the monomer was 50 wt % in N,N'-dimethylformamide (DMF). The polymerization was conducted at 60° C. for 7 hours. The molecular weight and polydispersity were 8,100 g/mol and 1.21 respectively. All DMAEMA polymers were isolated by precipitation in an 80/20 v/v pentane/ether mixture, followed by repeated cycles of dissolution in ether and precipitation in pentane. The polymer was dried under vacuum overnight. Molecular weights distributions were determined by gel permeation chromatography (GPC).

Example 1B.

Synthesis of Poly(DMAMEA)-b-DMAEMA/PAA/BMA Block Copolymer

The block copolymer p(DMAMEA-b-DMAEMA/BMA/PAA) was prepared following previously described protocols (41). Briefly, a pDMAEMA macro CTA ($M_n$=9,000 g/mol, $M_w/M_n$=1.30) was employed for the polymerization of the copolymer block using a $[CTA_o]/[I_o]$ ratio of 10:1 and a $[CTA_o]/[M_o]$ ratio of 1:250 in DMF at 40 wt % monomer. The composition of the feed was 40 mol % butylmethacrylate (BMA), 30 mol % propylacrylic acid (PAA) and 30 mol % DMAEMA. 2,2'-azobis(4-methoxy-2,4-dimethylvaleronitrile) (V70) was the radical source, and the polymerization time was 18 hours at 30° C. The block copolymer was isolated by multiple precipitations in an 80/20 v/v pentane and ether mixture, followed by precipitation in pentane.

Example 1C.

Synthesis of Poly(NIPAM)

The polymer chain poly(NIPAM) was obtained by RAFT polymerization based on previously published conditions (52) using a $[CTA_o]/[I_o]$ ratio of 20:1, a $[CTA_o]/[M_o]$ ratio of 1:100, and the monomer was 33 wt % in p-dioxane. The polymerization was conducted at 70° C. for 120 minutes. pNIPAM was isolated by repeated cycles of precipitation into ethyl ether, followed by dissolution in acetone, and dried under vacuum overnight Example 2

Chain Extension with Maleimide Chain Extension Monomer for Preparation of Poly(DMAEMA)-(AM), Poly(DMAMEA)-b-DMAEMA/PAA/BMA-(AM), Poly(NIPAM)-(AM)

Maleimide chain extension was performed at 60° C. in DMF for 16 hours using N-(2-aminoethyl)-maleimide trifluoroacetate (AM) as the monomer and poly(DMAEMA), poly(NIPAM) or poly(DMAEMA-b-DMAEMA/BMA/PAA) as the macro-CTA (Scheme 1). The polymerizations were conducted with a $[CTA_o]/[I_o]$ ratio of 10:1 and a $[CTA_o]/[M_o]$ ratio of 1:100. The polymerization solution was 60 wt % solvent. As an example polymerization, 400 mg pDMAEMA (49 µmol) and 1.26 g AM (4.9 mmol) were polymerized with 0.81 mg AIBN (4.9 µmol) in 2.5 g DMF. $^1$H-NMR was used to confirm that the macro-CTAs were free of residual monomer prior to chain extension in order to eliminate the possibility of copolymerization during maleimide chain extension.

Chain extended pDMAEMA-AM was isolated by six cycles of precipitation in an 80/20 solution of pentane/ether. Between precipitations, the polymer was redissolved in acetone and separated from any insoluble AM by centrifugation and filtration through 0.2 μm syringe filters. Following precipitation, a solution of pDMAEMA-AM was prepared in deionized water (DI) and the polymer was further purified from residual AM monomer using two PD-10 desalting columns (Amersham, Piscataway N.J.) in series, and lyophilized. Chain extended pNIPAM-AM was purified from AM by running the reaction mixture through two PD-10 columns following 1:2 dilution in DI, then lyophilized. The extent of AM chain extension was determined using $^1$H-NMR and the molecular weight distribution was characterized by GPC.

Example 3

Synthesis of Poly(DMAEMA)-(AM)-STY Block Copolymer Using RAFT Polymerization

Chain extended pDMAEMA-AM was used as a macro-CTA for the polymerization of styrene (pDMAEMA-AM-STY) in order to demonstrate retention of functional RAFT chain ends. The $[CTA_o]/[I_o]$ ratio was 10:1, the $[CTA_o]/[M_o]$ ratio was 1:250, and the monomer was 50 wt % in DMF. The polymerization was conducted at 60° C. for 24 hours, and the polymer was isolated by precipitation in 80/20 v/v pentane/ether as previously described.

Example 4

Conjugation of Pyrene Dye to Polymer Chains Through Extension Moieties (Fluorescent Labeling)

Amine functionalized pDMAEMA-AM and pDMAEMA-AM-STY were labeled with 1-pyrenebutanoic acid succimidyl ester (PNHS) (Invitrogen). pDMAEMA-AM (75 mg, 10 μmol) was dissolved in 1 mL of anhydrous DMF. Subsequently, diisopropylethylamine (123 mg, 0.96 mmol) was added at 2-fold molar excess relative to the number of DMAEMA residues to ensure removal of the triflate salt from the pDMAEMA-AM primary amine. After 60 minutes, PNHS (20 mg, 70 μmol) was added to the solution at 7-fold molar excess relative to the number of pDMAEMA-AM chains, and the reaction was allowed to proceed in the dark at room temperature for 18 hours under anhydrous conditions. At the end of the reaction time, free PNHS was precipitated from solution by the addition of 4 mL of DI water and separated by centrifugation. The supernatant was filtered through a 0.2 μm syringe filter, eluted through 2 PD-10 desalting columns, and dried. The sample was then dissolved in 2.5 mL of 50% v/v DI/DMF, and eluted through 2 additional PD-10 columns in series, and frozen and lyophilized. The percent conjugation was determined by GPC using online UV and RI detectors.

pDMAEMA-AM-STY was labeled using a similar procedure, but PNHS was added at 50 fold molar excess to compensate for the increased steric hindrance of the amine caused by the presence of the styrene block. Following labeling, the reaction mixture was added to 50 mL anhydrous ether causing the precipitation of PNHS, which was removed by centrifugation. pDMAEMA-AM-STY was subsequently precipitated from the ether by the addition of 50 vol % pentane and recovered by centrifugation.

To determine the concentration of pyrene associated with pDMAEMA-AM or pDMAEMA-AM-STY, a linear pyrene calibration curve was generated by injecting multiple known concentrations of pyrene on the GPC column and plotting their corresponding UV peak areas at 338 nm. The concentration of pyrene associated with the polymers was subsequently determined by comparison of the polymer conjugate UV peak area ($\lambda$=338) to the pyrene calibration curve. The UV peak area of the unlabeled polymers was used to account for the contribution of the RAFT CTA to the absorption at 338 nm while maintaining constant RI peak area between the two samples.

Example 5

Conjugation of Folic-Acid to Chain-Extended Polymer Chains (Via Extension Moieties)

Folic acid was activated with dicyclocarbodiimide (DCC) in dry dimethylsulfoxide (DMSO) at a molar ratio of 1:1.1 for 60 minutes at 4° C. A solution of pDMAEMA-b-DMAEMA/BMA/PAA that had been chain extended with N-(2-aminoethyl)maleimide and TEA (1:1 mol ratio with PAA and AM) in DMSO (pDMAEMA-b-DMAEMA/BMA/PAA-AM) was added to the activated folate solution (10:1 folate:polymer ratio), and reacted overnight at room temperature. The polymer-folate conjugate was purified by extensive dialysis in water, then lyophilized. The remaining folic acid was separated from the lyophilized conjugate using a series of 5 PD-10 desalting columns until no further reduction in folic acid absorbance ($\lambda$=363 nm) was observed in the column flow-through. The purified polymer-folate conjugate was dried by lyophilization, and the amount of folate present in the conjugate was determined by UV absorbance relative to a standard curve of free folic acid. No shift in the folate absorbance spectrum was observed as a result of conjugation to the polymer. UV measurements were done in phosphate buffered saline (PBS), pH=7.4. Concentrations of the polymer-folate conjugate were between 0.1 and 1 mg/mL.

Example 6

Preparation of Biotin-Conjugated Chain-Extended Polymers

Example 6A.

Conjugation of Biotin to Chain-Extended Polymer Chains (NIPAM-AM)

In this example, the polymer bioconjugate, pNIPAM-AM-Biotin, was prepared by conjugation of biotin-NHS to chain-extended polymer (NIPAM-AM). The polymer pNIPAM (10,500 g/mol) was chain extended with 2-aminoethyl maleimide (AM), yielding pNIPAM-AM functionalized with 1 primary amine per chain. Subsequently, a pNIPAM-biotin conjugate was prepared by reacting the AM chain extended polymer with NHS-Biotin. To a solution of 650 mg pNIPAM-AM polymer in 1 mL of anhydrous DMSO, 4 mg diisopropylethylamine were added (5×mol excess relative to NIPAM) in order to remove the trifluoroacetate salt from the pNIPAM-AM chain extended amine. After 2 hours, 21 mg biotin NHS (10×mol excess relative to NIPAM) was added to the solution. The reaction was purged with dry nitrogen. After 24 hours reaction, pNIPAM-biotin was purified by diluting the reaction mixture with 2.5 mL of distilled H2O and running the reaction mixture through 2 PD-10 desalting columns in series.

The degree of biotinylation was determined by NMR in D2O by comparing the peak areas at δ=4.3 and δ=4.5 which are characteristic of the (—NCHCHS— and —NCHCH2S—) groups in biotin to the pNIPAM methine peak at δ=3.8 using the molecular weight of pNIPAM. The degree of biotinylation was also determined using a HABA/Avidin assay (Sigma) according to manufacturer's protocols. The results are shown in Table 3.

Example 6B.

Chain Extension of DMAEMA Using Biotin-Conjugated Maleimide Monomer

In this example, the polymer bioconjugate, pDMAEMA-AM-Biotin, was prepared by chain extension polymerization using biotin-maleimide monomer. The polymer pDMAEMA (8,700 g/mol) was chain extended with biotin-maleimide (Pierce) as the chain extension monomer. The pDMAEMA macro-CTA was prepared from 4 g DMAEMA. The [CTAo]/[Mo] ratio was 1:168, the [CTAo]/[Io] ratio was 10:1, the polymerization was 50 wt % in DMF and the reaction time was 7 hours at 60° C. The polymerization was conducted under a $N_2$ atmosphere using AIBN as a free-radical source. For biotin-maleimide chain extension, 200 mg pDMAEMA (23 μmol) was used as the macro-CTA for the chain extension polymerization of biotin-maleimide. The [CTAo]/[Mo] ratio was 1:16, the [CTAo]/[Io] was 20:1, and the polymerization was conducted for 18 hours at 60° C. The polymerization solution was prepared by combining first dissolving the biotin-maleimide in 2 mL DMSO. The pDMAEMA macro-CTA and the AIBN were dissolved in 2 mL DMF. The solutions were combined and the reaction vessel was purged with $N_2$ prior to polymerization. pDMAEMA-biotin was purified using multiple PD-10 columns in series.

The degree of biotinylation was determined by NMR in D2O by comparing the peak area at δ=4.5 to the pDMAEMA methylene peak at δ=4.0 using the molecular weight of DMAEMA. The degree of biotinylation was also determined using a HABA/Avidin assay (Sigma) according to manufacturer's protocols. The results are shown in Table 3.

Example 7

Evaluation of Membrane Destabilizing Activity of Polymer Chains

Polymer chains are evaluated for effectiveness as a pH-sensitive, membrane disruptive polymer chain as follows.

Generally, a pH responsive membrane destabilizing activity is assayed by titrating a polymer or a polymer composition (i.e., a polymer chain (alone) or a polymer chain non-covalently complexed or covalently conjugated to a polynucleotide such as siRNA) into preparations of human red blood cells (RBC) and determining membrane-lytic activity by hemoglobin release (absorbance reading at 540 nm). Three different pH conditions are used to mimic endosomal pH environments (extracellular pH=7.4, early endosome=6.6, late endosome=5.8). Human red blood cells (RBC) are isolated by centrifugation from whole blood collected in vaccutainers containing EDTA. RBC are washed 3 times in normal saline, and brought to a final concentration of 2% RBC in PBS at specific pH (5.8, 6.6 or 7.4).

Polymer or polymer composition is tested at several concentrations. For example for a polymer/siRNA complex, 25 nM siRNA is added to polymer at 1:1, 2:1, 4:1 and 8:1 charge ratios (same polymer concentrations for polymer alone). Solutions of polymer alone or polymer-siRNA complexes are formed at 20× final assayed concentration for 30 minutes and diluted into each RBC preparation. Two different preparations of polymer stock are compared for stability of activity at 9 and 15 days post preparation, stored at 4° C. from day of preparation. RBC with polymer alone or polymer/siRNA complex are incubated at 37° C. for 60 minutes and centrifuged to remove intact RBC. Supernatants are transferred to cuvettes and absorbance determined at 540 nm. Percent hemolysis is expressed as $A_{540}$ sample/$A_{540}$ of 1% Triton X-100 treated RBC (control for 100% Lysis).

The various examples herein are to be considered illustrative, and not defining the scope of the invention.

TABLE 1

Chain extension monomers.

(M1)

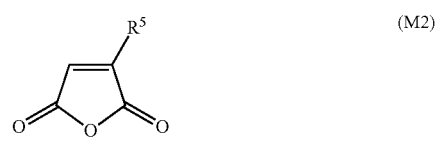

(M2)

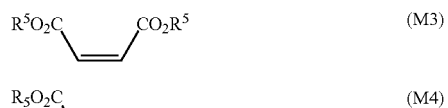

(M3)

(M4)

(M5)

(M6)

(M7)

(M8)

(M9)

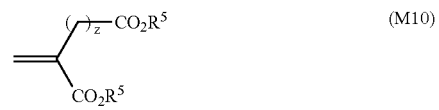

(M10)

z = 0, 1, 2, 3

TABLE 1-continued

Chain extension monomers.

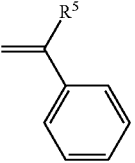
(M11)

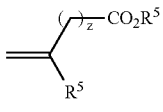
z = 0, 1, 2, 3
(M12)

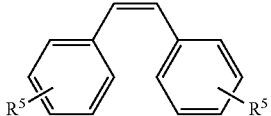
(M13)

TABLE 1-continued

Chain extension monomers.

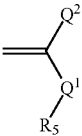
(M17)

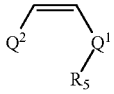
(M18)

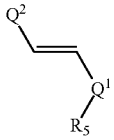
(M19)

TABLE 2

Molecular weight distributions, degree of chain extension and degree of conjugation.

| | | | | % AM | % Conjugation Efficiency | |
|---|---|---|---|---|---|---|
| # | Polymer | $M_n{}^a$ | $M_w/M_n{}^a$ | Extension[b] | Pyrene[a] | Folate[c] |
| P1 | pDMAEMA-AM | 8100 | 1.26 | 102 | 86 | — |
| P2 | pDMAEMA-AM-STY | 20300 | 1.11 | 82 | 44 | — |
| P3 | pNIPAM-AM | 8000 | 1.17 | 97 | — | — |
| P4 | pDMAEMA-b-DMAEMA/BMA/PAA | 19500 | 1.45 | — | — | 94 |

[a] Determined by GPC
[b] Determined by $^1$H-NMR
[c] Determined by UV spectroscopy TABLE 1-continued Chain extension monomers.

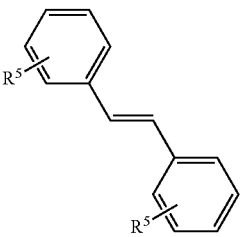
(M14)

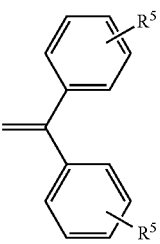
(M15)

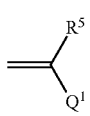
(M16)

TABLE 3

Degree of biotinylation for biotin-conjugated chain-extended polymers.[a, b]

| | | | Biotin/Chain | |
|---|---|---|---|---|
| Polymer | Mn | Method | NMR | HABA |
| NIPAM-AM | 10,500 | NHS ester | 0.8 | 0.5 |
| DMAEMA | 9,700 | Ch. Ext. | 4.3 | 1.7 |

[a] Polymer bioconjugate (pNIPAM-AM-Biotin) prepared by conjugation of biotin-NHS to chain-extended polymer (NIPAM-AM).
[b] Polymer bioconjugate (pDMAEMA-AM-Biotin) prepared by biotin-maleimide chain extension polymerization.

The invention claimed is:
1. A method for preparing a polymer, the method comprising:
(a) providing a macromolecular chain transfer agent having a formula P″—Y, wherein P″ is a first polymer chain, Y is a chain transfer residue having a formula SC(=S)Z, and Z is an activating group, and
(b) reacting a chain extension monomer and the macromolecular chain transfer agent under reversible addition-fragmentation chain transfer (RAFT) chain extension conditions to form a polymer having a formula P″-(E)$_k$-Y, wherein k is an integer ranging from 1 to 20, and wherein chain extension residue E has a formula E3

(E3)

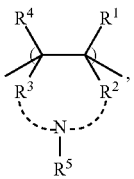

wherein
R¹ and R⁴ are each hydrogen,
R², N—R⁵, and R³, together form an N-substituted imidyl moiety represented by the formula —C(O)NR⁵C(O)—, and
R⁵ is a $C_1$-$C_{20}$ moiety comprising (i) a functional group or (ii) a functional group covalently coupled to a biomolecular agent through a linking moiety, wherein the $C_1$-$C_{20}$ moiety is selected from the group consisting of hydrocarbyl, substituted hydrocarbyl, hetero-hydrocarbyl, substituted hetero-hydrocarbyl, carbocyclic, substituted carbocyclic, heterocyclic, substituted heterocyclic, aryl, substituted aryl, heteroaryl, substituted heteroaryl, and fused-multiring structures comprising one or more of the foregoing, and wherein the functional group is selected from the group consisting of amino, ammonio, imino, amido, imidyl, nitrile, azo, azido, cyano, cyanato, isocyanato, isothiocyanto, hydrazide, nitro, nitroso, nitrosooxy, pyridyl, hydroxyl, alkoxy, carboxyl, ester, acyl, halo, haloformyl, phosphino, phosphoric, phospho, sulfide, disulfide, thio, thiol, sulfonyl, sulfo, sulfinyl, alkenyl, alkynl, allenyl, and silyl.

2. The method of claim 1, further comprising
(c) reacting a set of one or more monomers and the polymer of formula P″-(E)$_k$-Y under RAFT polymerization conditions to form a polymer having a formula P″-(E)$_k$-P‴—Y, wherein P‴ is a second polymer chain.

3. The method of claim 1, further comprising preparing the macromolecular chain transfer agent of formula P″—Y before step (a).

4. The method of claim 3, wherein preparing the macromolecular chain transfer agent comprises reacting a first set A of one or more monomers and a chain transfer agent comprising a thio-carbonyl-thio moiety under RAFT polymerization conditions.

5. The method of claim 4, further comprising
(c) reacting a second set B of one or more monomers and the polymer of formula P″-(E)$_k$-Y under RAFT polymerization conditions to form a polymer having a formula P″-(E)$_k$-P‴—Y, wherein P‴ is a second polymer chain.

6. The method of claim 5, wherein the second set B of one or more monomers is different from the first set A of one or more monomers.

7. The method of claim 1, further comprising cleaving the chain transfer residue Y to yield a chain transfer residue derivative, Y*.

8. The method of claim 7, wherein Y* is selected from the group consisting of hydrogen and —SH.

9. The method of claim 1, wherein k is an integer ranging from 1 to 10.

10. The method of claim 9, wherein each of the macromolecular chain transfer agent and the polymer of formula P‴-(E)$_k$-Y has a polydispersity index, $M_w/M_n$, of less than 1.5, and wherein the polydispersity index of the polymer of formula P″-(E)$_k$-Y differs from the polydispersity index of the macromolecular chain transfer agent by not more than 10%.

11. The method of claim 10, wherein the polydispersity index of the polymer of formula P″-(E)$_k$-Y differs from the polydispersity index of the macromolecular chain transfer agent by not more than 5%.

12. The method of claim 1, wherein R⁵ comprises (ii) the functional group covalently coupled to the biomolecular agent through the linking moiety.

13. The method of claim 12, wherein the biomolecular agent is selected from the group consisting of a therapeutic agent and a targeting moiety.

14. The method of claim 12, wherein the biomolecular agent is selected from the group consisting of a polynucleic acid, a polyamino acid, a polysaccharide, and a small molecule.

15. A method for preparing a polymer, the method comprising:
(a) providing a macromolecular chain transfer agent having a formula P″—Y, wherein P″ is a first polymer chain, Y is a chain transfer residue having a formula SC(=S)Z, and Z is an activating group, and
(b) reacting a chain extension monomer and the macromolecular chain transfer agent under reversible addition-fragmentation chain transfer (RAFT) chain extension conditions to form a polymer having a formula P″-(E)$_k$-Y, wherein k is an integer ranging from 1 to 20, and wherein chain extension residue E has a formula E3

wherein
R¹ and R⁴ are each hydrogen,
R², N-R⁵, and R³, together form an N-substituted imidyl moiety represented by the formula —C(O)NR⁵C(O)—, and
R⁵ is a $C_1$-$C_{20}$ moiety comprising a primary or secondary amine, wherein the $C_1$-$C_{20}$ moiety is selected from the group consisting of hydrocarbyl, substituted hydrocarbyl, hetero-hydrocarbyl, substituted hetero-hydrocarbyl, carbocyclic, substituted carbocyclic, heterocyclic, substituted heterocyclic, aryl, substituted aryl, heteroaryl, substituted heteroaryl, and fused-multi-ring structures comprising one or more of the foregoing, and
(c) conjugating a biomolecular agent to the polymer of formula P″-(E)$_k$-Y utilizing the primary or secondary amine.

16. The method of claim 15, wherein the biomolecular agent is selected from the group consisting of a therapeutic agent and a targeting moiety.

17. The method of claim 15, wherein the biomolecular agent is selected from the group consisting of a polynucleic acid, a polyamino acid, a polysaccharide, and a small molecule.

* * * * *